United States Patent
Weissman et al.

(10) Patent No.: US 8,420,776 B2
(45) Date of Patent: Apr. 16, 2013

(54) UBE2G2 BINDING DOMAIN IN THE UBIQUITIN LIGASE GP78 AND METHODS OF USE THEREOF

(75) Inventors: Allan Weissman, Bethesda, MD (US); Jennifer Mariano, Frederick, MD (US); Bo Chen, Frederick, MD (US); Yien Che Tsai, Frederick, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 946 days.

(21) Appl. No.: 11/597,453

(22) PCT Filed: Apr. 27, 2005

(86) PCT No.: PCT/US2005/014635
§ 371 (c)(1),
(2), (4) Date: Jul. 23, 2007

(87) PCT Pub. No.: WO2006/007023
PCT Pub. Date: Jan. 19, 2006

(65) Prior Publication Data
US 2008/0090249 A1    Apr. 17, 2008

Related U.S. Application Data

(60) Provisional application No. 60/583,263, filed on Jun. 26, 2004.

(51) Int. Cl.
*C07K 14/435* (2006.01)
*C12P 21/02* (2006.01)

(52) U.S. Cl.
USPC ................... 530/326; 530/324; 435/69.1

(58) Field of Classification Search ............. 530/326, 530/324; 435/69.1
See application file for complete search history.

(56) References Cited

U.S. PATENT DOCUMENTS

| | | | |
|---|---|---|---|
| 6,444,425 B1 | 9/2002 | Reed et al. | |
| 7,745,391 B2 * | 6/2010 | Mintz et al. | 514/19.3 |
| 2006/0211718 A1 | 9/2006 | Weissman et al. | |
| 2007/0083334 A1 * | 4/2007 | Mintz et al. | 702/19 |

OTHER PUBLICATIONS

GenBank record No. Q9UKV5, gp78, autocrine motility factor receptor, isoform 2 (a ubiquitin protein ligase), 2003.*
ClustalW multi-sequence aligment of odd-numbered sequences SEQ ID Nos. 9-49, performed on the EMBL-EBI web site, www.ebi.ac.uk, Aug. 6, 2010.*
Shimizu et al., "The autocrine motility factor receptor gene encodes a novel type of seven transmembrane protein," FEBS Lett 456:295-300, 1999.*
Result 9, search in issued patents polypeptide database, alignment of instant SEQ ID No. 34 with SEQ ID No. 988009 of Mintz et al. (US 2007/0083334 or 7,745,391, search performed on Nov. 29, 2010.*

(Continued)

*Primary Examiner* — Rosanne Kosson
(74) *Attorney, Agent, or Firm* — Edwards Wildman Palmer LLP; Peter F. Corless

(57) ABSTRACT

The present invention features isolated nucleic acid molecules, designated G2BD nucleic acid molecules, which encode the binding site from the gp78 ubiquitin ligase that binds to the Ube2G2 ubiquitin conjugating enzyme. The invention further provides isolated G2BD proteins and fusion proteins. Still further provided are diagnostic and therapeutic methods, as well as screening assays utilizing compositions of the invention.

2 Claims, 33 Drawing Sheets

Schematic of gp78/AMFR

OTHER PUBLICATIONS

French et al., "What is a conservative substitution?" J Mol Evol 19:171-175, 1983.*
Database GenEmbl: Search Result 3; Accession No. AR225415; Reed et al., "Compounds for Therapy and Diagnosis of Lung Cancer and Methods for Their Use", US 6,444,425, Sep. 3, 2002; see alignment of search performed on Jun. 16, 2008.
Fang, S. et al. (2001) Proc. Natl. Acad. Sci. USA 98:14422-14427.
Biederer, T. et al. (1997) Science 278:1806-1809.
Tiwari et al., J. Biol Chem. 19:16193-16200 (2001).
Fang, S. et al. (2003) Sem. Cancer Biol. 13:5-14.
Zhong, X. et al. (2004) J. Biol. Chem. 279:45676-45684.
Liang, J.-s. et al. (2003) J. Biol. Chem. 278 23984-23988.

* cited by examiner

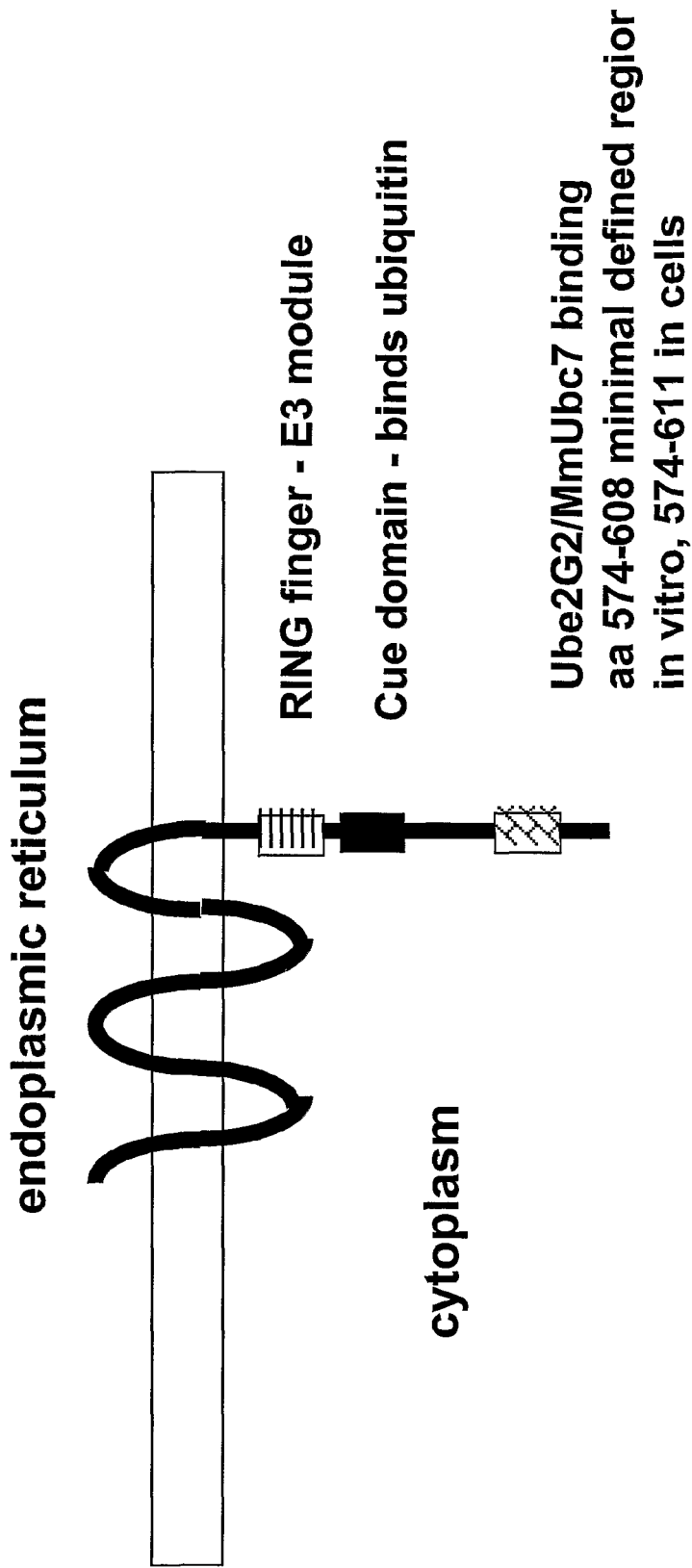
Figure 1. Schematic of gp78/AMFR

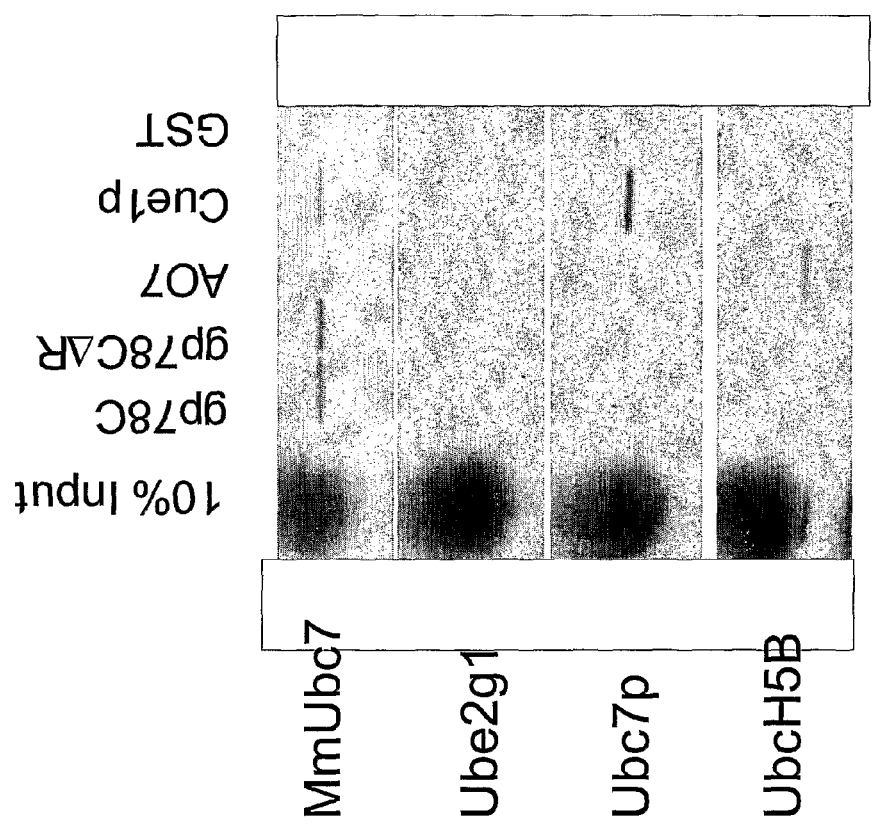
Figure 2. gp78 Selectively Binds MmUBC7/Ube2G2 in GST pull downs

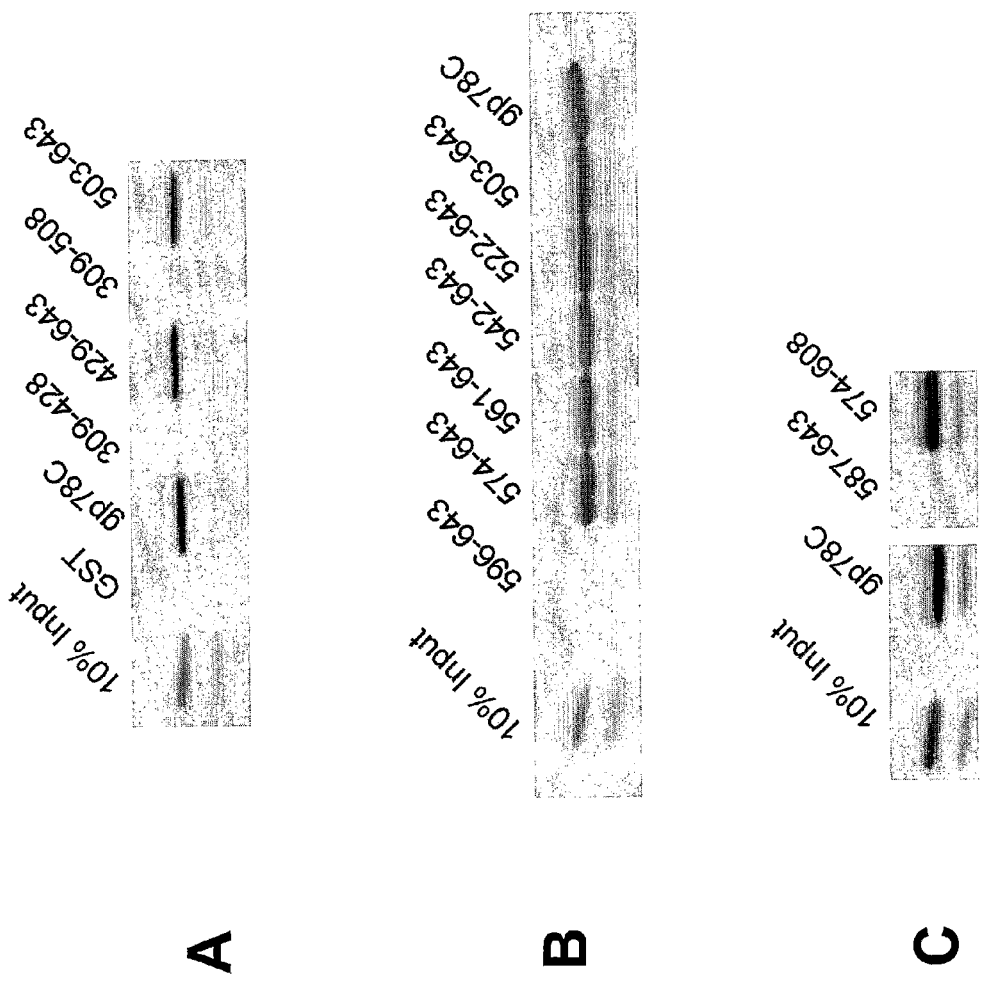
Figure 3 Localizing the Ube2G2/MmUBC7 binding site in vitro

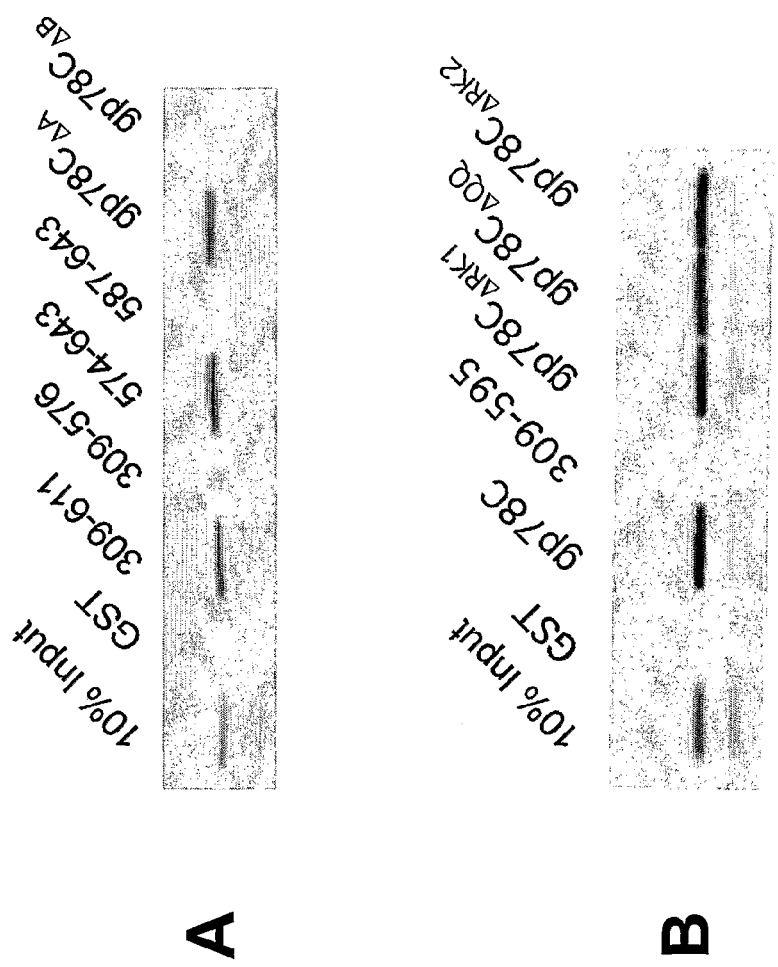
Figure 4 Identifying the Ube2G2/MmUBC7 binding site in vitro

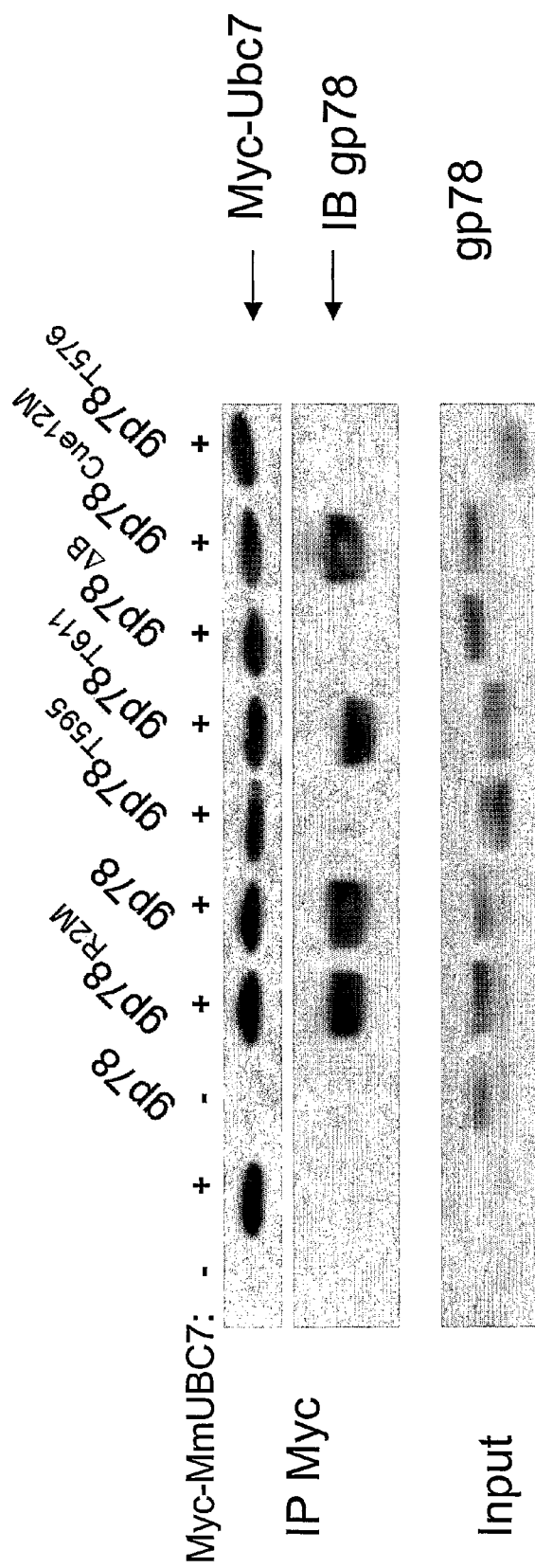
Figure 5 Mapping gp78 Binding to MmUBC7 in cells

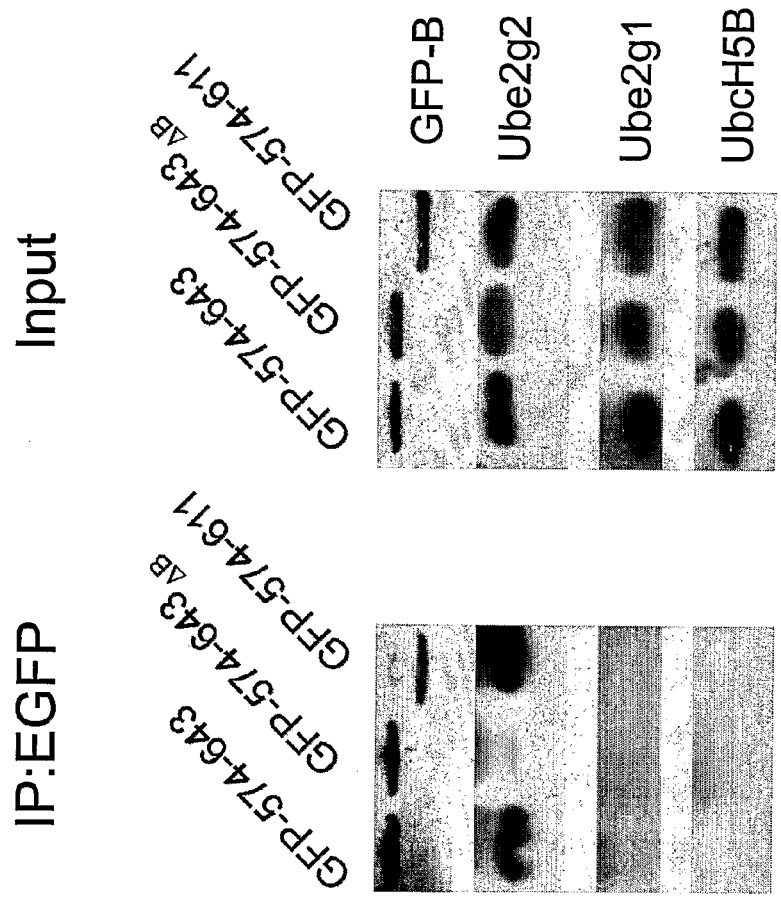
Figure 6 Specific Binding of gp78$_{574-611}$ to Endogenous Ube2G2

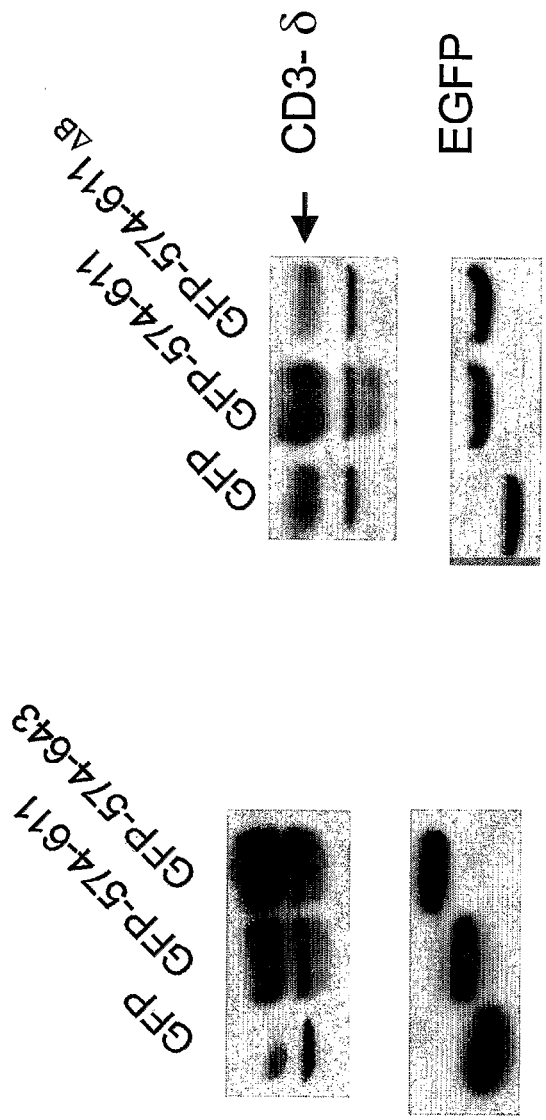
Figure 7. Amino acids 574-611 of gp78 are sufficient to stabilize CD3-δ in cells

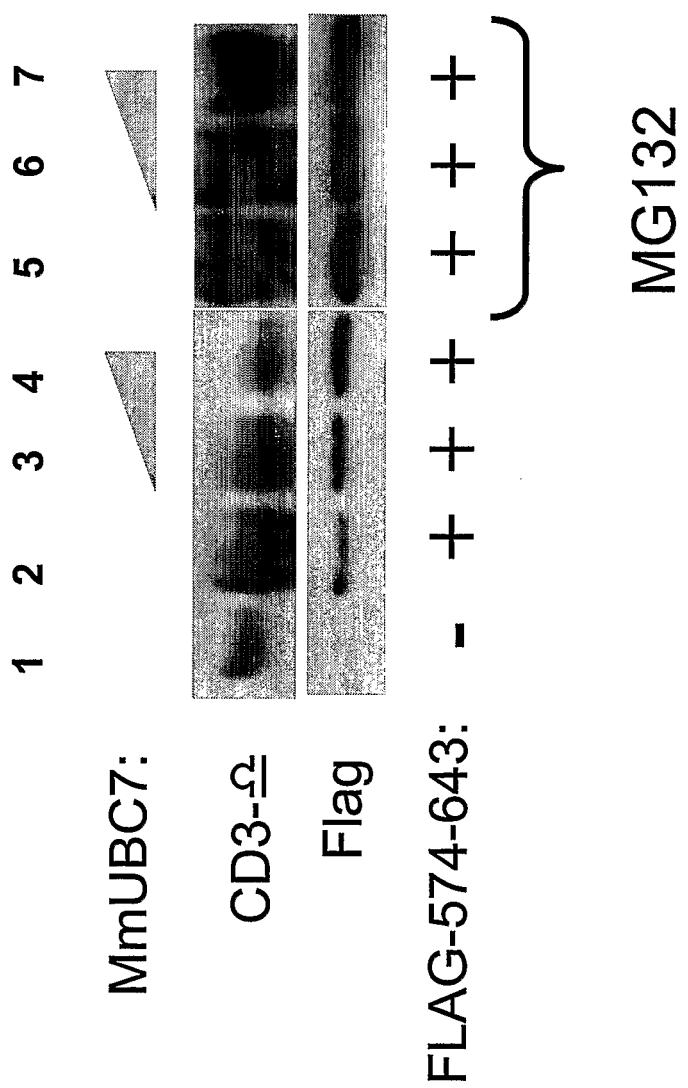
Figure 8. Reversal of CD3-δ stabilization by exogenous MmUBC7

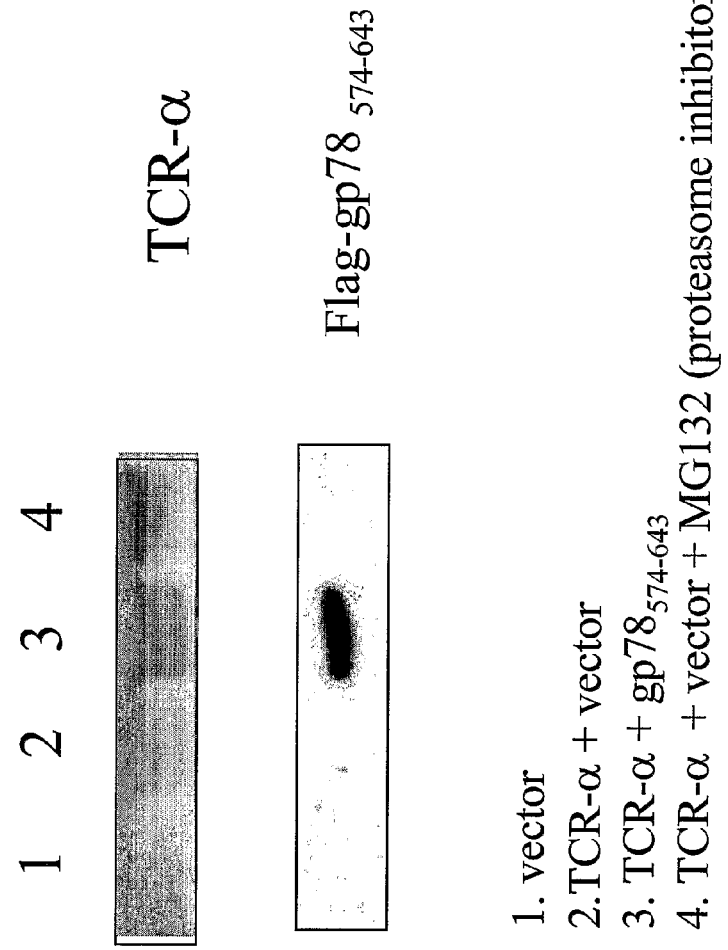
Figure 9. Amino acids 574-643 of gp78 stabilize TCR-α

```
ATGCCGCTGCTCTTCCTCGAGCGCTTCCCCTGGCCCAGCCTCCGCACCTACACGGGCCTCAG
CGGCCTGGCCCTGCTGGGCACCATCATCAGCGCCTACCGCGCGCTCAGCCAGCCCGAGGCCG
GCCCCGGCGAGCCGGACCAGCTAACGGCCTCGCTGCAGCCTGAGCCGCCGGCGCCCGCCCGG
CCGAGCGCCGGGGGACCCCGGGCCCGCGATGTGGCCCAGTACCTGCTCTCAGACAGCCTCTT
CGTGTGGGTTCTAGTAAATACCGCTTGCTGTGTTTTGATGTTGGTGGCTAAGCTCATCCAGT
GTATTGTGTTTGGCCCTCTTCGAGTGAGTGAGAGACAGCATCTCAAAGACAAATTTTGGAAT
TTTATTTTCTACAAGTTCATTTTCATCTTTGGTGTGCTGAATGTCCAGACAGTGGAAGAGGT
GGTCATGTGGTGCCTCTGGTTTGCCGGACTTGTCTTTCTGCACCTGATGGTTCAGCTCTGCA
AGGATCGATTTGAATATCTTTCCTTCTCGCCCACCACGCCGATGAGCAGCCACGGTCGAGTC
CTGTCCCTGTTGGTTGCCATGCTGCTTTCCTGCTGTGGACTGGCGGCCGTCTGCTCCATCAC
CGGCTACACCCACGGAATGCACACCTTGGCTTTCATGGCTGCAGAGTCTCTTCTTGTGACAG
TGAGGACTGCTCATGTGATTTTACGATACGTAATTCACCTCTGGGACCTCAACCACGAAGGG
ACGTGGGAAGGAAAGGGGACGTATGTCTATTACACAGACTTTGTCATGGAGCTCACTCTCCT
GTCCCTGGACCTCATGCACCATATTCACATGTTGTTATTTGGCAACATCTGGTTATCCATGG
CCAGCCTGGTCATCTTTATGCAGCTGCGTTACCTGTTTCATGAGGTGCAACGTCGAATTCGT
CGGCACAAGAACTATCTACGTGTGGTTGGAAACATGGAGGCCAGGTTTGCAGTTGCAACTCC
AGAGGAGCTGGCTGTCAACAATGACGACTGTGCCATCTGTTGGGACTCCATGCAGGCTGCGC
GGAAACTGCCCTGTGGACATCTTTTCCACAACTCCTGTCTTCGTTCCTGGCTAGAACAAGAC
ACCTCCTGTCCAACATGCAGAATGTCTCTTAATATTGCCGACAATAATCGTGTCAGGGAAGA
ACATCAAGGAGAGAACTTGGATGAGAATTTGGTTCCTGTAGCAGCAGCCGAAGGGAGACCTC
GCTTAAACCAACACAATCACTTCTTCCATTTCGATGGGTCTCGGATTGCGAGCTGGCTGCCG
AGTTTTTCGGTTGAAGTGATGCACACCACCAACATTCTTGGCATTACGCAGGCCAGCAACTC
CCAGCTCAATGCAATGGCTCATCAGATTCAAGAGATGTTTCCCCAGGTTCCATACCATCTGG
TACTGCAGGACCTCCAGCTGACACGCTCAGTTGAAATAACAACAGACAATATTTTAGAAGGA
CGGATTCAAGTACCTTTTCCTACACAGCGGTCAGATAGCATCAGACCTGCATTGAACAGTCC
TGTGGAAAGGCCAAGCAGTGACCAGGAAGAGGGAGAAACTTCTGCTCAGACCGAGCGTGTGC
CACTGGACCTCAGTCCTCGCCTGGAGGAGACGCTGGACTTCGGCGAGGTGGAAGTGGAGCCC
AGTGAGGTGGAAGACTTCGAGGCTCGTGGGAGCCGCTTCTCCAAGTCTGCTGATGAGAGACA
GCGCATGCTGGTGCAGCGTAAGGACGAACTCCTCCAGCAAGCTCGCAAACGTTTCTTGAACA
AAAGTTCTGAAGATGATGCGGCCTCAGAGAGCTTCCTCCCCTTGGAAGGTGCGTCCTCTGAC
CCCGTGACCCTGCGTCGAAGGATGCTGGCTGCCGCCGCGGAACGGAGGCTTCAGAAGCAGCA
GACCTCCTAG
```

Fig. 10

MPLLFLERFPWPSLRTYTGLSGLALLGTIISAYRALSQPEAGPGEPDQLTASLQPEPPAPAR
PSAGGPRARDVAQYLLSDSLFVWVLVNTACCVLMLVAKLIQCIVFGPLRVSERQHLKDKFWN
FIFYKFIFIFGVLNVQTVEEVVMWCLWFAGLVFLHLMVQLCKDRFEYLSFSPTTPMSSHGRV
LSLLVAMLLSCCGLAAVCSITGYTHGMHTLAFMAAESLLVTVRTAHVILRYVIHLWDLNHEG
TWEGKGTYVYYTDFVMELTLLSLDLMHHIHMLLFGNIWLSMASLVIFMQLRYLFHEVQRRIR
RHKNYLRVVGNMEARFAVATPEELAVNNDDCAICWDSMQAARKLPCGHLFHNSCLRSWLEQD
TSCPTCRMSLNIADNNRVREEHQGENLDENLVPVAAAEGRPRLNQHNHFFHFDGSRIASWLP
SFSVEVMHTTNILGITQASNSQLNAMAHQIQEMFPQVPYHLVLQDLQLTRSVEITTDNILEG
RIQVPFPTQRSDSIRPALNSPVERPSSDQEEGETSAQTERVPLDLSPRLEETLDFGEVEVEP
SEVEDFEARGSRFSKSADERQRMLVQRKDELLQQARKRFLNKSSEDDAASESFLPLEGASSD
PVTLRRRMLAAAAERRLQKQQTS

Fig. 11

```
GGCACGCGCGCGGCTGAGGCGAGGTCGCTCGGCGCAGCTGTTGCGGGGCCATGGCGGGGACCGCGCTCAA
GAGGCTGATGGCCGAGTACAAACAATTAACACTGAATCCTCCGGAAGGAATTGTAGCAGGCCCCATGAAT
GAAGAGAACTTTTTTGAATGGGAGGCATTGATCATGGGCCCAGAAGACACCTGCTTTGAGTTTGGTGTTT
TTCCTGCCATCCTGAGTTTCCCACTTGATTACCCGTTAAGTCCCCCAAAGATGAGATTTACCTGTGAGAT
GTTTCATCCCAACATCTACCCTGATGGGAGAGTCTGCATTTCCATCCTCCACGCGCCAGGCGATGACCCC
ATGGGCTACGAGAGCAGCGCGGAGCGGTGGAGTCCTGTGCAGAGTGTGGAGAAGATCCTGCTGTCGGTGG
TGAGCATGCTGGCAGAGCCCAATGACGAAAGTGGAGCTAACGTGGATGCGTCCAAAATGTGGCGCGATGA
CCGGGAGCAGTTCTATAAGATTGCCAAGCAGATCGTCCAGAAGTCTCTGGGACTGTGAGACCTGGCCTCG
CACAGGCGCACACACACCGCCAATCAGCTCAGCATTCTCCCCGGCACACTTAGTGACAGTGATGCTCTG
TGCTGGTACCAAACAAGGCAGACTTGCAAGAACCACGGCATCTTTTTTTTTTTTCAAACCTTTCCTACT
TCAAACAGGCTTCTCTTCTGAAATGATGACTTAATGTCGAATATTGACAGCTTACTGCAGTTTTACAGTA
TTCCTCACAAAGGGCTTCAGGTAGATTATCAGAGCTGTCAGCACTACCTCTCCCCGCTGAAACCAGCAGT
TCATGGCTTCCTGTGGATTCCCTCCCTCCCTGGAGTGTTGAGGGGGTTGTACCTGCCAGACTTCCAGGGG
ACGATGGAATACCCAGAACGCTCCTTCTGAAGAAATGGGGCCCTGTAGCTGCAGCACAGGGGAAGGGCCC
GGCACCCTTTCTGGGTCCCTCCTGGTTCCCTGTGGGCCCCATGAGGAGTCCATTACTTCCTTTCTTCCTT
CATATTTTACAGGCAGATGCTTTTCTTATAATCTAATTACATCTTTTCATTTGTTATATATTACAAACCA
TCACACTTAGAAATACTTCCAGGAAATGCTTTTTTGAAGTGTGAATTAATAAGAAATGGGGTAAATAGAA
AAGAAATTTATTGCTGATTGGCCAGGTGCGGTGGTTCGTGCCTGTAATCCCAGCTCTTTGGGAGGCCAAG
GCAGGTAGATCACAAGGTCAGGAAATTGAGACCATCCTGGCTAATACAGTGAAACCCCATGTCTGCTAAA
ATTACAAAAAATTAGCTGGGCGTGGTGGTGCACGCCTGTAGTCTCAGCTACTCAGGAGGCTGAGGCAGGA
GAATCGCTTGAACCCGGGAGGCAGAGGTAGTAGTGAGCTGAAGTCCCGCCACTGCACTCCAGCCTGGGCA
ACAGAGCGAGACTCAGTCTCAAAAAGAAAAAGAAATTTATTGCTGATCACAAGGACAGACAGTTTTTTC
CCGACCATACTCATCAAAGATTTACGTTTGTATATTAGTAACTAGTGCATTACTAGAGCAGGTGCAGGTG
AGGTCTTTAAAGTTTCAATGAAAGTTTCTTCTGGATCTACAGAAAAAAATTTTTTTTTTCAATCTAAAAA
CTGGAAATTCTAGGGTTTTTGTACATTTTGGATGCACTGGGAATTTATTAGCACAAAATCATTCTTTGCA
ACTCAAAATTCAGAAGGGACTCTACCATATCTTAGCTCAGAGCACAGAGGAGTGCCTTATCCCCACACTT
GACTGGGCTGTGGAGGTGGGCATGTGGGCCCCTGGGCCCAGGCTGGGACAGAGCCCTTGTTTTGTGACT
TAGGATTTTGATGTGGTTCCCATGTTCTCTAACAGGGCCAGCTGAGCAGCACAGGCCAGGAGGCCACAGT
GTAAGCAATAACAGATCTGCCACATGCAGAAGCAAATATCAGGCCTGTCGCACACGGGCGGCATTTAAAT
AGGAATTTCTATTTTTGAAATAAGGGATGGTCTATGAGGCATACAGTAGATTTGATGTGATCCTTTTCTC
CCTCCCTTCCATAATGGATCGTGGTCTGTGTGACTGAACCCACACAGAGTGTCATGGGTGACAGTTTCTG
GTTGAAGTAGCTCCACGCTGGGCTTCTGTGGACAGCAGATTCTTTTCCTTCTCACAAGGGGCTCATTTAA
AATTTGGAGGCTGGGTGCTGTGGCTCACGCCTGCAATCCCAGCACTTTGGGAGACTGAGGCGGGCGGATC
ATGAGGTCAGGAGATCGCGACCATCCTGGCTAACAGTGAAACCCTGTCTCCACTAAAAATACAAAAAATT
AGCCGGGCGTGGTGGCGGGCGCCTGTAGTCCCAGCTACTCTGAAGACTGAGGCAGGAGAATGGCGTGAAC
CCAGGAGGCGGAGCTTGCAGTGAGCTGAGATCGCGCCACTGCACTCCAGCCTGGGCAACAGAGTGAGACT
CTGTCTCAAAAAAAAAAAAAAAAAAAAAAAAAAAA
```

Fig. 12

MAGTALKRLMAEYKQLTLNPPEGIVAGPMNEENFFEWEALIMGPEDTCFEFGV
FPAILSFPLDYPLSPPKMRFTCEMFHPNIYPDGRVCISILHAPGDDPMGYESS
AERWSPVQSVEKILLSVVSMLAEPNDESGANVDASKMWRDDREQFYKIAKQIV
QKSLGL

Fig. 13

|  | SEQ ID NO: |
|---|---|
| QRMLVQ | 10 |
| QRMLVQRKDELLQQARKRFLNKSSEDDAAS | 12 |
| QRMLVQRKDELLQQARKRFLNKSSEDDAASESF | 14 |
| SADERQRMLVQRKDELLQQARKRFLNKSSEDDAAS | 16 |
| SADERQRMLVQRKDELLQQARKRFLNKSSEDDAASESF | 18 |
| SADERQRMLVQ | 20 |
| QRMLVQRKDELLQQARKRFLNK | 34 |
| SADERQRMLVQRKDELLQQARKRFLNK | 36 |
| RFLNK | 38 |

Fig. 14

|  | SEQ ID NO: |
|---|---|
| CAGCGCATGCTGGTGCAG | 9 |
| QRMLVQ | 10 |
| CAGCGCATGCTGGTGCAGCGTAAGGACGAACTCCTCCAGC AAGCTCGCAAACGTTTCTTGAACAAAAGTTCTGAAGATGA TGCGGCCTCA | 11 |
| QRMLVQRKDELLQQARKRFLNKSSEDDAAS | 12 |
| CAGCGCATGCTGGTGCAGCGTAAGGACGAACTCCTCCAGC AAGCTCGCAAACGTTTCTTGAACAAAAGTTCTGAAGATGA TGCGGCCTCAGAGAGCTTC | 13 |
| QRMLVQRKDELLQQARKRFLNKSSEDDAASESF | 14 |

Fig. 15A

| | SEQ ID NO: |
|---|---|
| TCTGCTGATGAGAGACAGCGCATGCTGGTGCAGCGTAAGG<br>ACGAACTCCTCCAGCAAGCTCGCAAACGTTTCTTGAACAA<br>AAGTTCTGAAGATGATGCGGCCTCA | 15 |
| SADERQRMLVQRKDELLQQARKRFLNKSSEDDAAS | 16 |
| TCTGCTGATGAGAGACAGCGCATGCTGGTGCAGCGTAAGG<br>ACGAACTCCTCCAGCAAGCTCGCAAACGTTTCTTGAACAA<br>AAGTTCTGAAGATGATGCGGCCTCAGAGAGCTTC | 17 |
| SADERQRMLVQRKDELLQQARKRFLNKSSEDDAASESF | 18 |
| TCTGCTGATGAGAGACAGCGCATGCTGGTGCAG | 19 |
| SADERQRMLVQ | 20 |
| ATTCAAGTACCTTTTCCTACACAGCGGTCAGATAGCATCA<br>GACCTGCATTGAACAGTCCTGTGGAAAGGCCAAGCAGTGA<br>CCAGGAAGAGGGAGAAACTTCTGCTCAGACCGAGCGTGTG<br>CCACTGGACCTCAGTCCTCGCCTGGAGGAGACGCTGGACT<br>TCGGCGAGGTGGAAGTGGAGCCCAGTGAGGTGGAAGACTT<br>CGAGGCTCGTGGGAGCCGCTTCTCCAAGTCTGCTGATGAG<br>AGACAGCGCATGCTGGTGCAG<br><br>IQVPFPTQRSDSIRPALNSPVERPSSDQEEGETSAQTERV<br>PLDLSPRLEETLDFGEVEVEPSEVEDFEARGSRFSKSADE<br>RQRMLVQ | 21<br><br><br><br><br><br><br><br>22 |

Fig. 15B

| | SEQ ID NO: |
|---|---|
| ATTCAAGTACCTTTTCCTACACAGCGGTCAGATAGCATCA<br>GACCTGCATTGAACAGTCCTGTGGAAAGGCCAAGCAGTGA<br>CCAGGAAGAGGGAGAAACTTCTGCTCAGACCGAGCGTGTG<br>CCACTGGACCTCAGTCCTCGCCTGGAGGAGACGCTGGACT<br>TCGGCGAGGTGGAAGTGGAGCCCAGTGAGGTGGAAGACTT<br>CGAGGCTCGTGGGAGCCGCTTCTCCAAGTCTGCTGATGAG<br>AGACAGCGCATGCTGGTGCAGCGTAAGGACGAACTCCTCC<br>AGCAAGCTCGCAAACGTTTCTTGAACAAAAGTTCTGAAGA<br>TGATGCGGCCTCA | 23 |
| IQVPFPTQRSDSIRPALNSPVERPSSDQEEGETSAQTERV<br>PLDLSPRLEETLDFGEVEVEPSEVEDFEARGSRFSKSADE<br>RQRMLVQRKDELLQQARKRFLNKSSEDDAAS | 24 |
| ATTCAAGTACCTTTTCCTACACAGCGGTCAGATAGCATCA<br>GACCTGCATTGAACAGTCCTGTGGAAAGGCCAAGCAGTGA<br>CCAGGAAGAGGGAGAAACTTCTGCTCAGACCGAGCGTGTG<br>CCACTGGACCTCAGTCCTCGCCTGGAGGAGACGCTGGACT<br>TCGGCGAGGTGGAAGTGGAGCCCAGTGAGGTGGAAGACTT<br>CGAGGCTCGTGGGAGCCGCTTCTCCAAGTCTGCTGATGAG<br>AGACAGCGCATGCTGGTGCAGCGTAAGGACGAACTCCTCC<br>AGCAAGCTCGCAAACGTTTCTTGAACAAAAGTTCTGAAGA<br>TGATGCGGCCTCAGAGAGCTTC | 25 |
| IQVPFPTQRSDSIRPALNSPVERPSSDQEEGETSAQTERV<br>PLDLSPRLEETLDFGEVEVEPSEVEDFEARGSRFSKSADE<br>RQRMLVQRKDELLQQARKRFLNKSSEDDAASESF | 26 |

Fig. 15C

| | |
|---|---|
| TCTGCTGATGAGAGACAGCGCATGCTGGTGCAGCGTAAGG<br>ACGAACTCCTCCAGCAAGCTCGCAAACGTTTCTTGAACAA<br>AAGTTCTGAAGATGATGCGGCCTCAGAGAGCTTCCTCCCC<br>TTGGAAGGTGCGTCCTCTGACCCCGTGACCCTGCGTCGAA<br>GGATGCTGGCTGCCGCCGCGGAACGGAGGCTTCAGAAGCA<br>GCAGACCTCC | 27 |
| SADERQRMLVQRKDELLQQARKRFLNKSSEDDAASESFLP<br>LEGASSDPVTLRRRMLAAAAERRLQKQQTS | 28 |
| CAGCGCATGCTGGTGCAGCGTAAGGACGAACTCCTCCAGC<br>AAGCTCGCAAACGTTTCTTGAACAAAAGTTCTGAAGATGA<br>TGCGGCCTCAGAGAGCTTCCTCCCCTTGGAAGGTGCGTCC<br>TCTGACCCCGTGACCCTGCGTCGAAGGATGCTGGCTGCCG<br>CCGCGGAACGGAGGCTTCAGAAGCAGCAGACCTCC | 29 |
| QRMLVQRKDELLQQARKRFLNKSSEDDAASESFLPLEGAS<br>SDPVTLRRRMLAAAAERRLQKQQTS | 30 |

Fig. 15D

| | |
|---|---|
| ATTCAAGTACCTTTTCCTACACAGCGGTCAGATAGCATCA GACCTGCATTGAACAGTCCTGTGGAAAGGCCAAGCAGTGA CCAGGAAGAGGGAGAAACTTCTGCTCAGACCGAGCGTGTG CCACTGGACCTCAGTCCTCGCCTGGAGGAGACGCTGGACT TCGGCGAGGTGGAAGTGGAGCCCAGTGAGGTGGAAGACTT CGAGGCTCGTGGGAGCCGCTTCTCCAAGTCTGCTGATGAG AGACAGCGCATGCTGGTGCAGCGTAAGGACGAACTCCTCC AGCAAGCTCGCAAACGTTTCTTGAACAAAAGTTCTGAAGA TGATGCGGCCTCAGAGAGCTTCCTCCCCTTGGAAGGTGCG TCCTCTGACCCCGTGACCCTGCGTCGAAGGATGCTGGCTG CCGCCGCGGAACGGAGGCTTCAGAAGCAGCAGACCTCC | 31 |
| IQVPFPTQRSDSIRPALNSPVERPSSDQEEGETSAQTERV PLDLSPRLEETLDFGEVEVEPSEVEDFEARGSRFSKSADE RQRMLVQRKDELLQQARKRFLNKSSEDDAASESFLPLEGA SSDPVTLRRRMLAAAAERRLQKQQTS | 32 |
| CAGCGCATGCTGGTGCAGCGTAAGGACGAACTCCTCCAGC AAGCTCGCAAACGTTTCTTGAACAAA | 33 |
| QRMLVQRKDELLQQARKRFLNK | 34 |
| TCTGCTGATGAGAGACAGCGCATGCTGGTGCAGCGTAAGG ACGAACTCCTCCAGCAAGCTCGCAAACGTTTCTTGAACAA A | 35 |
| SADERQRMLVQRKDELLQQARKRFLNK | 36 |

Fig. 15E

| | |
|---|---|
| CGTTTCTTGAACAAA | 37 |
| RFLNK | 38 |
| CCTACACAGCGGTCAGATAGCATCAGACCTGCATTGAACA<br>GTCCTGTGGAAAGGCCAAGCAGTGACCAGGAAGAGGGAGA<br>AACTTCTGCTCAGACCGAGCGTGTGCCACTGGACCTCAGT<br>CCTCGCCTGGAGGAGACGCTGGACTTCGGCGAGGTGGAAG<br>TGGAGCCCAGTGAGGTGGAAGACTTCGAGGCTCGTGGGAG<br>CCGCTTCTCCAAGTCTGCTGATGAGAGACAGCGCATGCTG<br>GTGCAGCGTAAGGACGAACTCCTCCAGCAAGCTCGCAAAC<br>GTTTCTTGAACAAAAGTTCTGAAGATGATGCGGCCTCAGA<br>GAGCTTCCTCCCCTTGGAAGGTGCGTCCTCTGACCCCGTG<br>ACCCTGCGTCGAAGGATGCTGGCTGCCGCCGCGGAACGGA<br>GGCTTCAGAAGCAGCAGACCTCC | 39 |
| PTQRSDSIRPALNSPVERPSSDQEEGETSAQTERVPLDLS<br>PRLEETLDFGEVEVEPSEVEDFEARGSRFSKSADERQRML<br>VQRKDELLQQARKRFLNKSSEDDAASESFLPLEGASSDPV<br>TLRRRMLAAAAERRLQKQQTS | 40 |

Fig. 15F

| | |
|---|---|
| AGCAGTGACCAGGAAGAGGGAGAAACTTCTGCTCAGACCG AGCGTGTGCCACTGGACCTCAGTCCTCGCCTGGAGGAGAC GCTGGACTTCGGCGAGGTGGAAGTGGAGCCCAGTGAGGTG GAAGACTTCGAGGCTCGTGGGAGCCGCTTCTCCAAGTCTG CTGATGAGAGACAGCGCATGCTGGTGCAGCGTAAGGACGA ACTCCTCCAGCAAGCTCGCAAACGTTTCTTGAACAAAAGT TCTGAAGATGATGCGGCCTCAGAGAGCTTCCTCCCCTTGG AAGGTGCGTCCTCTGACCCCGTGACCCTGCGTCGAAGGAT GCTGGCTGCCGCCGCGGAACGGAGGCTTCAGAAGCAGCAG ACCTCC | 41 |
| SSDQEEGETSAQTERVPLDLSPRLEETLDFGEVEVEPSEV EDFEARGSRFSKSADERQRMLVQRKDELLQQARKRFLNKS SEDDAASESFLPLEGASSDPVTLRRRMLAAAAERRLQKQQ TS | 42 |
| AGTCCTCGCCTGGAGGAGACGCTGGACTTCGGCGAGGTGG AAGTGGAGCCCAGTGAGGTGGAAGACTTCGAGGCTCGTGG GAGCCGCTTCTCCAAGTCTGCTGATGAGAGACAGCGCATG CTGGTGCAGCGTAAGGACGAACTCCTCCAGCAAGCTCGCA AACGTTTCTTGAACAAAAGTTCTGAAGATGATGCGGCCTC AGAGAGCTTCCTCCCCTTGGAAGGTGCGTCCTCTGACCCC GTGACCCTGCGTCGAAGGATGCTGGCTGCCGCCGCGGAAC GGAGGCTTCAGAAGCAGCAGACCTCC | 43 |
| SPRLEETLDFGEVEVEPSEVEDFEARGSRFSKSADERQRM LVQRKDELLQQARKRFLNKSSEDDAASESFLPLEGASSDP VTLRRRMLAAAAERRLQKQQTS | 44 |
| GTGGAAGACTTCGAGGCTCGTGGGAGCCGCTTCTCCAAGT CTGCTGATGAGAGACAGCGCATGCTGGTGCAGCGTAAGGA CGAACTCCTCCAGCAAGCTCGCAAACGTTTCTTGAACAAA AGTTCTGAAGATGATGCGGCCTCAGAGAGCTTCCTCCCCT TGGAAGGTGCGTCCTCTGACCCCGTGACCCTGCGTCGAAG GATGCTGGCTGCCGCCGCGGAACGGAGGCTTCAGAAGCAG CAGACCTCC | 45 |
| VEDFEARGSRFSKSADERQRMLVQRKDELLQQARKRFLNK SSEDDAASESFLPLEGASSDPVTLRRRMLAAAAERRLQKQ QTS | 46 |

Fig. 15G

Figure 16
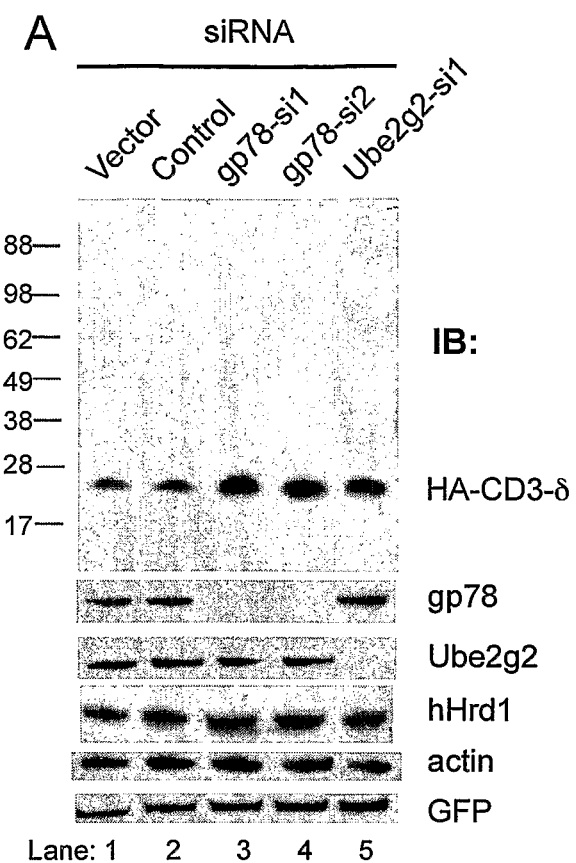
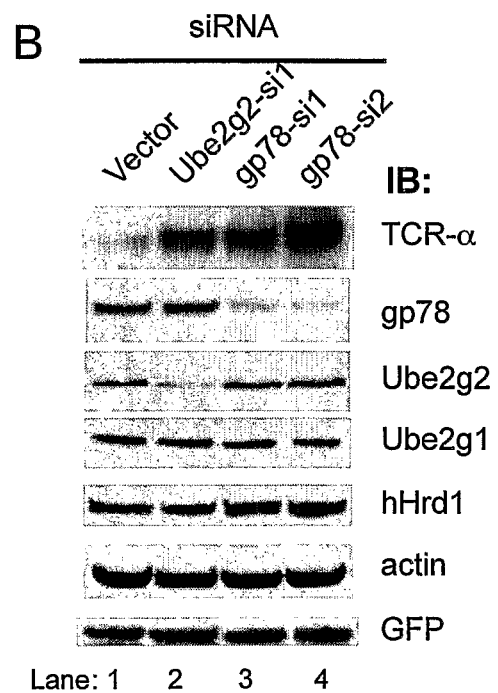

Figure 17
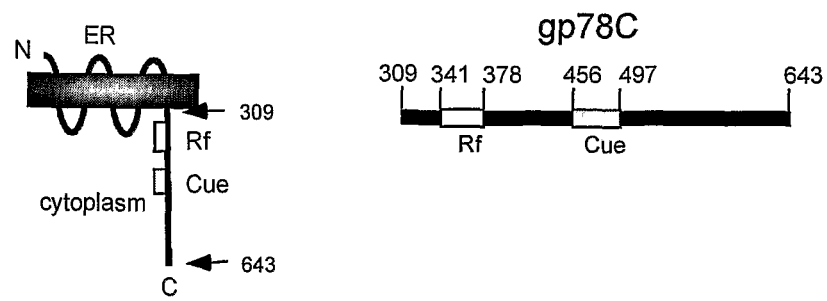
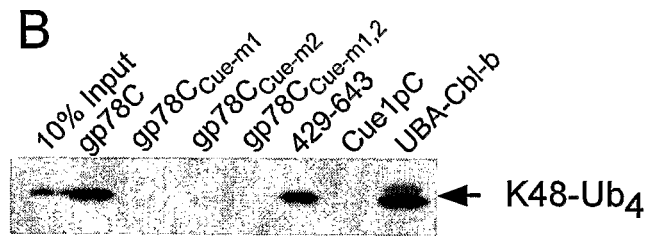
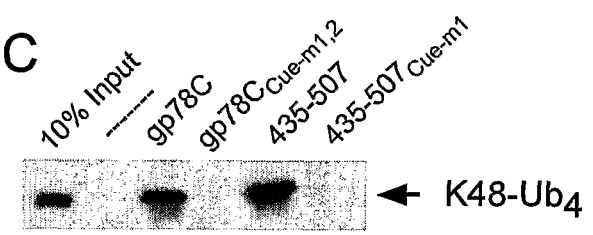

Ube2g2 Binding Site Leads to Loss of GFP Immunoreactiv and CHOP Expression in Human Multiple Myeloma (11,18: light chain  12: heavy chain)

Invasiveness to AMF Correlates with gp78

Fig. 26

SEQUENCE LISTING

```
<160> NUMBER OF SEQ ID NOS: 59

<210> SEQ ID NO 1
<211> LENGTH: 1932
<212> TYPE: DNA
<213> ORGANISM: Homo sapiens

<400> SEQUENCE: 1
atgccgctgc tcttcctcga gcgcttcccc tggcccagcc tccgcaccta cacgggcctc      60
agcggcctgg ccctgctggg caccatcatc agcgcctacc gcgcgctcag ccagcccgag     120 gccgccccg gcgagccgga ccagctaacg gcctcgctgc agcctgagcc gccggcgccc      180
gcccggccga gcgccggggg accccgggcc cgcgatgtgg cccagtacct gctctcagac     240
```

```
agcctcttcg tgtgggttct agtaaatacc gcttgctgtg ttttgatgtt ggtggctaag      300
ctcatccagt gtattgtgtt tggccctctt cgagtgagtg agagacagca tctcaaagac      360
aaattttgga attttatttt ctacaagttc attttcatct ttggtgtgct gaatgtccag      420
acagtggaag aggtggtcat gtggtgcctc tggtttgccg acttgtctt tctgcacctg       480
atggttcagc tctgcaagga tcgatttgaa tatcttcct tctcgcccac cacgccgatg       540
agcagccacg tcgagtcct gtccctgttg gttgccatgc tgctttcctg ctgtggactg       600
gcggccgtct gctccatcac cggctacacc cacggaatgc acccttggc tttcatggct      660
gcagagtctc ttcttgtgac agtgaggact gctcatgtga ttttacgata cgtaattcac      720
ctctgggacc tcaaccacga agggacgtgg aaggaaagg ggacgtatgt ctattacaca       780
gactttgtca tggagctcac tctcctgtcc ctggacctca tgcaccatat tcacatgttg      840
ttatttggca acatctggtt atccatggcc agcctggtca tctttatgca gctgcgttac      900
ctgtttcatg aggtgcaacg tcgaattcgt cggcacaaga actatctacg tgtggttgga      960
aacatggagg ccaggttgc agttgcaact ccagaggagc tggctgtcaa caatgacgac      1020
tgtgccatct gttgggactc catgcaggct gcgcggaaac tgccctgtgg acatctttc      1080
cacaactcct gtcttcgttc ctggctagaa caagacacct cctgtccaac atgcagaatg     1140
tctcttaata ttgccgacaa taatcgtgtc agggaagaac atcaaggaga gaacttggat     1200
gagaatttgg ttcctgtagc agcagccgaa gggagacctc gcttaaacca acacaatcac     1260
ttcttccatt tcgatgggtc tcggattgcg agctggctgc cgagttttc ggttgaagtg      1320
atgcacacca ccaacattct tggcattacg caggccagca actcccagct caatgcaatg     1380
gctcatcaga ttcaagagat gttttccccag gttccatacc atctggtact gcaggacctc    1440
cagctgacac gctcagttga aataacaaca gacaatattt tagaaggacg gattcaagta     1500
ccttttccta cacagcggtc agatagcatc agacctgcat gaacagtcc tgtgaaagg       1560
ccaagcagtg accaggaaga gggagaaact tctgctcaga ccgagcgtgt gccactggac     1620
ctcagtcctc gcctggagga gacgctggac ttcggcgagg tggaagtgga gcccagtgag     1680
gtggaagact cgaggctcg tgggagccgc ttctccaagt ctgctgatga gagacagcgc      1740
atgctggtgc agcgtaagga cgaactcctc cagcaagctc gcaaacgttt cttgaacaaa     1800
agttctgaag atgatgcggc ctcagagagc ttcctcccct tggaaggtgc gtcctctgac     1860
cccgtgaccc tgcgtcgaag gatgctggct gccgccgcgg aacggaggct tcagaagcag     1920
cagacctcct ag                                                         1932

<210> SEQ ID NO 2
<211> LENGTH: 643
<212> TYPE: PRT
<213> ORGANISM: Homo sapiens

<400> SEQUENCE: 2

Met Pro Leu Leu Phe Leu Glu Arg Phe Pro Trp Pro Ser Leu Arg Thr
1               5                   10                  15

Tyr Thr Gly Leu Ser Gly Leu Ala Leu Leu Gly Thr Ile Ile Ser Ala
            20                  25                  30

Tyr Arg Ala Leu Ser Gln Pro Glu Ala Gly Pro Gly Glu Pro Asp Gln
        35                  40                  45

Leu Thr Ala Ser Leu Gln Pro Glu Pro Pro Ala Arg Pro Ser
    50                  55                  60

Ala Gly Gly Pro Arg Ala Arg Asp Val Ala Gln Tyr Leu Leu Ser Asp
65                  70                  75                  80
```

-continued

```
Ser Leu Phe Val Trp Val Leu Val Asn Thr Ala Cys Cys Val Leu Met
                 85                  90                  95
Leu Val Ala Lys Leu Ile Gln Cys Ile Val Phe Gly Pro Leu Arg Val
            100                 105                 110
Ser Glu Arg Gln His Leu Lys Asp Lys Phe Trp Asn Phe Ile Phe Tyr
        115                 120                 125
Lys Phe Ile Phe Ile Phe Gly Val Leu Asn Val Gln Thr Val Glu Glu
130                 135                 140
Val Val Met Trp Cys Leu Trp Phe Ala Gly Leu Val Phe Leu His Leu
145                 150                 155                 160
Met Val Gln Leu Cys Lys Asp Arg Phe Glu Tyr Leu Ser Phe Ser Pro
                165                 170                 175
Thr Thr Pro Met Ser Ser His Gly Arg Val Leu Ser Leu Leu Val Ala
            180                 185                 190
Met Leu Leu Ser Cys Cys Gly Leu Ala Ala Val Cys Ser Ile Thr Gly
        195                 200                 205
Tyr Thr His Gly Met His Thr Leu Ala Phe Met Ala Ala Glu Ser Leu
210                 215                 220
Leu Val Thr Val Arg Thr Ala His Val Ile Leu Arg Tyr Val Ile His
225                 230                 235                 240
Leu Trp Asp Leu Asn His Glu Gly Thr Trp Glu Gly Lys Gly Thr Tyr
                245                 250                 255
Val Tyr Tyr Thr Asp Phe Val Met Glu Leu Thr Leu Leu Ser Leu Asp
            260                 265                 270
Leu Met His His Ile His Met Leu Leu Phe Gly Asn Ile Trp Leu Ser
        275                 280                 285
Met Ala Ser Leu Val Ile Phe Met Gln Leu Arg Tyr Leu Phe His Glu
290                 295                 300
Val Gln Arg Arg Ile Arg Arg His Lys Asn Tyr Leu Arg Val Val Gly
305                 310                 315                 320
Asn Met Glu Ala Arg Phe Ala Val Ala Thr Pro Glu Glu Leu Ala Val
                325                 330                 335
Asn Asn Asp Asp Cys Ala Ile Cys Trp Asp Ser Met Gln Ala Ala Arg
            340                 345                 350
Lys Leu Pro Cys Gly His Leu Phe His Asn Ser Cys Leu Arg Ser Trp
        355                 360                 365
Leu Glu Gln Asp Thr Ser Cys Pro Thr Cys Arg Met Ser Leu Asn Ile
370                 375                 380
Ala Asp Asn Asn Arg Val Arg Glu Glu His Gln Gly Glu Asn Leu Asp
385                 390                 395                 400
Glu Asn Leu Val Pro Val Ala Ala Glu Gly Arg Pro Arg Leu Asn
                405                 410                 415
Gln His Asn His Phe Phe His Phe Asp Gly Ser Arg Ile Ala Ser Trp
            420                 425                 430
Leu Pro Ser Phe Ser Val Glu Val Met His Thr Thr Asn Ile Leu Gly
        435                 440                 445
Ile Thr Gln Ala Ser Asn Ser Gln Leu Asn Ala Met Ala His Gln Ile
450                 455                 460
Gln Glu Met Phe Pro Gln Val Pro Tyr His Leu Val Leu Gln Asp Leu
465                 470                 475                 480
Gln Leu Thr Arg Ser Val Glu Ile Thr Thr Asp Asn Ile Leu Glu Gly
                485                 490                 495
Arg Ile Gln Val Pro Phe Pro Thr Gln Arg Ser Asp Ser Ile Arg Pro
```

```
                    500              505               510
Ala Leu Asn Ser Pro Val Glu Arg Pro Ser Ser Asp Gln Glu Glu Gly
            515                 520                 525

Glu Thr Ser Ala Gln Thr Glu Arg Val Pro Leu Asp Leu Ser Pro Arg
        530                 535                 540

Leu Glu Glu Thr Leu Asp Phe Gly Glu Val Glu Val Glu Pro Ser Glu
545                 550                 555                 560

Val Glu Asp Phe Glu Ala Arg Gly Ser Arg Phe Ser Lys Ser Ala Asp
                565                 570                 575

Glu Arg Gln Arg Met Leu Val Gln Arg Lys Asp Glu Leu Leu Gln Gln
            580                 585                 590

Ala Arg Lys Arg Phe Leu Asn Lys Ser Ser Glu Asp Asp Ala Ala Ser
            595                 600                 605

Glu Ser Phe Leu Pro Leu Glu Gly Ala Ser Ser Asp Pro Val Thr Leu
        610                 615                 620

Arg Arg Arg Met Leu Ala Ala Ala Ala Glu Arg Arg Leu Gln Lys Gln
625                 630                 635                 640

Gln Thr Ser

<210> SEQ ID NO 3
<211> LENGTH: 2555
<212> TYPE: DNA
<213> ORGANISM: Homo sapiens

<400> SEQUENCE: 3
ggcacgcgcg cggctgaggc gaggtcgctc ggcgcagctg ttgcggggcc atggcgggga     60
ccgcgctcaa gaggctgatg gccgagtaca acaattaac actgaatcct ccggaaggaa    120
ttgtagcagg ccccatgaat gaagagaact ttttgaatg ggaggcattg atcatgggcc    180
cagaagacac ctgctttgag tttggtgttt ttcctgccat cctgagtttc ccacttgatt    240
acccgttaag tcccccaaag atgagattta cctgtgagat gtttcatccc aacatctacc    300
ctgatgggag agtctgcatt tccatcctcc acgcgccagg cgatgacccc atgggctacg    360
agagcagcgc ggagcggtgg agtcctgtgc agagtgtgga agatcctg ctgtcggtgg    420 tgagcatgct ggcagagccc aatgacgaaa gtggagctaa cgtggatgcg tccaaaatgt    480
ggcgcgatga ccgggagcag ttctataaga ttgccaagca gatcgtccag aagtctctgg    540
gactgtgaga cctggcctcg cacaggcgca cacaccgc caatcagctc agcattctcc    600
cccggcacac ttagtgacag tgatgctctg tgctggtacc aaacaaggca gacttgcaag    660
aaccacggca tctttttttt tttttcaaac ctttcctact tcaaacaggc ttctcttctg    720
aaatgatgac ttaatgtcga atattgacag cttactgcag ttttacagta ttcctcacaa    780
agggcttcag gtagattatc agagctgtca gcactacctc tccccgctga accagcagt    840 tcatggcttc ctgtggattc cctccctccc tggagtgttg aggggttgt acctgccaga    900 cttccagggg acgatggaat acccagaacg ctccttctga gaaatgggg ccctgtagct    960 gcagcacagg ggaagggccc ggcacccttt ctgggtccct cctggttccc tgtgggcccc   1020
atgaggagtc cattacttcc tttcttcctt catatttac aggcagatgc ttttcttata   1080
atctaattac atcttttcat ttgttatata ttacaaacca tcacacttag aaatacttcc   1140
aggaaatgct tttttgaagt gtgaattaat aagaaatggg gtaaatagaa aagaaattta   1200
ttgctgattg gccaggtgcg gtggttcgtc cctgtaatcc cagctctttg ggaggccaag   1260
gcaggtagat cacaaggtca ggaaattgag accatcctgg ctaatacagt gaaaccccat   1320
```

```
gtctgctaaa attacaaaaa attagctggg cgtggtggtg cacgcctgta gtctcagcta    1380
ctcaggaggc tgaggcagga gaatcgcttg aacccgggag gcagaggtag tagtgagctg    1440
aagtcccgcc actgcactcc agcctgggca acagagcgag actcagtctc aaaagaaaa     1500 aagaaattta ttgctgatca aaggacaga cagttttttc ccgaccatac tcatcaaga     1560 tttacgtttg tatattagta actagtgcat tactagagca ggtgcaggtg aggtctttaa    1620
agtttcaatg aaagtttctt ctggatctac agaaaaaaat tttttttttc aatctaaaaa    1680
ctggaaattc tagggttttt gtacattttg gatgcactgg gaatttatta gcacaaaatc    1740
attctttgca actcaaaatt cagaagggac tctaccatat cttagctcag agcacagagg    1800
agtgccttat ccccacactt gactgggctg tggaggtggg catgtgggcc cctgggccca    1860
ggctggggac agagcccttg ttttgtgact taggattttg atgtggttcc catgttctct    1920
aacagggcca gctgagcagc acaggccagg aggccacagt gtaagcaata acagatctgc    1980
cacatgcaga agcaaatatc aggcctgtcg cacgggcg gcatttaaat aggaatttct     2040 attttttgaaa taagggatgg tctatgaggc atacagtaga tttgatgtga tccttttctc    2100
cctcccttcc ataatggatc gtggtctgtg tgactgaacc cacacagagt gtcatgggtg    2160
acagtttctg gttgaagtag ctccacgctg ggcttctgtg gacagcagat tcttttcctt    2220
ctcacaaggg gctcatttaa aatttggagg ctgggtgctg tggctcacgc ctgcaatccc    2280
agcactttgg gagactgagg cgggcggatc atgaggtcag gagatcgcga ccatcctggc    2340
taacagtgaa accctgtctc cactaaaaat acaaaaaatt agccgggcgt ggtggcgggc    2400
gcctgtagtc ccagctactc tgaagactga ggcaggagaa tggcgtgaac ccaggaggcg    2460
gagcttgcag tgagctgaga tcgcgccact gcactccagc ctgggcaaca gagtgagact    2520
ctgtctcaaa aaaaaaaaaa aaaaaaaaaa aaaaa                               2555
```

<210> SEQ ID NO 4
<211> LENGTH: 165
<212> TYPE: PRT
<213> ORGANISM: Homo sapiens

<400> SEQUENCE: 4

```
Met Ala Gly Thr Ala Leu Lys Arg Leu Met Ala Glu Tyr Lys Gln Leu
1               5                   10                  15

Thr Leu Asn Pro Pro Glu Gly Ile Val Ala Gly Pro Met Asn Glu Glu
            20                  25                  30

Asn Phe Phe Glu Trp Glu Ala Leu Ile Met Gly Pro Glu Asp Thr Cys
        35                  40                  45

Phe Glu Phe Gly Val Phe Pro Ala Ile Leu Ser Phe Pro Leu Asp Tyr
    50                  55                  60

Pro Leu Ser Pro Pro Lys Met Arg Phe Thr Cys Glu Met Phe His Pro
65                  70                  75                  80

Asn Ile Tyr Pro Asp Gly Arg Val Cys Ile Ser Ile Leu His Ala Pro
                85                  90                  95

Gly Asp Asp Pro Met Gly Tyr Glu Ser Ser Ala Glu Arg Trp Ser Pro
            100                 105                 110

Val Gln Ser Val Glu Lys Ile Leu Leu Ser Val Ser Met Leu Ala
        115                 120                 125

Glu Pro Asn Asp Glu Ser Gly Ala Asn Val Asp Ala Ser Lys Met Trp
    130                 135                 140

Arg Asp Asp Arg Glu Gln Phe Tyr Lys Ile Ala Lys Gln Ile Val Gln
145                 150                 155                 160
```

```
Lys Ser Leu Gly Leu
            165

<210> SEQ ID NO 5
<211> LENGTH: 5
<212> TYPE: PRT
<213> ORGANISM: Homo sapiens

<400> SEQUENCE: 5

Ser Ala Asp Glu Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Ala Ala Gly
1               5

<210> SEQ ID NO 7
<211> LENGTH: 6
<212> TYPE: PRT
<213> ORGANISM: Homo sapiens

<400> SEQUENCE: 7

Gln Arg Met Leu Val Gln
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Ala Gly Gly Gly
1               5

<210> SEQ ID NO 9
<211> LENGTH: 18
<212> TYPE: DNA
<213> ORGANISM: Homo sapiens

<400> SEQUENCE: 9
cagcgcatgc tggtgcag                                                 18

<210> SEQ ID NO 10
<211> LENGTH: 6
<212> TYPE: PRT
<213> ORGANISM: Homo sapiens

<400> SEQUENCE: 10

Gln Arg Met Leu Val Gln
1               5

<210> SEQ ID NO 11
<211> LENGTH: 90
<212> TYPE: DNA
<213> ORGANISM: Homo sapiens
```

<400> SEQUENCE: 11
cagcgcatgc tggtgcagcg taaggacgaa ctcctccagc aagctcgcaa acgtttcttg    60
aacaaaagtt ctgaagatga tgcggcctca                                     90

<210> SEQ ID NO 12
<211> LENGTH: 30
<212> TYPE: PRT
<213> ORGANISM: Homo sapiens

<400> SEQUENCE: 12

Gln Arg Met Leu Val Gln Arg Lys Asp Glu Leu Leu Gln Gln Ala Arg
1               5                   10                  15

Lys Arg Phe Leu Asn Lys Ser Ser Glu Asp Asp Ala Ala Ser
            20                  25                  30

<210> SEQ ID NO 13
<211> LENGTH: 99
<212> TYPE: DNA
<213> ORGANISM: Homo sapiens

<400> SEQUENCE: 13
cagcgcatgc tggtgcagcg taaggacgaa ctcctccagc aagctcgcaa acgtttcttg    60
aacaaaagtt ctgaagatga tgcggcctca gagagcttc                           99

<210> SEQ ID NO 14
<211> LENGTH: 33
<212> TYPE: PRT
<213> ORGANISM: Homo sapiens

<400> SEQUENCE: 14

Gln Arg Met Leu Val Gln Arg Lys Asp Glu Leu Leu Gln Gln Ala Arg
1               5                   10                  15

Lys Arg Phe Leu Asn Lys Ser Ser Glu Asp Asp Ala Ala Ser Glu Ser
            20                  25                  30

Phe

<210> SEQ ID NO 15
<211> LENGTH: 105
<212> TYPE: DNA
<213> ORGANISM: Homo sapiens

<400> SEQUENCE: 15
tctgctgatg agagacagcg catgctggtg cagcgtaagg acgaactcct ccagcaagct    60
cgcaaacgtt tcttgaacaa aagttctgaa gatgatgcgg cctca                   105

<210> SEQ ID NO 16
<211> LENGTH: 35
<212> TYPE: PRT
<213> ORGANISM: Homo sapiens

<400> SEQUENCE: 16

Ser Ala Asp Glu Arg Gln Arg Met Leu Val Gln Arg Lys Asp Glu Leu
1               5                   10                  15

Leu Gln Gln Ala Arg Lys Arg Phe Leu Asn Lys Ser Ser Glu Asp Asp
            20                  25                  30

Ala Ala Ser
        35

<210> SEQ ID NO 17
<211> LENGTH: 114

```
<212> TYPE: DNA
<213> ORGANISM: Homo sapiens

<400> SEQUENCE: 17
tctgctgatg agagacagcg catgctggtg cagcgtaagg acgaactcct ccagcaagct    60
cgcaaacgtt tcttgaacaa aagttctgaa gatgatgcgg cctcagagag cttc          114

<210> SEQ ID NO 18
<211> LENGTH: 38
<212> TYPE: PRT
<213> ORGANISM: Homo sapiens

<400> SEQUENCE: 18

Ser Ala Asp Glu Arg Gln Arg Met Leu Val Gln Arg Lys Asp Glu Leu
1               5                   10                  15

Leu Gln Gln Ala Arg Lys Arg Phe Leu Asn Lys Ser Ser Glu Asp Asp
            20                  25                  30

Ala Ala Ser Glu Ser Phe
        35

<210> SEQ ID NO 19
<211> LENGTH: 33
<212> TYPE: DNA
<213> ORGANISM: Homo sapiens

<400> SEQUENCE: 19
tctgctgatg agagacagcg catgctggtg cag                                  33

<210> SEQ ID NO 20
<211> LENGTH: 11
<212> TYPE: PRT
<213> ORGANISM: Homo sapiens

<400> SEQUENCE: 20

Ser Ala Asp Glu Arg Gln Arg Met Leu Val Gln
1               5                   10

<210> SEQ ID NO 21
<211> LENGTH: 261
<212> TYPE: DNA
<213> ORGANISM: Homo sapiens

<400> SEQUENCE: 21
attcaagtac cttttcctac acagcggtca gatagcatca gacctgcatt gaacagtcct    60
gtggaaaggc caagcagtga ccaggaagag ggagaaactt ctgctcagac cgagcgtgtg   120
ccactggacc tcagtcctcg cctggaggag acgctggact cggcgaggt ggaagtggag    180 cccagtgagg tggaagactt cgaggctcgt gggagccgct tctccaagtc tgctgatgag   240
agacagcgca tgctggtgca g                                             261

<210> SEQ ID NO 22
<211> LENGTH: 87
<212> TYPE: PRT
<213> ORGANISM: Homo sapiens

<400> SEQUENCE: 22

Ile Gln Val Pro Phe Pro Thr Gln Arg Ser Asp Ser Ile Arg Pro Ala
1               5                   10                  15

Leu Asn Ser Pro Val Glu Arg Pro Ser Ser Asp Gln Glu Glu Gly Glu
            20                  25                  30

Thr Ser Ala Gln Thr Glu Arg Val Pro Leu Asp Leu Ser Pro Arg Leu
```

```
                35                  40                  45
Glu Glu Thr Leu Asp Phe Gly Glu Val Glu Val Glu Pro Ser Glu Val
    50                  55                  60
Glu Asp Phe Glu Ala Arg Gly Ser Arg Phe Ser Lys Ser Ala Asp Glu
65                  70                  75                  80
Arg Gln Arg Met Leu Val Gln
                85

<210> SEQ ID NO 23
<211> LENGTH: 333
<212> TYPE: DNA
<213> ORGANISM: Homo sapiens

<400> SEQUENCE: 23
attcaagtac cttttcctac acagcggtca gatagcatca gacctgcatt gaacagtcct      60
gtggaaaggc caagcagtga ccaggaagag ggagaaactt ctgctcagac cgagcgtgtg     120
ccactggacc tcagtcctcg cctggaggag acgctggact cggcgaggt  ggaagtggag     180 cccagtgagg tggaagactt cgaggctcgt gggagccgct tctccaagtc tgctgatgag     240
agacagcgca tgctggtgca gcgtaaggac gaactcctcc agcaagctcg caaacgtttc     300
ttgaacaaaa gttctgaaga tgatgcggcc tca                                  333

<210> SEQ ID NO 24
<211> LENGTH: 111
<212> TYPE: PRT
<213> ORGANISM: Homo sapiens

<400> SEQUENCE: 24

Ile Gln Val Pro Phe Pro Thr Gln Arg Ser Asp Ser Ile Arg Pro Ala
1               5                  10                  15
Leu Asn Ser Pro Val Glu Arg Pro Ser Ser Asp Gln Glu Glu Gly Glu
            20                  25                  30
Thr Ser Ala Gln Thr Glu Arg Val Pro Leu Asp Leu Ser Pro Arg Leu
        35                  40                  45
Glu Glu Thr Leu Asp Phe Gly Glu Val Glu Val Glu Pro Ser Glu Val
    50                  55                  60
Glu Asp Phe Glu Ala Arg Gly Ser Arg Phe Ser Lys Ser Ala Asp Glu
65                  70                  75                  80
Arg Gln Arg Met Leu Val Gln Arg Lys Asp Glu Leu Leu Gln Gln Ala
                85                  90                  95
Arg Lys Arg Phe Leu Asn Lys Ser Ser Glu Asp Asp Ala Ala Ser
            100                 105                 110

<210> SEQ ID NO 25
<211> LENGTH: 342
<212> TYPE: DNA
<213> ORGANISM: Homo sapiens

<400> SEQUENCE: 25
attcaagtac cttttcctac acagcggtca gatagcatca gacctgcatt gaacagtcct      60
gtggaaaggc caagcagtga ccaggaagag ggagaaactt ctgctcagac cgagcgtgtg     120
ccactggacc tcagtcctcg cctggaggag acgctggact cggcgaggt  ggaagtggag     180 cccagtgagg tggaagactt cgaggctcgt gggagccgct tctccaagtc tgctgatgag     240
agacagcgca tgctggtgca gcgtaaggac gaactcctcc agcaagctcg caaacgtttc     300
ttgaacaaaa gttctgaaga tgatgcggcc tcagagagct tc                        342
```

```
<210> SEQ ID NO 26
<211> LENGTH: 114
<212> TYPE: PRT
<213> ORGANISM: Homo sapiens

<400> SEQUENCE: 26

Ile Gln Val Pro Phe Pro Thr Gln Arg Ser Asp Ser Ile Arg Pro Ala
1               5                   10                  15

Leu Asn Ser Pro Val Glu Arg Pro Ser Ser Asp Gln Glu Glu Gly Glu
            20                  25                  30

Thr Ser Ala Gln Thr Glu Arg Val Pro Leu Asp Leu Ser Pro Arg Leu
        35                  40                  45

Glu Glu Thr Leu Asp Phe Gly Glu Val Glu Val Glu Pro Ser Glu Val
    50                  55                  60

Glu Asp Phe Glu Ala Arg Gly Ser Arg Phe Ser Lys Ser Ala Asp Glu
65                  70                  75                  80

Arg Gln Arg Met Leu Val Gln Arg Lys Asp Glu Leu Leu Gln Gln Ala
                85                  90                  95

Arg Lys Arg Phe Leu Asn Lys Ser Ser Glu Asp Asp Ala Ala Ser Glu
            100                 105                 110

Ser Phe

<210> SEQ ID NO 27
<211> LENGTH: 210
<212> TYPE: DNA
<213> ORGANISM: Homo sapiens

<400> SEQUENCE: 27
tctgctgatg agagacagcg catgctggtg cagcgtaagg acgaactcct ccagcaagct      60
cgcaaacgtt tcttgaacaa aagttctgaa gatgatgcgg cctcagagag cttcctcccc     120
ttggaaggtg cgtcctctga ccccgtgacc ctgcgtcgaa ggatgctggc tgccgccgcg     180
gaacggaggc ttcagaagca gcagacctcc                                     210

<210> SEQ ID NO 28
<211> LENGTH: 70
<212> TYPE: PRT
<213> ORGANISM: Homo sapiens

<400> SEQUENCE: 28

Ser Ala Asp Glu Arg Gln Arg Met Leu Val Gln Arg Lys Asp Glu Leu
1               5                   10                  15

Leu Gln Gln Ala Arg Lys Arg Phe Leu Asn Lys Ser Ser Glu Asp Asp
            20                  25                  30

Ala Ala Ser Glu Ser Phe Leu Pro Leu Glu Gly Ala Ser Ser Asp Pro
        35                  40                  45

Val Thr Leu Arg Arg Arg Met Leu Ala Ala Ala Glu Arg Arg Leu
    50                  55                  60

Gln Lys Gln Gln Thr Ser
65                  70

<210> SEQ ID NO 29
<211> LENGTH: 195
<212> TYPE: DNA
<213> ORGANISM: Homo sapiens

<400> SEQUENCE: 29
cagcgcatgc tggtgcagcg taaggacgaa ctcctccagc aagctcgcaa acgtttcttg      60
```

```
aacaaaagtt ctgaagatga tgcggcctca gagagcttcc tccccttgga aggtgcgtcc    120
tctgaccccg tgaccctgcg tcgaaggatg ctggctgccg ccgcggaacg gaggcttcag    180
aagcagcaga cctcc                                                    195
```

<210> SEQ ID NO 30
<211> LENGTH: 65
<212> TYPE: PRT
<213> ORGANISM: Homo sapiens

<400> SEQUENCE: 30

```
Gln Arg Met Leu Val Gln Arg Lys Asp Glu Leu Leu Gln Gln Ala Arg
1               5                   10                  15

Lys Arg Phe Leu Asn Lys Ser Ser Glu Asp Asp Ala Ala Ser Glu Ser
            20                  25                  30

Phe Leu Pro Leu Glu Gly Ala Ser Ser Asp Pro Val Thr Leu Arg Arg
        35                  40                  45

Arg Met Leu Ala Ala Ala Ala Glu Arg Arg Leu Gln Lys Gln Gln Thr
    50                  55                  60

Ser
65
```

<210> SEQ ID NO 31
<211> LENGTH: 438
<212> TYPE: DNA
<213> ORGANISM: Homo sapiens

<400> SEQUENCE: 31

```
attcaagtac cttttcctac acagcggtca gatagcatca gacctgcatt gaacagtcct     60
gtggaaaggc caagcagtga ccaggaagag ggagaaactt ctgctcagac cgagcgtgtg    120
ccactggacc tcagtcctcg cctggaggag acgctggact cggcgaggt ggaagtggag    180 cccagtgagg tggaagactt cgaggctcgt gggagccgct ctccaagtc tgctgatgag    240 agacagcgca tgctggtgca gcgtaaggac gaactcctcc agcaagctcg caaacgtttc    300
ttgaacaaaa gttctgaaga tgatgcggcc tcagagagct tcctcccctt ggaaggtgcg    360
tcctctgacc ccgtgaccct gcgtcgaagg atgctggctg ccgccgcgga acggaggctt    420
cagaagcagc agacctcc                                                  438
```

<210> SEQ ID NO 32
<211> LENGTH: 146
<212> TYPE: PRT
<213> ORGANISM: Homo sapiens

<400> SEQUENCE: 32

```
Ile Gln Val Pro Phe Pro Thr Gln Arg Ser Asp Ser Ile Arg Pro Ala
1               5                   10                  15

Leu Asn Ser Pro Val Glu Arg Pro Ser Ser Asp Gln Glu Glu Gly Glu
            20                  25                  30

Thr Ser Ala Gln Thr Glu Arg Val Pro Leu Asp Leu Ser Pro Arg Leu
        35                  40                  45

Glu Glu Thr Leu Asp Phe Gly Glu Val Glu Val Pro Ser Glu Val
    50                  55                  60

Glu Asp Phe Glu Ala Arg Gly Ser Arg Phe Ser Lys Ser Ala Asp Glu
65                  70                  75                  80

Arg Gln Arg Met Leu Val Gln Arg Lys Asp Glu Leu Leu Gln Gln Ala
                85                  90                  95

Arg Lys Arg Phe Leu Asn Lys Ser Ser Glu Asp Asp Ala Ala Ser Glu
```

```
              100                 105                 110
Ser Phe Leu Pro Leu Glu Gly Ala Ser Ser Asp Pro Val Thr Leu Arg
        115                 120                 125

Arg Arg Met Leu Ala Ala Ala Ala Glu Arg Arg Leu Gln Lys Gln Gln
    130                 135                 140

Thr Ser
145
```

<210> SEQ ID NO 33
<211> LENGTH: 66
<212> TYPE: DNA
<213> ORGANISM: Homo sapiens

<400> SEQUENCE: 33
cagcgcatgc tggtgcagcg taaggacgaa ctcctccagc aagctcgcaa acgtttcttg      60
aacaaa                                                                66

<210> SEQ ID NO 34
<211> LENGTH: 22
<212> TYPE: PRT
<213> ORGANISM: Homo sapiens

<400> SEQUENCE: 34

```
Gln Arg Met Leu Val Gln Arg Lys Asp Glu Leu Leu Gln Gln Ala Arg
1               5                   10                  15

Lys Arg Phe Leu Asn Lys
            20
```

<210> SEQ ID NO 35
<211> LENGTH: 81
<212> TYPE: DNA
<213> ORGANISM: Homo sapiens

<400> SEQUENCE: 35
tctgctgatg agagacagcg catgctggtg cagcgtaagg acgaactcct ccagcaagct      60
cgcaaacgtt tcttgaacaa a                                               81

<210> SEQ ID NO 36
<211> LENGTH: 27
<212> TYPE: PRT
<213> ORGANISM: Homo sapiens

<400> SEQUENCE: 36

```
Ser Ala Asp Glu Arg Gln Arg Met Leu Val Gln Arg Lys Asp Glu Leu
1               5                   10                  15

Leu Gln Gln Ala Arg Lys Arg Phe Leu Asn Lys
            20                  25
```

<210> SEQ ID NO 37
<211> LENGTH: 15
<212> TYPE: DNA
<213> ORGANISM: Homo sapiens

<400> SEQUENCE: 37
cgtttcttga acaaa                                                      15

<210> SEQ ID NO 38
<211> LENGTH: 5
<212> TYPE: PRT
<213> ORGANISM: Homo sapiens

<400> SEQUENCE: 38

Arg Phe Leu Asn Lys
1               5

<210> SEQ ID NO 39
<211> LENGTH: 423
<212> TYPE: DNA
<213> ORGANISM: Homo sapiens

<400> SEQUENCE: 39
cctacacagc ggtcagatag catcagacct gcattgaaca gtcctgtgga aaggccaagc      60
agtgaccagg aagagggaga aacttctgct cagaccgagc gtgtgccact ggacctcagt     120
cctcgcctgg aggagacgct ggacttcggc gaggtggaag tggagcccag tgaggtggaa     180
gacttcgagg ctcgtgggag ccgcttctcc aagtctgctg atgagagaca gcgcatgctg     240
gtgcagcgta aggacgaact cctccagcaa gctcgcaaac gtttcttgaa caaaagttct     300
gaagatgatg cggcctcaga gagcttcctc cccttggaag gtgcgtcctc tgaccccgtg     360
accctgcgtc gaaggatgct ggctgccgcc gcggaacgga ggcttcagaa gcagcagacc     420
tcc                                                                   423

<210> SEQ ID NO 40
<211> LENGTH: 141
<212> TYPE: PRT
<213> ORGANISM: Homo sapiens

<400> SEQUENCE: 40

Pro Thr Gln Arg Ser Asp Ser Ile Arg Pro Ala Leu Asn Ser Pro Val
1               5                   10                  15

Glu Arg Pro Ser Ser Asp Gln Glu Gly Glu Thr Ser Ala Gln Thr
            20                  25                  30

Glu Arg Val Pro Leu Asp Leu Ser Pro Arg Leu Glu Glu Thr Leu Asp
        35                  40                  45

Phe Gly Glu Val Glu Val Glu Pro Ser Glu Val Glu Asp Phe Glu Ala
    50                  55                  60

Arg Gly Ser Arg Phe Ser Lys Ser Ala Asp Glu Arg Gln Arg Met Leu
65                  70                  75                  80

Val Gln Arg Lys Asp Glu Leu Leu Gln Gln Ala Arg Lys Arg Phe Leu
                85                  90                  95

Asn Lys Ser Ser Glu Asp Asp Ala Ala Ser Glu Ser Phe Leu Pro Leu
            100                 105                 110

Glu Gly Ala Ser Ser Asp Pro Val Thr Leu Arg Arg Met Leu Ala
        115                 120                 125

Ala Ala Ala Glu Arg Arg Leu Gln Lys Gln Gln Thr Ser
    130                 135                 140

<210> SEQ ID NO 41
<211> LENGTH: 366
<212> TYPE: DNA
<213> ORGANISM: Homo sapiens

<400> SEQUENCE: 41
agcagtgacc aggaagaggg agaaacttct gctcagaccg agcgtgtgcc actggacctc      60
agtcctcgcc tggaggagac gctggacttc ggcgaggtgg aagtggagcc agtgaggtg     120
gaagacttcg aggctcgtgg gagccgcttc tccaagtctg ctgatgagag acagcgcatg     180
ctggtgcagc gtaaggacga actcctccag caagctcgca aacgtttctt gaacaaaagt     240
tctgaagatg atgcggcctc agagagcttc ctcccttgg aaggtgcgtc ctctgacccc     300

```
gtgaccctgc gtcgaaggat gctggctgcc gccgcggaac ggaggcttca gaagcagcag    360
acctcc                                                               366
```

<210> SEQ ID NO 42
<211> LENGTH: 122
<212> TYPE: PRT
<213> ORGANISM: Homo sapiens

<400> SEQUENCE: 42

```
Ser Ser Asp Gln Glu Gly Glu Thr Ser Ala Gln Thr Glu Arg Val
1               5                  10                  15

Pro Leu Asp Leu Ser Pro Arg Leu Glu Glu Thr Leu Asp Phe Gly Glu
            20                  25                  30

Val Glu Val Glu Pro Ser Glu Val Glu Asp Phe Glu Ala Arg Gly Ser
        35                  40                  45

Arg Phe Ser Lys Ser Ala Asp Glu Arg Gln Arg Met Leu Val Gln Arg
    50                  55                  60

Lys Asp Glu Leu Leu Gln Gln Ala Arg Lys Arg Phe Leu Asn Lys Ser
65                  70                  75                  80

Ser Glu Asp Asp Ala Ala Ser Glu Ser Phe Leu Pro Leu Glu Gly Ala
                85                  90                  95

Ser Ser Asp Pro Val Thr Leu Arg Arg Met Leu Ala Ala Ala
            100                 105                 110

Glu Arg Arg Leu Gln Lys Gln Gln Thr Ser
        115                 120
```

<210> SEQ ID NO 43
<211> LENGTH: 306
<212> TYPE: DNA
<213> ORGANISM: Homo sapiens

<400> SEQUENCE: 43

```
agtcctcgcc tggaggagac gctggacttc ggcgaggtgg aagtggagcc cagtgaggtg    60
gaagacttcg aggctcgtgg gagccgcttc tccaagtctg ctgatgagag acagcgcatg   120
ctggtgcagc gtaaggacga actcctccag caagctcgca acgtttctt gaacaaaagt   180 tctgaagatg atgcggcctc agagagcttc ctcccctttgg aaggtgcgtc ctctgacccc   240
gtgaccctgc gtcgaaggat gctggctgcc gccgcggaac ggaggcttca gaagcagcag   300
acctcc                                                              306
```

<210> SEQ ID NO 44
<211> LENGTH: 102
<212> TYPE: PRT
<213> ORGANISM: Homo sapiens

<400> SEQUENCE: 44

```
Ser Pro Arg Leu Glu Glu Thr Leu Asp Phe Gly Glu Val Glu Val Glu
1               5                  10                  15

Pro Ser Glu Val Glu Asp Phe Glu Ala Arg Gly Ser Arg Phe Ser Lys
            20                  25                  30

Ser Ala Asp Glu Arg Gln Arg Met Leu Val Gln Arg Lys Asp Glu Leu
        35                  40                  45

Leu Gln Gln Ala Arg Lys Arg Phe Leu Asn Lys Ser Ser Glu Asp Asp
    50                  55                  60

Ala Ala Ser Glu Ser Phe Leu Pro Leu Glu Gly Ala Ser Ser Asp Pro
65                  70                  75                  80
```

```
Val Thr Leu Arg Arg Arg Met Leu Ala Ala Ala Ala Glu Arg Arg Leu
             85                  90                  95

Gln Lys Gln Gln Thr Ser
            100

<210> SEQ ID NO 45
<211> LENGTH: 249
<212> TYPE: DNA
<213> ORGANISM: Homo sapiens

<400> SEQUENCE: 45
gtggaagact tcgaggctcg tgggagccgc ttctccaagt ctgctgatga gagacagcgc      60
atgctggtgc agcgtaagga cgaactcctc cagcaagctc gcaaacgttt cttgaacaaa     120
agttctgaag atgatgcggc ctcagagagc ttcctcccct tggaaggtgc gtcctctgac     180
cccgtgaccc tgcgtcgaag gatgctggct gccgccgcgg aacggaggct tcagaagcag     240
cagacctcc                                                             249

<210> SEQ ID NO 46
<211> LENGTH: 83
<212> TYPE: PRT
<213> ORGANISM: Homo sapiens

<400> SEQUENCE: 46

Val Glu Asp Phe Glu Ala Arg Gly Ser Arg Phe Ser Lys Ser Ala Asp
1               5                   10                  15

Glu Arg Gln Arg Met Leu Val Gln Arg Lys Asp Glu Leu Leu Gln Gln
            20                  25                  30

Ala Arg Lys Arg Phe Leu Asn Lys Ser Ser Glu Asp Asp Ala Ala Ser
        35                  40                  45

Glu Ser Phe Leu Pro Leu Glu Gly Ala Ser Ser Asp Pro Val Thr Leu
    50                  55                  60

Arg Arg Arg Met Leu Ala Ala Ala Ala Glu Arg Arg Leu Gln Lys Gln
65                  70                  75                  80

Gln Thr Ser

<210> SEQ ID NO 47
<211> LENGTH: 183
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (19)..(168)
<223> OTHER INFORMATION: This region may encompass 0 to 150 nucleotides,
      a, c, g, or t, preferably 33

<400> SEQUENCE: 47
cagcgcatgc tggtgcagnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnncg tttcttgaac     180
aaa                                                                   183

<210> SEQ ID NO 48
<211> LENGTH: 61
<212> TYPE: PRT
<213> ORGANISM: Artificial Sequence
<220> FEATURE:
<223> OTHER INFORMATION: Description of Artificial Sequence: Synthetic
``` consensus sequence
<220> FEATURE:
<221> NAME/KEY: MOD_RES
<222> LOCATION: (7)..(56)
<223> OTHER INFORMATION: Any amino acid; this region may encompass 0 to
      50 residues, preferably 11.

<400> SEQUENCE: 48

Gln Arg Met Leu Val Gln Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Arg Phe Leu Asn Lys
    50                  55                  60

<210> SEQ ID NO 49
<211> LENGTH: 66
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (19)..(27)
<223> OTHER INFORMATION: a, c, g, or t
<220> FEATURE:
<221> NAME/KEY: modified_base
<222> LOCATION: (37)..(42)
<223> OTHER INFORMATION: a, c, g, or t
<220> FEATURE:
<221> NAME/KEY: modified_base
<222> LOCATION: (46)..(51)
<223> OTHER INFORMATION: a, c, g, or t

<400> SEQUENCE: 49
cagcgcatgc tggtgcagnn nnnnnnngaa ctcctcnnnn nngctnnnnn ncgtttcttg     60
aacaaa                                                                66

<210> SEQ ID NO 50
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (16)..(17)
<223> OTHER INFORMATION: Any amino acid

<400> SEQUENCE: 50

Gln Arg Met Leu Val Gln Xaa Xaa Xaa Glu Leu Leu Xaa Xaa Ala Xaa
1               5                   10                  15

Xaa Arg Phe Leu Asn Lys
            20

<210> SEQ ID NO 51
<211> LENGTH: 5

```
<212> TYPE: PRT
<213> ORGANISM: Homo sapiens

<400> SEQUENCE: 51

Val Leu Gln Asp Leu
1               5

<210> SEQ ID NO 52
<211> LENGTH: 5
<212> TYPE: PRT
<213> ORGANISM: Homo sapiens

<400> SEQUENCE: 52

Arg Leu Gln Val Asp
1               5

<210> SEQ ID NO 53
<211> LENGTH: 21
<212> TYPE: PRT
<213> ORGANISM: Saccharomyces cerevisiae

<400> SEQUENCE: 53

Asp Leu Asp Ile Glu Glu Arg Lys Arg Leu Leu Val Trp Gln Ala Arg
1               5                   10                  15

Lys Asn Leu Glu Thr
            20

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Ala Ala Ala Gly Ala Ala Ala Gly Gly Gly Ala Ala Ala
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5

<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (9)..(17)
<223> OTHER INFORMATION: Any amino acid

<400> SEQUENCE: 56

Gln Arg Met Leu Val Gln Ala Ala Xaa Xaa Xaa Xaa Xaa Xaa Xaa Xaa
1               5                   10                  15

Xaa Arg Phe Leu Asn Lys
```

```
<210> SEQ ID NO 57
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (7)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid

<400> SEQUENCE: 57

Gln Arg Met Leu Val Gln Xaa Xaa Xaa Xaa Xaa Xaa Ala Ala Xaa Xaa
1               5                  10                  15

Xaa Arg Phe Leu Asn Lys
            20

<210> SEQ ID NO 58
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (7)..(15)
<223> OTHER INFORMATION: Any amino acid

<400> SEQUENCE: 58

Gln Arg Met Leu Val Gln Xaa Xaa Xaa Xaa Xaa Xaa Xaa Xaa Xaa Ala
1               5                  10                  15

Ala Arg Phe Leu Asn Lys
            20

<210> SEQ ID NO 59
<211> LENGTH: 66
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (12)..(61)
<223> OTHER INFORMATION: Any amino acid; this region may encompass 0 to
      50 residues

<400> SEQUENCE: 59

Ala Ala Ala Ala Gly Gln Arg Met Leu Val Gln Xaa Xaa Xaa Xaa Xaa
1               5                  10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Arg Phe Leu
        50                  55                  60

Asn Lys
65
```

UBE2G2 BINDING DOMAIN IN THE UBIQUITIN LIGASE GP78 AND METHODS OF USE THEREOF

RELATED APPLICATIONS

This application claims the benefit of U.S. Provisional Application Ser. No. 60/583,263, filed on Jun. 26, 2004, the entire contents of which are herein incorporated by this reference.

SEQUENCE LISTING

The instant application contains a Sequence Listing which has been submitted in ASCII format via EFS-Web, and is hereby incorporated by reference in its entirety. Said ASCII copy, created on Sep. 13, 2011, is named 61566US.txt and is 38,613 bytes in size.

BACKGROUND OF THE INVENTION

1. Field of the Invention

The present invention involves the field of ER-associated degradation (ERAD) in cells. More particularly, the present invention involves modulating of the interaction between the ubiquitin ligase gp78 and the ubiquitin conjugating enzyme Ube2G2. The present invention further involves polypepides comprising the Ube2G2 binding domain (G2BD) from gp78, nucleic acid molecules encoding G2BD, and methods of use thereof, including diagnostic and therapeutic methods, as well as screening assays.

2. Background

Cytosolic and nuclear proteins are targeted for proteasomal degradation by the addition of multiubiquitin chains. The specificity of this process is largely conferred by ubiquitin (Ub) protein ligases (E3s). E3s interact directly or indirectly with substrate and mediate transfer of Ub from Ub-conjugating enzymes (E2s) to target proteins where isopeptide linkages are formed. Two major E3 classes have been identified. Homologous to E6-AP C terminus (HECT) domain E3s accept Ub from E2, themselves forming thiol-ester intermediates with Ub. RING finger E3s bind E2 and apparently mediate the direct transfer of Ub from E2 to substrate (reviewed in Hershko, A, & Ciechanover, A. (1998) Annu. Rev. Biochem. 67, 425-479; Joazeiro, C. A. & Weissman, A. M. (2000) Cell 102, 549-552; and Weissman, A. M. (2001) Nat. Rev. Mol. Cell. Biol. 2, 169-178).

Ubiquitylation also plays essential roles in targeting of proteins for retrotranslocation and proteasomal targeting from the endoplasmic reticulum (ER) by processes collectively known as ER-associated degradation (ERAD). ERAD serves to degrade misfolded or otherwise functionally denatured proteins. Elucidation of its details has important implications for many diseases, including cystic fibrosis, neurodegenerative disorders, al antitrypsin deficiency, and tyrosinase deficiency (reviewed in Bonifacino, J. S. & Weissman, A. M. (1998) Annu. Rev. Cell Dev. Biol. 14, 19-57; Plemper, R. K. & Wolf, D. H. (1999) Trends Biochem. Sci. 24, 266-270; and Brodsky, J. L. & McCracken, A. A. (1999) Semin. Cell Dev. Biol. 10, 507-513). Additionally, ERAD has homeostatic functions in regulating hydroxymethylglutaryl-CoA reductase (Hampton, R. Y., Gardner, R. G. & Rine, J. (1996) Mol. Biol. Cell 7, 2029-2044) as well as unassembled, but otherwise apparently native, components of multisubunit cell surface receptors, such as the T cell antigen receptor (TCR) CD3-δ subunit (Yang, M., Omura, S., Bonifacino, J. S. & Weissman, A. M. (1998) J. Exp. Med. 187, 835-846). Ubiquitylation is an obligate step in ERAD that appears to be required for retrotranslocation to the cytosol and proteasomal degradation (Bordallo, J., Plemper, R. K., Finger, A. & Wolf, D. H. (1998) Mol. Biol. Cell 9, 209-222; Yu, H. & Kopito, R. R. (1999) J. Biol. Chem. 274, 36852-36858; Tiwari, S. & Weissman, A. M. (2001) J. Biol. Chem. 276, 16193-16200; Gardner, R. G., Swarbrick, G. M., Bays, N. W., Cronin, S. R., Wilhovsky, S., Seelig, L., Kim, C. & Hampton, R. Y. (2000) J. Cell Biol. 151, 69-82; and references therein). The details by which retrograde movement and proteasomal targeting occur and the means by which Ub is conjugated to sites on proteins that are not normally exposed to the cytosol remain to be fully understood (Bonifacino, J. S. & Weissman, A. M. (1998) Annu. Rev. Cell Dev. Biol. 14, 19-57; McClellan, A. J. & Frydman, J. (2001) Nat. Cell Biol. 3, E51-E53).

Much of what is known about ubiquitylation in ERAD derives from Saccharomyces cerevisiae. Two yeast E2s that associate with the ER, Ubc6p and Ubc7p, play roles in ERAD, with Ubc7p most frequently implicated (Bordallo, J., Plemper, R. K., Finger, A. & Wolf, D. H. (1998) Mol. Biol. Cell 9, 209-222; Gardner, R. G., Swarbrick, G. M., Bays, N. W., Cronin, S. R., Wilhovsky, S., Seelig, L., Kim, C. & Hampton, R. Y. (2000) J. Cell Biol. 151, 69-82; and Sommer, T. & Jentsch, S. (1993) Nature (London) 365, 176-179; and references therein). Ubc6p has a C-terminal hydrophobic anchor that localizes it to the ER membrane (Sommer, T. & Jentsch, S. (1993) Nature (London) 365, 176-179). Ubc7p has no intrinsic characteristics that predict membrane association. The recruitment of Ubc7p to the ER is instead accomplished by association with Cue1p, a small N-terminal anchored ER protein (Biederer, T., Volkwein, C. & Sommer, T. (1997) Science 278, 1806-1809). A single yeast ER resident E3 implicated in ERAD, Hrd1p or Der3p, has been identified. This E3 has the capacity to function with Ubc7p (Hampton, R. Y., Gardner, R. G. & Rine, J. (1996) Mol. Biol. Cell 7, 2029-2044; Bordallo, J., Plemper, R. K., Finger, A. & Wolf, D. H. (1998) Mol. Biol. Cell 9, 209-222; Bays, N. W., Gardner, R. G., Seelig, L. P., Joazeiro, C. A. & Hampton, P Y. (2001) Nat. Cell Biol. 3, 24-29; and Deak, P. M. & Wolf, D. H. (2001) J. Biol. Chem. 276, 10663-10669). The substrates targeted for degradation by this E3 are varied in structure, and there is little evidence of direct E3-substrate binding.

Murine orthologs of Ubc6p and Ubc7p (MmUBC6 and MmUBC7) have been characterized and are highly conserved relative to counterparts in other mammals (Tiwari, S. & Weissman, A. M. (2001) J. Biol. Chem. 276, 16193-16200; Katsanis, N. & Fisher, E. M. (1998) Genomics 51, 128-131; and Lin, H. & Wing, S. S. (1999) J. Biol. Chem. 274, 14685-14691). Of these MmUBC7, but not MrUBC6, is implicated in degradation of unassembled TCR subunits (Tiwari, S. & Weissman, A. M. (2001) J. Biol. Chem. 276, 16193-16200). No mammalian ERAD E3 analogous to yeast Hrd1p/Der3p has been characterized, nor has the existence of a mammalian Cue1p homolog been established.

gp78 was originally isolated as a membrane glycoprotein from murine melanoma cells and was implicated in cell migration (Nabi, I. R. & Raz, A. (1987) Int. J. Cancer 40, 396-402). Subsequently, gp78 was identified as the tumor autocrine motility factor receptor mediating tumor invasion and metastasis (Nabi, I. R., Watanabe, H., Silletti, S. & Raz, A. (1991) EXS 59, 163-177). The message encoding gp78 has recently been shown to be widely expressed in mouse tissues, and perusal of expressed sequence tag databases suggests that this is similarly true for both normal and diseased human tissues (Shimizu, K., Tani, M., Watanabe, H., Nagamachi, Y., Niinaka, Y., Shiroishi, T., Ohwada, S., Raz, A. & Yokota, J.

(1999) FEBS Lett. 456, 295-300). By using a monoclonal antibody, gp78 levels were found to be increased in a number of different human malignancies, with this correlating with metastatic potential. gp78 has been shown to be expressed on the cell surface and to exhibit colocalization with caveolin when endocytosis is arrested, with evidence for internalization and transport to the ER in a manner similar to simian virus 40 (Benlimame, N., Le, P. U. & Nabi, I. R. (1998) Mol. Biol. Cell 9, 1773-1786). Other studies suggest a substantial smooth ER distribution and association with structures that have been referred to as autocrine motility factor receptor tubules (Benlimame, N., Le, P. U. & Nabi, I. R. (1998) Mol. Biol. Cell 9, 1773-1786; Wang, H. J., Benlimame, N. & Nabi, I. (1997) J. Cell Sci. 110, 3043-3053).

Recently, the full-length cDNA for gp78 has been isolated and found to predict a 643-aa protein with at least five membrane-spanning domains (Shimizu, K., Tani, M., Watanabe, H., Nagamachi, Y., Niinaka, Y., Shiroishi, T., Ohwada, S., Raz, A. & Yokota, J. (1999) FEBS Lett. 456, 295-300). Notably, the region C-terminal to the last transmembrane domain includes a RING finger consensus sequence (Shimizu, K., Tani, M., Watanabe, H., Nagamachi, Y., Niinaka, Y., Shiroishi, T., Ohwada, S., Raz, A. & Yokota, J. (1999) FEBS Lett. 456, 295-300). gp78 is largely localized to the ER and has intrinsic RING finger-dependent E3 activity. In this way it can target itself and a heterologous ERAD substrate, CD3-δ, for proteasomal degradation.

Given the importance of gp78 in ERAD and in human disease, there is a need in the art for compositions and methods capable of modulating its activity.

SUMMARY OF THE INVENTION

The present invention is based, at least in part, on the discovery of the binding domain for the ubiquitin conjugating enzyme Ube2G2 in the gp78 ubiquitin ligase protein, referred to interchangeably herein as the "Ube2G2 binding domain", the "Ube2G2/MmrUbc7 binding domain", or "G2BD" nucleic acid and protein molecules. The G2BD nucleic acid and protein molecules of the present invention are useful as modulating agents in regulating a variety of cellular processes, e.g., endoplasmic reticulum (ER) associated degradation (ERAD). Accordingly, in one aspect, this invention provides isolated nucleic acid molecules encoding G2BD proteins or biologically active portions thereof, as well as nucleic acid fragments suitable as primers or hybridization probes for the detection of G2BD-encoding nucleic acids.

In one embodiment, the invention provides a virally encoded or cell permeant version of the G2BD. In one preferred embodiment, a cell permeant version is a peptidomimetic. In another embodiment, a cell-permeant version of G2BD is made by fusing this G2BD to peptides known to traverse the cell membrane. Such G2BD proteins can bind up endogenous Ube2G2 and block ERAD mediated by either gp78 or by other E3s that employee Ube2G2. This may lead to increased cell surface expression of proteins such as CFTR. Thus, the present invention is useful in the treatment of ERAD associated disorders such as cystic fibrosis. A number of viruses degrade MHC class I-encoded molecules and use this as a means to escape immune detection. Similarly, downregulation of MHC class I-encoded proteins represents a mechanism by which tumors escape immune surveillance. This invention may provide a means to increase MHC class I protein expression by preventing degradation of these molecules from the ER prior to their expression on the cell surface. There is also the potential to have roles in a number of other disorders where expression of cell surface receptors or where increased levels of any protein that traverses the secretory pathway is desirable. Non-limiting examples include diabetes and disorders of T cell function.

In adher embodiment, the instant invention provides screening assays useful for identifying specific reagents that block this the G2BD on endogenous gp78 and thereby specifically abrogating the function of this E3—rather than the more general block that can be accomplished by over-expression of the Ube2G2 binding domain itself. Given the role that has been established for gp78 is involved in cell migration and invasion, reagents that block E2 binding and the function of gp78 can potentially suppress cancer invasiveness and metastasis.

In another embodiment, the instant invention provides methods for detecting Ube2G2 (e.g., intracellular levels of Ube2G2), using labeled G2BD as a polypeptide probet. The G2BD has higher affinity for Ube2G2 than known antibodies to Ube2G2.

In another embodiment, the instant invention provides methods for modulating expression of proteins in cells. Expression of secreted proteins may be limited by ERAD. In particular, the production of recombinant antibodies in mammalian cells is an important and growing area in biotechnology. Currently production may be limited for several reasons, such as ER stress-induced toxicity or failure of the antibody to enter the secretion pathway. Strategies that enhance cell viability have shown some success. Alternatively, strategies that reduce ERAD in combination with enhanced chaperone expression have also shown promise. The use of this small fragment that limits ERAD and shows little toxicity has potential applications in these bioproduction schemes.

Other features and advantages of the invention will be apparent from the following detailed description and claims.

BRIEF DESCRIPTION OF THE DRAWINGS

FIG. 1 depicts a schematic representation of gp78/AMFR (SEQ ID NO:2) in the ER membrane. Relative positions of RING finger, Cue domain and Ubc2g2 binding domain (G2BD) are shown. While five transmembrane domains are depicted, the actual number of transmembrane domains is unknown.

FIG. 2 depicts the selective binding of MmUbc7/Ube2G2 to the gp78 cytoplasmic domain in GST pull down assays FIGS. 3A-3C depict the binding of MmUbc7/Ube2G2 deletion mutants to gp78 in GST pull-down assays. Amino acid ranges are relative to SEQ ID NO:2.

FIG. 4A-4B depict binding of MmUbc7/Ube2G2 mutant to gp78 in GST pull-down assays. Amino acid ranges are relative to SEQ ID NO:2. Mutations are represented by Δ and are as follows: ΔRK1: mutated residues 585-586 to AA; ΔQQ: mutated residues 591-592 to AA; ΔRK2: mutated residues 594-595 to AA; ΔA: mutated residues 574-578 (SADER; SEQ ID NO:5) to AAAAG (SEQ ID NO:6); and ΔB: mutated residues 579-584 (QRMLVQ; SEQ ID NO:7) to AAAGGG (SEQ ID NO:8).

FIG. 5 depicts the results of immunoprecipitation of Ube2G2 (MmUbc7) from HEK 293T cells co-transfected with a plasmid encoding myc-tagged MmUbc7/Ube2G2 together with s plasmid encoding various forms of gp78. "R2M" indicates a mutation of two crucial residues in the RING finger. "T" indicates C terminal truncations at the indicated amino acids. ΔB is the mutation indicated above in FIG. 4 in the context of the full length gp78 and "Cue12M" indicates mutations in the Cue domain of gp78. Amino acid ranges are relative to SEQ ID NO:2

FIG. 6 depicts the specific binding of gp78 residues 574-611 to endogenous Ube2G2 in HEK 293T cells.

FIG. 7 depicts the stabilization of CD3-δ protein in cells transfected with the G2BD, but not with the G2BD with amino acids 579-584 (of SEQ ID NO:2) mutated.

FIG. 8 depicts the reversal CD3-δ stabilization by exogenous Ube2G2 (MmUBC7).

FIG. 9 depicts the stabilization of endogenous TCRα by the G2BD.

FIG. 10 depicts the nucleotide sequence of the human gp78 ubiquitin ligase (SEQ ID NO:1). The location of the nucleotides (SEQ ID NO:9 and SEQ ID NO:11) which encode the minimal G2BDs (SEQ ID NO:10 and SEQ ID NO:38, respectively) are shown in bold and with a double underline.

FIG. 11 depicts the amino acid sequence of the human gp78 ubiquitin ligase (SEQ ID NO:2). The minimal G2BDs (SEQ ID NO:10 and SEQ ID NO:38) are shown in bold and with a double underline.

FIG. 12 depicts the nucleotide sequence of the human Ube2G2 ubiquitin conjugating enzyme (SEQ ID NO:3; 100% identical to the mouse MmUbc7).

FIG. 13 depicts the amino acid sequence of the human Ube2G2 ubiquitin conjugating enzyme (SEQ ID NO:4; 100% identical to the mouse MnUbc7).

FIG. 14 depicts an alignment of the G2BD amino acid sequences of SEQ ID NOs:10, 12, 14, 16, 18, 20, 34, 36, and 38. The minimal G2BDs (SEQ ID NO:10 and SEQ ID NO:38) are shown in bold and with a double underline. Amino acids with a single underline can be mutated (as described herein) without affecting G2BD activity.

FIGS. 15A-15G depict the nucleotide and polypeptide sequences of SEQ ID NOs:9-46.

FIGS. 16A-16B depict the essential roles for gp78/AMFR and Ube2G2 in ERAD. (FIG. 16A) HT1080 cells were co-transfected with the indicated siRNA plasmids and HA-tagged CD3-δ. After 48 hours cell lysates were analyzed by immunoblotting (IB) after resolution of equal amounts of lysates on duplicate gels. (FIG. 16B) HEK 293T cells were co-transfected with siRNA plasmids and TCR-α. gp78 and TCR-α were first immunoprecipitated (IP'ed) prior to SDS-PAGE. IP'ed gp78 was detected with biotinylated anti-gp78. TCR-α was IP'ed with A2B4-2 and detected by IB with H28-710. Transfection efficiency was monitored by GFP. Similar results were also obtained for CD3-δ in HEK 293T (not shown).

FIGS. 17A-17C depict the binding of gp78 to tetra-ubiquitin through its Cue domain. (FIG. 17A) Schematic representation of full length gp78 in the ER membrane (left), and of the C-terminal cytoplasmic domain (gp78C) (right) showing the RING finger (Rf) and Cue domain (Cue). Amino acid numbers are relative to SEQ ID NO:2. (FIGS. 17B and 17C). Equi-molar amounts of indicated GST fusions were incubated with lysine 48-linked tetraubiquitin and binding determined by IB with anti-ubiquitin (Ub). gp78CCue-m1 includes the complete C-terminal region of gp78 with a MFP to GGR mutation of residues 467 to 469 (of SEQ ID NO:2). gp78Cuem2 contains a VLQDL (SEQ ID NO:51) to RLQVD (SEQ ID NO:52) mutation of residues 476 to 480 (of SEQ ID NO:2). gp78CCue-m1, 2 contains both sets of mutations. Cue1pC and UBA-Cbl-b correspond to GST fusions of the cytoplasmic domain of Cue1p and the UBA of Cbl-b respectively. Residues 435-507 and 435-507 (of SEQ ID NO:2) Cue-m1 are GST fusions of amino acids 435-507 of gp78 (SEQ ID NO:2) either without or with the Cue-m1 mutation.

(FIG. 18A) At the top is a schematic of the gp78 cytoplasmic domain with a representation of GST fusion proteins tested for Ube2G2 binding and a summary of results at right. Amino acid ranges are relative to SEQ ID NO:2. Below is alignment of the gp78 Ube2G2 binding region (SEQ ID NO:36) with the analogous region of Cue1p (SEQ ID NO:53). Mutations are shown with a summary of results at the bottom. (The 14 mutations in the lefthand box are set forth together as SEQ ID NO:54.) (FIG. 18B) Ube2G2 was translated in reticulocyte lysate and labeled with $^{35}$SMet. The translation product was incubated with indicated GST fusion proteins and assessed for binding. (FIG. 18C) Bacterially expressed His6-Ube2G2 was incubated with the indicated GST fusion proteins followed by immunoblotting with anti-His6. (D) E2s were translated in wheat germ and labeled with $^{35}$S-Met. Equal counts of each were tested for binding to GST fusions proteins. The amount bound in each positive lane is approximately 10% of input (not shown).

(FIG. 19A) Cells were co-transfected with Myc-Ube2G2 and the indicated gp78 mutants. Mutations are identical to those of the GST fusions in FIGS. 17 and 18. Rf-m is an inactivating RING finger mutation. Subscript 576, 595 and 611 are C-terminal truncations after the indicated amino acids of SEQ ID NO:2. Samples were treated with MG132 for 8 hr prior to lysis. IP (upper two panels) with anti-Myc was followed by IB as indicated. Lysate corresponding to 10% of the material used for IP was directly IB'ed for gp78 in the lower panel. (FIG. 19B) HEK 293T were transfected with plasmid encoding N-terminal GFP fusions with the indicated amino acids of gp78. E2-m2 refers to the aforementioned mutation of residues 579 to 584 of SEQ ID NO:2. Anti-GFP IPs (left panel) or whole cell lysates corresponding to approximately 10% of the amount used for IP (right panel) were IB'ed with antibodies raised against different E2s as indicated. (C) Cells were transfected with GFP fusions as in B together with plasmid encoding Myc-tagged Ube2G2 and IP carried out with anti-Myc (upper two panels). Immunoblotting of IPs and whole cell lysate (lower panel) was with either anti-GFP (top and bottom panels) or with anti-Myc (middle panel).

(FIG. 20A) Cells were co-transfected with the indicated forms of full length gp78 together with CD3-δ and lysates analyzed by IB. (B) Cells were transfected with wild type and mutant gp78 plasmids as indicated. Samples were treated with 50 μM MG132 for eight hours, lysates IP'ed with anti-gp78 followed by B3 with either antiubiquitin (upper) or anti-gp78 (lower). Arrow in upper panel indicates migration of unmodified gp78. (FIGS. 20C and 20D) Cells were co-transfected with HA-CD3-δ and wild type (WT) or mutant forms of gp78. Cells were treated with cycloheximide (CHX) as indicated. (FIG. 20E) Graphic representation of CD3-δ levels from FIGS. 20C and 20D (fall length gp78 transfections only), Cue-m1, 2 is the average of data shown in FIGS. 20C and 20D.

(FIGS. 21A and 21B) GFP fusions of the indicated regions of gp78 (SEQ ID NO:2) were co-transfected with CD3-δ followed by IB. (FIG. 21C) Cells transfected with CD3-δ and Mdm2 were co-transfected with Flag-tagged 574 to 643 of gp78 (SEQ ID NO:2) where indicated. In lanes 3 and 6, 2 μg of Ube2G2 plasmid was transfected, in lanes 4 and 7, 4 μg was used. Where indicated, samples were treated with MG132 for eight hours prior to lysis. (FIG. 21D) Cells were co-transfected with TCR-α and GFP fusions of gp78 and treated with MG132 where indicated.

(FIG. 22A) NIH 3T3 cells were transfected with plasmid encoding GFP fusions and IB'ed as indicated. (FIG. 22B) J558 cells expressing the indicated GFP fusions were obtained by cell sorting and cell lysates IB'ed. (FIG. 22C) J558 cells were transfected and lysates from cells harvested at indicated times IB'ed for GFP. (D) J558 cells and NIH 3T3 cells were transfected with plasmids as indicated and GFP positive cells assayed for annexin V binding by FACS 24 hours following transfection as an indicator of apoptosis.

FIG. 26 depicts the correlation between invasiveness to AMF and gp78.

DETAILED DESCRIPTION OF THE INVENTION

Figure 18:
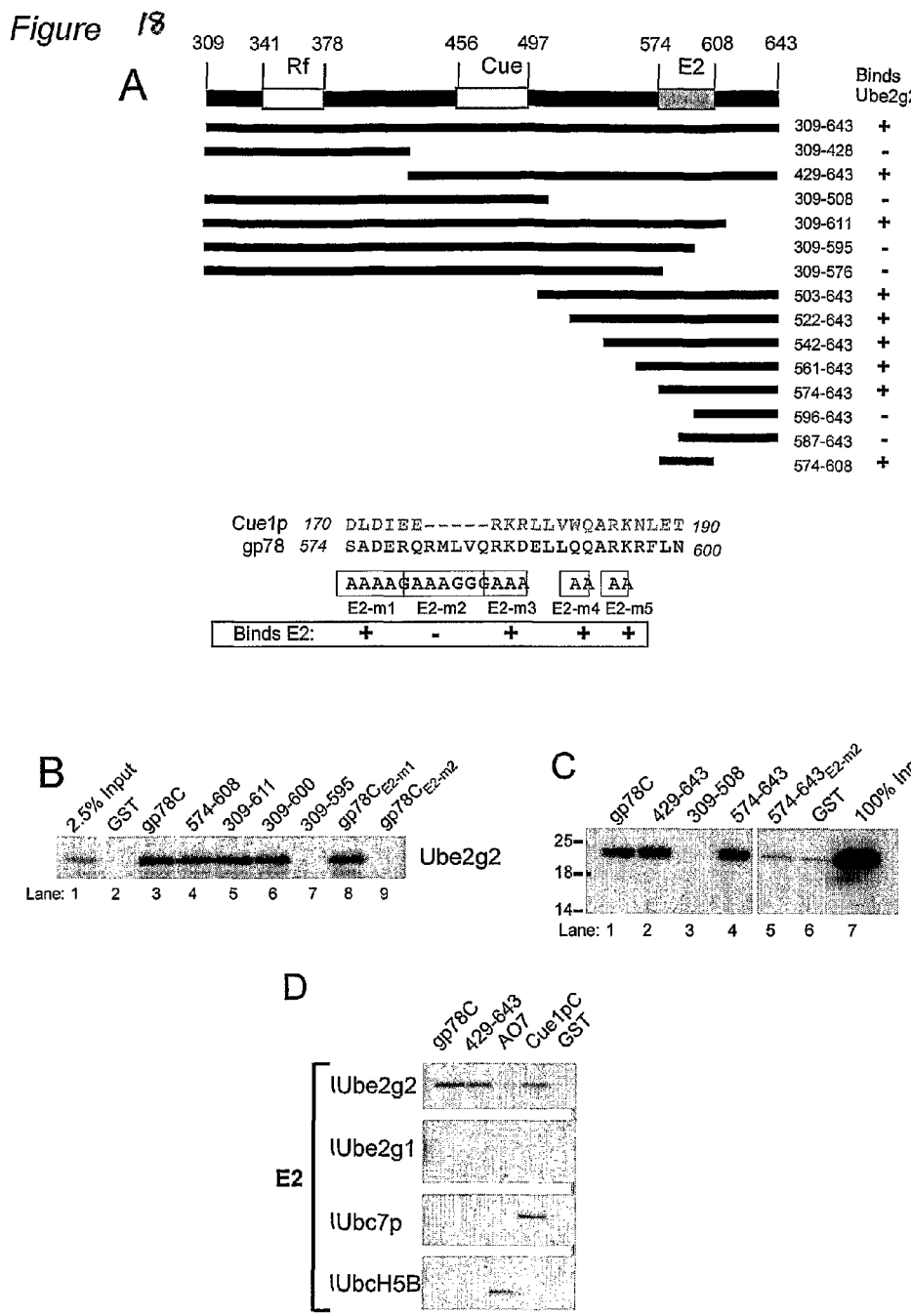
FIGS. 18A-18C depict the localization and specificity of Ube2G2 binding to gp78.

The present invention is based, at least in part, on the discovery of the binding domain for the ubiqutin conjugating enzyme Ube2G2 in the gp78 ubiqutin ligase protein, referred to interchangeably herein as the "Ube2G2 binding domain", the "Ube2G2/MmUbc7 binding domain", "Ube2G2 binding site", or "G2BD" nucleic acid and protein molecules. The G2BD nucleic acid and protein molecules of the present invention are useful as modulating agents in regulating a variety of cellular processes, e.g., endoplasmic reticulum (ER) associated degradation (ERAD). Accordingly, in one aspect, this invention provides isolated nucleic acid molecules encoding G2BD proteins or biologically active portions thereof, as well as methods of identifying compounds useful for modulating ERAD and/or treating ERAD-associated diseases and disorders.

gp78, also referred to herein as the "or autocrine motility factor receptor" or "AMFR") was originally isolated as a membrane glycoprotein from murine melanoma cells and was implicated in cell migration (Nabi, I. R. & Raz, A. (1987) Int. J. Cancer 40, 396-402). Subsequently, gp78 was identified as the tumor autocrine motility factor receptor mediating tumor invasion and metastasis (Nabi, I. R., Watanabe, H., Silletti, S. & Raz, A. (1991) EXS 59, 163-177). The message encoding gp78 has recently been shown to be widely expressed in mouse tissues, and perusal of expressed sequence tag databases suggests that this is similarly true for both normal and diseased human tissues (Shimizu, K., Tani, M., Watanabe, H., Nagamachi, Y., Niinaka, Y., Shiroishi, T., Ohwada, S., Raz, A. & Yokota, J. (1999) FEBS Lett. 456, 295-300). By using a monoclonal antibody, gp78 levels were found to be increased in a number of different human malignancies, with this correlating with metastatic potential. gp78 has been shown to be expressed on the cell surface and to exhibit colocalization with caveolin when endocytosis is arrested, with evidence for internalization and transport to the ER in a manner similar to simian virus 40 (Benlimame, N., Le, P. U. & Nabi, I. R. (1998) Mol. Biol. Cell 9, 1773-1786). Other studies suggest a substantial smooth ER distribution and association with structures that have been referred to as autocrine motility factor receptor tubules (Benlimame, N., Le, P. U. & Nabi, I. R. (1998) Mol. Biol. Cell 9, 1773-1786; Wang, H. J., Benlimame, N. & Nabi, I. (1997) J. Cell Sci. 110, 3043-3053).

The data presented herein identifies a region in the gp78 protein (SEQ ID NO:2, GenBank Accession No. NP_001135, and FIG. 11; encoded by the nucleic acid sequence of SEQ ID NO:1, GenBank Accession No. NM_001144, and FIG. 10) that binds to the human ubiquitin conjugating enzyme Ube2G2 (SEQ ID NO:4, GenBank Accession No. BC001738, FIG. 13, SEQ ID NO:4; encoded by the nucleic acid sequence of SEQ ID NO:3), and shows that over-expression of this region confers an inhibitory effect on ERAD, which results in the stabilization of cellular proteins that are degraded by ERAD. Expression of this region in cells blocks ERAD by binding to endogenous Ube2G2. Mutation of a minimal regions required for Ube2G2 binding (described in greater detail below) in the full-length gp78 blocks its ability to function as an E3 in targeting proteins for degradation in the endoplasmic reticulum. The discoveries of the instant invention represent the first identification of a binding site for an E2 (UbeG2) on an E3 protein (gp78) in mammalian cells. The binding of UbeG2 to the G2BD of gp78 is highly specific; no other E2 proteins bound specifically to the gp78 G2BD.

The amino acid sequence of human Ube2G2 is 100% identical to the mouse protein MmUbc7 (GenBank Accession No. NM_019803). Accordingly, these two proteins may be referred to interchangeably herein. The region of gp78 that binds to Ube2G2 is referred to herein as the Ube2G2 binding domain, or "G2BD".

Accordingly, the G2BD molecules of the present invention provide novel diagnostic targets and therapeutic agents for ERAD associated disorders. As used herein, the term "ERAD associated disorder" includes a disorder, disease or condition which is caused, affected, and/or associated with ERAD. ERAD associated disorders can detrimentally affect cellular functions associated with up- or downregulation of protein stability (e.g., the stability of a particular protein, such as the TCR, or of proteins in general). ERAD associated disorders also include disorders where up- or downregulation of protein stability may be beneficial in treating the disorder. Examples of BRAD associated disorders include disorders of cholesterol and/or triglyceride metabolism, cystic fibrosis, Parkinson's disease, prion diseases of humans or animals, and/or viral infections (e.g., human cytomegalovirus (CMV), or human immunodeficiency virus (HIV)).

The G2BD molecules of the present invention further provide novel diagnostic targets and therapeutic agents for cellular proliferation, growth, or differentiation disorders. Cellular proliferation, growth, or differentiation disorders include those disorders that affect cell proliferation, growth, or differentiation processes. As used herein, a "cellular proliferation, growth, or differentiation process" is a process by which a cell increases in number, size or content, or by which a cell develops a specialized set of characteristics which differ from that of other cells. In particular, ERAD is known to be involved in regulating tumor invasiveness and metastasis, indicating that the G2BD molecules of the present invention are useful in modulating invasiveness and metastasis. Such disorders include cancer, e.g., carcinoma, sarcoma, or leukemia; tumor angiogenesis and metastasis; skeletal dysplasia; hepatic disorders; myelodysplastic syndromes; and hematopoietic and/or myeloproliferative disorders. Particularly preferred disorders include melanoma and multiple myeloma.

Additional disorders that may be treated using the molecules of the present invention include disorders affecting any tissues in which Ube2G2 protein is expressed.

The term "family" when referring to the protein and nucleic acid molecules of the present invention is intended to mean two or more proteins or nucleic acid molecules having a common structural domain or motif and having sufficient amino acid or nucleotide sequence identity as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics.

For example, a G2BD protein of the present invention is at least about 6-146 amino acid residues and has an "G2BD activity", for example, the ability to interact with Ube2G2; to modulate Ube2G2 activity, to modulate ERAD; to modulate intra- or inter-cellular signaling and/or gene transcription (e.g., either directly or indirectly); and/or to modulate protein stability. Accordingly, identifying the presence of G2BD can include isolating a fragment of a G2BD molecule (e.g., a G2BD polypeptide) and assaying for the ability of the fragment to exhibit one of the aforementioned G2BD activities. Preferably, a G2BD protein of the present invention does not contain amino acid sequences that are not derived from the cytoplasmic domain of gp78 (i.e., preferably, a G2BD protein does not contain amino acid sequences from residues 1-308 of SEQ ID NO:2). Even more preferably, a G2BD protein of the present invention does not contain amino acid sequences from the gp78 RING finger domain or any amino acid residues N-terminal to the RING finger domain (i.e., preferably, a G2BD protein does not contain amino acid sequences from residues 1-428 of SEQ ID NO:2). Even more preferably, a G2BD protein does not contain amino acid sequences from the gp78 CUE domain or any amino acid residues N-terminal to the CUE domain (i.e., preferably, a G2BD protein does not contain amino acid sequences from residues 1-497 of SEQ ID NO:2). Preferably, a G2BD protein is about 6-146, 6-140, 6-120, 6-100, 6-80, 6-60, or 6-40 amino acid residues and has a G2BD activity. More preferably, a G2BD is about 38, 35, 33, 30, 11, 6, or 5 amino acids residues and has a G2BD activity. Most preferably, a G2BD is about 22 amino acid residues.

In a preferred embodiment, a G2BD comprises the amino acid sequence QRMLVQ (residues 579-584 of SEQ ID NO:2, set forth as SEQ ID NO:10, encoded by SEQ ID NO:9). This six-amino acid sequence, referred to herein as an "N-terminal minimal G2BD", is required for binding to Ube2G2. When mutated (see FIG. 4), a G2BD protein no longer binds to Ube2G2. In another preferred embodiment, a G2BD comprises the amino acid sequence RFLNK (residues 596-600 of SEQ ID NO:2, set forth as SEQ ID NO:38, encoded by SEQ ID NO:37). This five-amino acid sequence, referred to herein as a "C-terminal minimal G2BD, is also required for binding to Ube2G2. When mutated, a G2BD protein no longer binds to Ube2G2.

In another preferred embodiment, a G2BD comprises amino acid residues 579-608 of SEQ ID NO:2 (set forth as SEQ ID NO: 12, encoded by SEQ ID NO: 11). In another preferred embodiment, a G2BD comprises amino acid residues 579-611 of SEQ ID NO:2 (set forth as SEQ ID NO:14, encoded by SEQ ID NO:13). In another preferred embodiment, a G2BD comprises amino acid sequence 574-608 of SEQ ID NO:2 (set forth as SEQ ID NO: 16, encoded by SEQ ID NO: 15). In another preferred embodiment, a G2BD comprises amino acid residues 574-611 of SEQ ID NO:2 (set forth as SEQ ID NO:18, encoded by SEQ ID NO: 17). In another preferred embodiment, a G2BD comprises amino acid residues 574-584 of SEQ ID NO:2 (set forth as SEQ ID NO:20, encoded by SEQ ID NO: 19). In another preferred embodiment, a G2BD comprises amino acid residues 579-600 of SEQ ID NO:2 (set forth as SEQ ID NO:34, encoded by SEQ ID NO:33). In another preferred embodiment, a G2BD amino acid residues 574-600 of SEQ ID NO:2 (set forth as SEQ ID NO:36, encoded by SEQ ID NO:35). An alignment of the amino acid sequences of SEQ ID NOs:10, 12, 14, 16, 18, 20, 34, 36, and 38 is presented in FIG. 14.

In another preferred embodiment, a G2BD comprises amino acid residues 498-584 of SEQ ID NO:2 (set forth as SEQ ID NO:22, encoded by SEQ ID NO:21). In another preferred embodiment, a G2BD comprises amino acid residues 498-608 of SEQ ID NO:2 (set forth as SEQ ID NO:24, encoded by SEQ ID NO:23). In another preferred embodiment, a G2BD comprises amino acid residues 498-611 of SEQ ID NO:2 (set forth as SEQ ID NO:26, encoded by SEQ ID NO:25). In another preferred embodiment, a G2BD comprises amino acid residues 574-643 of SEQ ID NO:2 (set forth as SEQ ID NO:28, encoded by SEQ ID NO:27). In another preferred embodiment, a G2BD comprises amino acid residues 579-643 of SEQ ID NO:2 (set forth as SEQ ID NO:30, encoded by SEQ ID NO:29). In still another preferred embodiment, a G2BD comprises amino acid residues 498-643 of SEQ ID NO:2 (set forth as SEQ ID NO:32, encoded by SEQ ID NO:31). In another preferred embodiment, a G2BD comprises amino acid residues 503-643 of SEQ ID NO:2 (set forth as SEQ ID NO:40, encoded by SEQ ID NO:39). In another preferred embodiment, a G2BD comprises amino acid residues 522-643 of SEQ ID NO:2 (set forth as SEQ ID NO:42, encoded by SEQ ID NO:41). In another preferred embodiment, a G2BD comprises amino acid residues 542-643 of SEQ ID NO:2 (set forth as SEQ ID NO:44, encoded by SEQ ID NO:43). In another preferred embodiment, a G2BD comprises amino acid residues 561-643 of SEQ ID NO:2 (set forth as SEQ ID NO:46, encoded by SEQ ID NO:45).

The nucleotide and polypeptide sequences of SEQ ID NOs:9-46 are shown in FIGS. 15A-15G.

In further embodiments, a preferred G2BD is mutated. For example, in one embodiment, residues 585-586 of SEQ ID NO:2 (or the corresponding RK residues in any of the G2BD proteins of the invention) are mutated to alanines (AA). Such a mutant is still capable of binding to Ube2G2. In another embodiment, residues 591-592 of SEQ ID NO:2 (or the corresponding QQ residues in any of the G2BD proteins of the invention) are mutated to alanines (AA). Such a mutant is still capable of binding to Ube2G2. In another embodiment, residues 594-595 of SEQ ID NO:2 (or the corresponding RK residues in any of the G2BD proteins of the invention) are mutated to alanines (AA). Such a mutant is still capable of binding to Ube2G2. In another embodiment, residues 574-578 of SEQ ID NO:2 (or the corresponding SADER (SEQ ID NO:5) residues in any of the G2BD proteins of the invention) are mutated to AAAAG (SEQ ID NO:6). Such a mutant is still capable of binding to Ube2G2. In still another embodiment, residues 579-584 of SEQ ID NO:2 (or the corresponding QRMLVQ (SEQ ID NO:10) residues in any of the G2BD proteins of the invention) are mutated to AAAGGG (SEQ ID NO:8). Such a mutant does not bind to Ube2G2.

In a further embodiment, a G2BD comprises the consensus sequence Q-R-M-L-V-Q-$X_n$-R-F-L-N-K (SEQ ID NO:48), wherein X is any amino acid residue, and n is any number from 0-50, from 0-40, from 0-30, from 0-20, from 0-15, or from 0-11 amino acid residues. Preferably, n is 11 amino acid residues. For example, $X_1$ indicates one amino acid reside, $X_2$ indicates two amino acid resides, etc. The consensus amino acid sequence of SEQ ID NO:48 is encoded by the consensus nucleotide sequence CAGCGCATGCTGGTGCAG-N$_y$-CGTTTCTTGAACAAA (SEQ ID NO:47), wherein N is any nucleotide, and y is any number from 0-150, from 0-120, from 0-90, from 0-60, from 0-45, or from 0-33 nucleotides. For example, N$_1$, indicates one nucleotide, N$_2$ indicates two nucleotides, etc. Preferably, y is 33 nucleotides.

In another embodiment, a G2BD comprises the consensus sequence Q-R-M-LV-Q-X-X-X-E-L-L-X-X-A-X-X-R-F-L-N-K (SEQ ID NO:50), wherein X is any amino acid residue. The consensus amino acid sequence of SEQ ID NO:50 is encoded by the nuclotide sequence CAGCGCATGCTGGT-GCAG-NNNNNNNNN-GAACTCCTC-NNNNNN-GCT-NNNNNN-CGTTTCTTGAACAAA (SEQ ID NO:49), wherein N is any nucleotide. In a preferred embodiment, a G2BD comprises the sequence SEQ ID NO:33.

Isolated G2BD proteins of the present invention have an amino acid sequence sufficiently identical to the amino acid sequence of SEQ ID NO:10, 12, 14, 16, 18, 20, 22, 24, 26, 28, 30, 32, 34, 36, 38, 40, 42, 44, 46, 48, or 50, or are encoded by a nucleotide sequence sufficiently identical to SEQ ID NO:9, 11, 13, 15, 17, 19, 21, 23, 25, 27, 29, 31, 33, 35, 37, 39, 41, 43, 45, 47, or 49. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more homology or identity across the amino acid sequences of the domains and contain at least one and preferably two structural domains or motifs, are defined herein as sufficiently identical. Furthermore, amino acid or nucleotide sequences which share at least 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more homology or identity and share a common functional activity are defined herein as sufficiently identical.

In a preferred embodiment, a G2BD protein includes a minimal G2BD, and has an amino acid sequence at least about 50%, 55%, 60%, 65%, 70%, 75%, 80%, 85%, 90%, 91%, 92%, 93%, 94%, 95%, 96%, 97%, 98%, 99%, 99.1% 99.2%, 99.3%, 99.4%, 99.5%, 99.6%, 99.7%, 99.8%, 99.9% or more homologous or identical to the amino acid sequence of SEQ ID NO:10, 12, 14, 16, 18, 20, 22, 24, 26, 28, 30, 32, 34, 36, 38, 40, 42, 44, 46, 48, or 50. In yet another preferred embodiment, a G2BD protein includes a minimal G2BD, and is encoded by a nucleic acid molecule having a nucleotide sequence which hybridizes under stringent hybridization conditions to a complement of a nucleic acid molecule comprising the nucleotide sequence of SEQ ID NO:9, 11, 13, 15, 17, 19, 21, 23, 25, 27, 29, 31, 33, 35, 37, 39, 41, 43, 45, 47, or 49. In another preferred embodiment, a G2BD protein includes a minimal G2BD, and has a G2BD activity.

As used interchangeably herein, a "G2BD activity", "biological activity of G2BD" or "functional activity of G2BD", includes an activity exerted or mediated by a G2BD protein, polypeptide or nucleic acid molecule on a G2BD responsive cell or on a G2BD target molecule, as determined in vivo or in vitro, according to standard techniques. In one embodiment, a G2BD activity is a direct activity, such as an association with a G2BD target molecule (e.g., Ube2G2). As used herein, a "target molecule" or "binding partner" is a molecule with which a G2BD protein binds or interacts in nature, such that G2BD-mediated function is achieved. A G2BD activity can also be an indirect activity, such as a cellular signaling activity mediated by interaction of the G2BD protein with a G2BD target molecule (e.g, Ube2G2) (e.g., regulation of ERAD).

In a preferred embodiment, a G2BD activity is at least one of the following activities: (i) interaction with a target molecule such as Ube2G2; (ii) modulation of Ube2G2 activity, (iii) modulation of ERAD; (iv) modulation of intra- or inter-cellular signaling and/or gene transcription (e.g., either directly or indirectly); (v) modulation of protein stability (e.g., stability of secreted proteins (e.g., antibodies, hormones, growth factors), cell-surface proteins such as receptors (e.g., tyrosine kinase receptors, CFTR, CD3-δ, TCR) or transporters (e.g., neurotransporter reuptake transporters), proteins destined for a subcellular compartment such as lysosomal proteins, and any other proteins that are degraded via ERAD; and/or (vi) modulating of tumor metastasis and/or invasiveness.

Various aspects of the invention are described in further detail in the following subsections:

I. Isolated Nucleic Acid Molecules

One aspect of the invention pertains to isolated nucleic acid molecules that encode G2BD proteins or biologically active portions thereof, as well as nucleic acid fragments sufficient for use as hybridization probes to identify G2BD-encoding nucleic acid molecules and fragments for use as PCR primers for the amplification or mutation of G2BD nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated G2BD nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:9, 11, 13, 15, 17, 19, 21, 23, 25, 27, 29, 31, 33, 35, 37, 39, 41, 43, 45, 47, or 49, or a portion thereof, can be isolated using standard molecular biology techniques and the sequence information provided herein. Using all or a portion of the nucleic acid sequence of SEQ ID NO:9, 11, 13, 15, 17, 19, 21, 23, 25, 27, 29, 31, 33, 35, 37, 39, 41, 43, 45, 47, or 49, as hybridization probes, G2BD nucleic acid molecules can be isolated using standard hybridization and cloning techniques (e.g., as described in Sambrook, J. et al., Molecular Cloning:

A Laboratory Manual. 2.sup. nd ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:9, 11, 13, 15, 17, 19, 21, 23, 25, 27, 29, 31, 33, 35, 37, 39, 41, 43, 45, 47, or 49 can be isolated by the polymerase chain reaction (PCR) using synthetic oligonucleotide primers designed based upon the sequence of SEQ ID NO:9, 11, 13, 15, 17, 19, 21, 23, 25, 27, 29, 31, 33, 35, 37, 39, 41, 43, 45, 47, or 49.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to G2BD nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:9, 11, 13, 15, 17, 19, 21, 23, 25, 27, 29, 31, 33, 35, 37, 39, 41, 43, 45, 47, or 49.

In still another embodiment, an isolated nucleic acid molecule of the invention comprises a nucleic acid molecule which is a complement of the nucleotide sequence shown in SEQ ID NO:9, 11, 13, 15, 17, 19, 21, 23, 25, 27, 29, 31, 33, 35, 37, 39, 41, 43, 45, 47, or 49, or a portion of any of these nucleotide sequences. A nucleic acid molecule which is complementary to the nucleotide sequence shown in SEQ ID NO:9, 11, 13, 15, 17, 19, 21, 23, 25, 27, 29, 31, 33, 35, 37, 39, 41, 43, 45, 47, or 49 is one which is sufficiently complementary to the nucleotide sequence shown in SEQ ID NO:9, 11, 13, 15, 17, 19, 21, 23, 25, 27, 29, 31, 33, 35, 37, 39, 41, 43, 45, 47, or 49, such that it can hybridize to the nucleotide sequence shown in SEQ ID NO:9, 11, 13, 15, 17, 19, 21, 23, 25, 27, 29, 31, 33, 35, 37, 39, 41, 43, 45, 47, or 49, thereby forming a stable duplex.

In still another embodiment, an isolated nucleic acid molecule of the present invention comprises a nucleotide sequence which is at least about 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to the nucleotide sequence shown in SEQ ID NO:9, 11, 13, 15, 17, 19, 21, 23, 25, 27, 29, 31, 33, 35, 37, 39, 41, 43, 45, 47, or 49 (e.g., to the entire length of the nucleotide sequence), or a portion or complement of any of these nucleotide sequences. In one embodiment, a nucleic acid molecule of the present invention comprises a nucleotide sequence which is at least (or no greater than) 10, 15, 18, 20, 25, 30, 33, 35, 40, 45, 50, 75, 80, 90, 99, 100, 105, 114, 150, 195, 200, 210, 250, 261, 300, 333, 342, 350, 400, 438, 450, 500, 550, 600, 645, 650, 700, 750, 800, 850, 900, 950, 1000, 1005 or more nucleotides in length and hybridizes under stringent hybridization conditions to a complement of a nucleic acid molecule of SEQ ID NO:9, 11, 13, 15, 17, 19, 21, 23, 25, 27, 29, 31, 33, 35, 37, 39, 41, 43, 45, 47, or 49.

Moreover, the nucleic acid molecule of the invention can comprise only a portion of the nucleic acid sequence of SEQ ID NO:9, 11, 13, 15, 17, 19, 21, 23, 25, 27, 29, 31, 33, 35, 37, 39, 41, 43, 45, 47, or 49, for example, a fragment which can be used as a probe or primer or a fragment encoding a portion of a G2BD protein, e.g., a biologically active portion of a G2BD protein. The nucleotide sequence determined from the identification of the G2BD of gp78 allows for the generation of probes and primers designed for use in identifying and/or cloning a G2BD in other ubiqutin ligase family members, as well as G2BD homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:9, 11, 13, 15, 17, 19, 21, 23, 25, 27, 29, 31, 33, 35, 37, 39, 41, 43, 45, 47, or 49, of an anti-sense sequence of SEQ ID NO:9, 11, 13, 15, 17, 19, 21, 23, 25, 27, 29, 31, 33, 35, 37, 39, 41, 43, 45, 47, or 49, or of a naturally occurring allelic variant or mutant of SEQ ID NO:9, 11, 13, 15, 17, 19, 21, 23, 25, 27, 29, 31, 33, 35, 37, 39, 41, 43, 45, 47, or 49.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the G2BD nucleotide sequences can be used to detect (e.g., specifically detect) transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of a G2BD sequence, e.g., a domain, region, site or other sequence described herein. The primers should be at least 5, 10, or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress a gp78 protein, such as by measuring a level of a G2BD-encoding nucleic acid in a sample of cells from a subject, e.g., detecting G2BD mRNA levels or determining whether a genomic gp78 gene has been mutated or deleted.

A nucleic acid fragment encoding a "biologically active portion of a G2BD protein" can be prepared by isolating a portion of the nucleotide sequence of SEQ ID NO:9, 11, 13, 15, 17, 19, 21, 23, 25, 27, 29, 31, 33, 35, 37, 39, 41, 43, 45, 47, or 49, which encodes a polypeptide having a G2BD biological activity (the biological activities of the G2BD proteins are described herein), expressing the encoded portion of the G2BD protein (e.g., by recombinant expression in vitro) and assessing the activity of the encoded portion of the G2BD protein. In an exemplary embodiment, the nucleic acid molecule is at least 9, 12, 15, 18, 21, 24, 27, 30, 33, 39, 42, 45, 48, 51, 54, 57, 60, 63, 66, 69, 72, 75, 78, 81, 84, 87, 90, 93, 96, 99, 102, 105, 108, 111, 114, 125, 150, 175, 195, 200, 210, 225, 250, 261, 300, 333, 342, 350, 400, 438, 450, 500, 550, 600, 645, 650, 700, 750, 800, 850, 900, 950, 1000, 1005 or more nucleotides in length and encodes a protein having a G2BD activity (as described herein).

The invention further encompasses nucleic acid molecules that differ from the nucleotide sequence shown in SEQ ID NO:9, 11, 13, 15, 17, 19, 21, 23, 25, 27, 29, 31, 33, 35, 37, 39, 41, 43, 45, 47, or 49, due to degeneracy of the genetic code and thus encode the same G2BD proteins as those encoded by the nucleotide sequence shown in SEQ ID NO:9, 11, 13, 15, 17, 19, 21, 23, 25, 27, 29, 31, 33, 35, 37, 39, 41, 43, 45, 47, or 49. In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO:10, 12, 14, 16, 18, 20, 22, 24, 26, 28, 30, 32, 34, 36, 38, 40, 42, 44, 46, 48, or 50. In yet another embodiment, the nucleic acid molecule encodes the amino acid sequence of human G2BD. If an alignment is needed for this comparison, the sequences should be aligned for maximum identity.

Nucleic acid variants can be naturally occurring, such as allelic variants (same locus), homologues (different locus), and orthologues (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the G2BD proteins. Such genetic polymorphism in the G2BD genes may exist among individuals within a population due to natural allelic variation. As used herein, the terms "gene" and "recombinant gene" refer to nucleic acid molecules which include an open reading frame encoding a G2BD protein, preferably a mammalian G2BD protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:10, 12, 14, 16, 18, 20, 22, 24, 26, 28, 30, 32, 34, 36, 38, 40, 42, 44, 46, 48, or 50, wherein the nucleic acid molecule hybridizes to a complement of a nucleic acid molecule comprising SEQ ID NO:9, 11, 13, 15, 17, 19, 21, 23, 25, 27, 29, 31, 33, 35, 37, 39, 41, 43, 45, 47, or 49, for example, under stringent hybridization conditions.

Allelic variants of G2BD, e.g., human G2BD, include both functional and non-functional G2BD proteins. Functional allelic variants are naturally occurring amino acid sequence variants of the G2BD protein that maintain the ability to, e.g., bind or interact with a G2BD substrate or target molecule (e.g., Ube2G2), modulate Ube2G2 activity, modulate ERAD, modulate protein stability, and/or modulate tumor invasiveness and/or metastasis. Functional allelic variants will typically contain only a conservative substitution of one or more amino acids of SEQ ID NO:10, 12, 14, 16, 18, 20, 22, 24, 26, 28, 30, 32, 34, 36, 38, 40, 42, 44, 46, 48, or 50, or a substitution, deletion or insertion of non-critical residues in non-critical regions of the protein.

Non-functional allelic variants are naturally occurring amino acid sequence variants of the G2BD protein that do not have the ability to, e.g., bind or interact with a G2BD substrate or target molecule (e.g., Ube2G2), modulate Ube2G2 activity, modulate ERAD, modulate protein stability, and/or modulate tumor invasiveness and/or metastasis. Non-functional allelic variants will typically contain a non-conservative substitution, a deletion, or insertion, or premature truncation of the amino acid sequence of SEQ ID NO:10, 12, 14, 16, 18, 20, 22, 24, 26, 28, 30, 32, 34, 36, 38, 40, 42, 44, 46, 48, or 50, or a substitution, insertion, or deletion in critical residues or critical regions of the protein. For example, deletion or mutation of the minimal G2BD from a G2BD protein or from a gp78 protein, renders the G2BD and/or the gp78 protein non-functional.

The present invention further provides non-human orthologues (e.g., non-human orthologues of the human G2BD proteins). Orthologues of the human G2BD proteins are proteins that are isolated from non-human organisms and possess the same G2BD activities as the human G2BD proteins. Orthologues of the human G2BD proteins can readily be identified as comprising an amino acid sequence that is substantially identical to SEQ ID NO:10, 12, 14, 16, 18, 20, 22, 24, 26, 28, 30, 32, 34, 36, 38, 40, 42, 44, 46, 48, or 50.

Moreover, nucleic acid molecules encoding other G2BD family members and, thus, which have a nucleotide sequence which differs from the G2BD sequences of SEQ ID NO:9, 11, 13, 15, 17, 19, 21, 23, 25, 27, 29, 31, 33, 35, 37, 39, 41, 43, 45, 47, or 49 are intended to be within the scope of the invention. For example, another G2BD cDNA can be identified based on the nucleotide sequence of human G2BD. Moreover, nucleic acid molecules encoding G2BD proteins from different species, and which, thus, have a nucleotide sequence which differs from the G2BD sequences of SEQ ID NO:9, 11, 13, 15, 17, 19, 21, 23, 25, 27, 29, 31, 33, 35, 37, 39, 41, 43, 45, 47, or 49 are intended to be within the scope of the invention. For example, a mouse or monkey G2BD cDNA can be identified based on the nucleotide sequence of a human G2BD.

Nucleic acid molecules corresponding to natural allelic variants and homologues of the G2BD cDNAs of the invention can be isolated based on their homology to the G2BD nucleic acids disclosed herein using the cDNAs disclosed herein, or a portion thereof, as a hybridization probe according to standard hybridization techniques under stringent hybridization conditions.

Orthologues, homologues, and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:9, 11, 13, 15, 17, 19, 21, 23, 25, 27, 29, 31, 33, 35, 37, 39, 41, 43, 45, 47, or 49. In other embodiment, the nucleic acid is at least 9, 12, 15, 18, 21, 24, 27, 30, 33, 39, 42, 45, 48, 51, 54, 57, 60, 63, 66, 69, 72, 75, 78, 81, 84, 87, 90, 93, 96, 99, 102, 105, 108, 111, 114, 125, 150, 175, 195, 200, 210, 225, 250, 261, 300, 333, 342, 350, 400, 438, 450, 500, 550, 600, 645, 650, 700, 750, 800, 850, 900, 950, 1000, 1005 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4, and 6. Additional stringent conditions can be found in Molecular Cloning: A Laboratory Manual, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4× SSC plus 50% formamide at about 42-50° C.) followed by one or more washes in 1× SSC, at about 65-70° C. A preferred, non-limiting example of highly stringent hybridization conditions includes hybridization in 1× SSC, at about 65-70° C. (or alternatively hybridization in 1× SSC plus 50% formamide at about 42-50° C.) followed by one or more washes in 0.3× SSC, at about 65-70° C. A preferred, non-limiting example of reduced stringency hybridization conditions includes hybridization in 4× SSC, at about 50-60° C. (or alternatively hybridization in 6× SSC plus 50% formamide at about 40-45° C.) followed by one or more washes in 2× SSC, at about 50-60° C. Ranges intermediate to the above-recited values, e.g., at 65-70° C. or at 42-50° C. are also intended to be encompassed by the present invention. SSPE (1× SSPE is 0.15M NaCl, 10 mM $NaH_2PO_4$, and 1.25 mM EDTA, pH 7.4) can be substituted for SSC (1× SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$[$Na^+$])+0.41(% G+C)−(600/N), where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) Proc. Natl. Acad. Sci. USA 81:1991-1995), or alternatively 0.2× SSC, 1% SDS.

Preferably, an isolated nucleic acid molecule of the invention that hybridizes under stringent conditions to the sequence of SEQ ID NO:9, 11, 13, 15, 17, 19, 21, 23, 25, 27, 29, 31, 33, 35, 37, 39, 41, 43, 45, 47, or 49 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the G2BD sequences that may exist in the population, the skilled artisan will further appreciate that changes can be introduced by mutation into the nucleotide sequences of SEQ ID NO:9, 11, 13, 15, 17, 19, 21, 23, 25, 27, 29, 31, 33, 35, 37, 39, 41, 43, 45, 47, or 49, thereby leading to changes in the amino acid sequence of the encoded G2BD proteins, without altering the functional ability of the G2BD proteins. For example, nucleotide substitutions leading to amino acid substitutions at "non-essential" amino acid residues can be made in the sequence of SEQ ID NO:9, 11, 13, 15, 17, 19, 21, 23, 25, 27, 29, 31, 33, 35, 37, 39, 41, 43, 45, 47, or 49. A "non-essential" amino acid residue is a residue that can be altered from the wild-type sequence of G2BD or G2BD (e.g., the sequence of SEQ ID NO: 10, 12, 14, 16, 18, 20, 22, 24, 26, 28, 30, 32, 34, 36, 38, 40, 42, 44, 46, 48, or 50) without altering the biological activity, whereas an "essential" amino acid residue is required for biological activity. For example, amino acid residues that are in the minimal G2BD are not likely to be amenable to alteration.

Accordingly, another aspect of the invention pertains to nucleic acid molecules encoding G2BD proteins that contain changes in amino acid residues that are not essential for activity. Such G2BD proteins differ in amino acid sequence from SEQ ID NO:10, 12, 14, 16, 18, 20, 22, 24, 26, 28, 30, 32, 34, 36, 38, 40, 42, 44, 46, 48, or 50, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO:10, 12, 14, 16, 18, 20, 22, 24, 26, 28, 30, 32, 34, 36, 38, 40, 42, 44, 46, 48, or 50, e.g., to the entire length of SEQ ID NO:10, 12, 14, 16, 18, 20, 22, 24, 26, 28, 30, 32, 34, 36, 38, 40, 42, 44, 46, 48, or 50.

An isolated nucleic acid molecule encoding a G2BD protein identical to the protein of SEQ ID NO:10, 12, 14, 16, 18, 20, 22, 24, 26, 28, 30, 32, 34, 36, 38, 40, 42, 44, 46, 48, or 50 can be created by introducing one or more nucleotide substitutions, additions or deletions into the nucleotide sequence of SEQ ID NO:9, 11, 13, 15, 17, 19, 21, 23, 25, 27, 29, 31, 33, 35, 37, 39, 41, 43, 45, 47, or 49, such that one or more amino acid substitutions, additions or deletions are introduced into the encoded protein. Mutations can be introduced into SEQ ID NO:9, 11, 13, 15, 17, 19, 21, 23, 25, 27, 29, 31, 33, 35, 37, 39, 41, 43, 45, 47, or 49 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a G2BD protein is preferably replaced with another amino acid residue from the same side chain family. Alternatively, in another embodiment, mutations can be introduced randomly along all or part of a G2BD coding sequence, such as by saturation mutagenesis, and the resultant mutants can be screened for G2BD biological activity to identify mutants that retain activity. Following mutagenesis of SEQ ID NO:9, 11, 13, 15, 17, 19, 21, 23, 25, 27, 29, 31, 33, 35, 37, 39, 41, 43, 45, 47, or 49, the encoded protein can be expressed recombinantly and the activity of the protein can be determined.

In a preferred embodiment, a mutant G2BD protein can be assayed for the ability to (i) interact with a target molecule such as Ube2G2; (ii) modulate Ube2G2 activity; (iii) modulate ERAD; (iv) modulate intra- or inter-cellular signaling and/or gene transcription (e.g., either directly or indirectly); (v) modulate protein stability (e.g., CD3-δ and/or TCR stability); and/or (vi) modulate tumor metastasis and/or invasiveness.

In addition to the nucleic acid molecules encoding G2BD proteins described above, another aspect of the invention pertains to isolated nucleic acid molecules which are antisense thereto. In an exemplary embodiment, the invention provides an isolated nucleic acid molecule which is antisense to a G2BD nucleic acid molecule (e.g., is antisense to the coding strand of a G2BD nucleic acid molecule). An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire G2BD coding strand, or to only a portion thereof In one embodiment, an antisense nucleic acid molecule is antisense to "coding region sequences" of the coding strand of a nucleotide sequence encoding G2BD. The term "coding region sequences" refers to the region of the nucleotide sequence comprising codons which are translated into amino acid residues (e.g., SEQ ID NO:9, 11, 13, 15, 17, 19, 21, 23, 25, 27, 29, 31, 33, 35, 37, 39, 41, 43, 45, 47, or 49). In another embodiment, the antisense nucleic acid molecule is antisense to a "noncoding region" of the coding strand of a nucleotide sequence encoding G2BD. The term "noncoding region" refers to 5' and/or 3' sequences which flank the coding region sequences that are not translated into amino acids (also referred to as 5' and 3' untranslated regions).

Given the coding strand sequences encoding G2BD disclosed herein (e.g., SEQ ID NO:9, 11, 13, 15, 17, 19, 21, 23, 25, 27, 29, 31, 33, 35, 37, 39, 41, 43, 45, 47, or 49), antisense nucleic acids of the invention can be designed according to the rules of Watson and Crick base pairing. The antisense nucleic acid molecule can be complementary to coding region sequences of G2BD mRNA, but more preferably is an oligonucleotide which is antisense to only a portion of the G2BD mRNA. An antisense oligonucleotide can be, for example, about 5, 10, 15, 20, 25, 30, 35, 40, 45, 50, 55, 60, 65, 70, 75, 80, or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a G2BD protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an MRNA, to which they have a complementary region. Thus, ribozymes (e.g., hammerhead ribozymes (described in Haseloff and Gerlach (1988) Nature 334:585-591)) can be used to catalytically cleave G2BD MRNA transcripts to thereby inhibit translation of G2BD mRNA. A ribozyme having specificity for a G2BD-encoding nucleic acid can be designed based upon the nucleotide sequence of a G2BD cDNA disclosed herein (i.e., SEQ ID NO:9, 11, 13, 15, 17, 19, 21, 23, 25, 27, 29, 31, 33, 35, 37, 39, 41, 43, 45, 47, or 49). For example, a derivative of a Tetrahymena L-19 IVS RNA can be constructed in which the nucleotide sequence of the active site is complementary to the nucleotide sequence to be cleaved in a G2BD-encoding MRNA. See, e.g., Cech et al., U.S. Pat. No. 4,987,071; and Cech et al., U.S. Pat. No. 5,116,742. Alternatively, G2BD MRNA can be used to select a catalytic RNA having a specific ribonuclease activity from a pool of RNA molecules. See, e.g., Bartel, D. and Szostak, J. W. (1993) Science 261:1411-1418.

Alternatively, G2BD gene expression can be inhibited by targeting nucleotide sequences complementary to the regulatory region of the gp78 gene (e.g., the gp78 promoter and/or enhancers) to form triple helical structures that prevent transcription of the G2BD gene in target cells. See generally, Helene, C. (1991) Anticancer Drug Des. 6(6

Helene, C. et al. (1992) Ann. N.Y. Acad. Sci. 660:27-36; and Maher, L. J. (1992) Bioessays 14(12):807-15.

In yet another embodiment, the G2BD nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) Bioorg. Med. Chem. 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) Proc. Natl. Acad. Sci. USA 93:14670-675.

PNAs of G2BD nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of G2BD nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup and Nielsein (1996) supra)); or as probes or primers for DNA sequencing or hybridization (Hyrup and Nielsen (1996) supra; Perry-O'Keefe et al. (1996) supra).

In another embodiment, PNAs of G2BD can be modified (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of G2BD nucleic acid molecules can be generated which may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn, P. J. et al. (1996) Nucleic Acids Res. 24(17):3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) Nucleic Acids Res. 17:5973-88). PNA monomers are then coupled in a stepwise manner to produce a chimeric molecule with a 5' PNA segment and a 3' DNA segment (Finn, P. J. et al. (1996) supra). Alternatively, chimeric molecules can be synthesized with a 5' DNA segment and a 3' PNA segment (Peterser, K. H. et al. (1975) Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) Biotechniques 6:958-976) or intercalating agents (See, e.g., Zon (1988) Pharm. Res. 5:539-549). To this end, the oligonucleotide may be conjugated to another molecule (e.g., a peptide, hybridization triggered cross-linking agent, transport agent, or hybridization-triggered cleavage agent).

II. Isolated G2BD Proteins and Anti-G2BD Antibodies

One aspect of the invention pertains to isolated or recombinant G2BD proteins and polypeptides, and biologically active portions thereof. In one embodiment, G2BD proteins can be isolated from cells or tissue sources by an appropriate purification scheme using standard protein purification techniques. In another embodiment, G2BD proteins are produced by recombinant DNA techniques. Alternative to recombinant expression, a G2BD protein or polypeptide can be synthesized chemically using standard peptide synthesis techniques.

An "isolated" or "purified" protein or biologically active portion thereof is substantially free of cellular material or other contaminating proteins from the cell or tissue source from which the G2BD protein is derived, or substantially free from chemical precursors or other chemicals when chemically synthesized. The language "substantially free of cellular material" includes preparations of G2BD protein in which the protein is separated from cellular components of the cells from which it is isolated or recombinantly produced. In one embodiment, the language "substantially free of cellular material" includes preparations of G2BD protein having less than about 30% (by dry weight) of non-G2BD protein (also referred to herein as a "contaminating protein"), more preferably less than about 20% of non-G2BD protein, still more preferably less than about 10% of non-G2BD protein, and most preferably less than about 5% non-G2BD protein. When the G2BD protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of G2BD protein in which the protein is separated from chemical precursors or other chemicals which are involved in the synthesis of the protein. In one embodiment, the language "substantially free of chemical precursors or other chemicals" includes preparations of G2BD protein having less than about 30% (by dry weight) of chemical precursors or non-G2BD chemicals, more preferably less than about 20% chemical precursors or non-G2BD chemicals, still more preferably less than about 10% chemical precursors or non-G2BD chemicals, and most preferably less than about 5% chemical precursors or non-G2BD chemicals.

As used herein, a "biologically active portion" of a G2BD protein includes a fragment of a G2BD protein which participates in an interaction between a G2BD molecule and a non-G2BD molecule (e.g., Ube2G2). In a preferred embodiment, a biologically active portion of a G2BD includes a minimal G2BD (SEQ ID NO:10 or SEQ ID NO:34). Biologically active portions of a G2BD protein include peptides comprising amino acid sequences sufficiently identical to or derived from the G2BD amino acid sequences, e.g., the amino acid sequences shown in SEQ ID NO:10, 12, 14, 16, 18, 20, 22, 24, 26, 28, 30, 32, 34, 36, 38, 40, 42, 44, 46, 48, or 50, which include sufficient amino acid residues to exhibit at least one activity of a G2BD protein. Typically, biologically active portions comprise a domain or motif with at least one activity of the G2BD protein, e.g., the ability to interact with and/or bind to a G2BD target molecule (e.g., Ube2G2); the ability to modulate the activity of a G2BD target molecule (e.g., Ube2G2); the ability to modulate ERAD in a cell; the ability to modulate protein stability in a cell; the ability to modulate inter- or intracellular signaling; and/or the ability to modulate tumor invasiveness and/or metastasis. A biologically active portion of a G2BD protein can be a polypeptide which is, for example, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 73, 75, 80, 85, 87, 90, 95, 100, 105, 110, 111, 114, 115, 120, 125, 130, 135, 140, 145, 146, 150, 175, 200, 215, 250, 300, 330, 335 or more amino acids in length. Biologically active portions of a G2BD protein can be used as targets for developing agents which modulate a G2BD mediated activity, e.g., any of the aforementioned G2BD activities.

Another aspect of the invention features fragments of the protein having the amino acid sequence of SEQ ID NO:10, 12, 14, 16, 18, 20, 22, 24, 26, 28, 30, 32, 34, 36, 38, 40, 42, 44, 46, 48, or 50, for example, for use in the methods described herein. In one embodiment, a fragment comprises at least 6 amino acids (e.g., contiguous or consecutive amino acids) of the amino acid sequence of SEQ ID NO:10, 12, 14, 16, 18, 20, 22, 24, 26, 28, 30, 32, 34, 36, 38, 40, 42, 44, 46, 48, or 50. In another embodiment, a fragment comprises at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 73, 75, 80, 85, 87, 90, 95, 100, 105, 110, 111, 114, 115, 120, 125, 130, 135, 140, 145, 146, 150, 175, 200, 215, 250, 300, 330, 33 or more amino acids (e.g., contiguous or consecutive amino acids) of the amino acid sequence of SEQ ID NO: 10, 12, 14, 16, 18, 20, 22, 24, 26, 28, 30, 32, 34, 36, 38, 40, 42, 44, 46, 48, or 50.

In a preferred embodiment, a G2BD protein has an amino acid sequence shown in SEQ ID NO:10, 12, 14, 16, 18, 20, 22, 24, 26, 28, 30, 32, 34, 36, 38, 40, 42, 44, 46, 48, or 50. In other embodiments, the G2BD protein is substantially identical to SEQ ID NO: 10, 12, 14, 16, 18, 20, 22, 24, 26, 28, 30, 32, 34, 36, 38, 40, 42, 44, 46, 48, or 50, and retains the functional activity of the protein of SEQ ID NO:10, 12, 14, 16, 18, 20, 22, 24, 26, 28, 30, 32, 34, 36, 38, 40, 42, 44, 46, 48, or 50, yet differs in amino acid sequence due to natural allelic variation or mutagenesis, as described in detail in subsection I above. In another embodiment, the G2BD protein is a protein which comprises an amino acid sequence at least about 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO:10, 12, 14, 16, 18, 20, 22, 24, 26, 28, 30, 32, 34, 36, 38, 40, 42, 44, 46, 48, or 50.

In another embodiment, the invention features a G2BD protein which is encoded by a nucleic acid molecule consisting of a nucleotide sequence at least about 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to a nucleotide sequence of SEQ ID NO:9, 11, 13, 15, 17, 19, 21, 23, 25, 27, 29, 31, 33, 35, 37, 39, 41, 43, 45, 47, or 49, or a complement thereof. This invention further features a G2BD protein which is encoded by a nucleic acid molecule consisting of a nucleotide sequence which hybridizes under stringent hybridization conditions to a complement of a nucleic acid molecule comprising the nucleotide sequence of SEQ ID NO:9, 11, 13, 15, 17, 19, 21, 23, 25, 27, 29, 31, 33, 35, 37, 39, 41, 43, 45, 47, or 49.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to an amino acid sequence having 100 amino acid residues, at least 30, preferably at least 40, more preferably at least 50, even more preferably at least 60, and even more preferably at least 70, 80, or 90 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at online through the Genetics Computer Group), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at online through the Genetics Computer Group), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (Comput. Appl. Biosci. 4:11-17 (1988)) which has been incorporated into the ALIGN program (version 2.0 or version 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to G2BD nucleic acid molecules of the invention. BLAST protein searches can be performed with the XBLAST program, score=50, wordlength=3 to obtain amino acid sequences homologous to G2BD protein molecules of the invention. To obtain gapped alignments for comparison purposes, Gapped BLAST can be utilized as described in Altschul et al. (1997) Nucleic Acids Res. 25(17):3389-3402. When utilizing BLAST and Gapped BLAST programs, the default parameters of the respective programs (e.g., XBLAST and NBLAST) can be used. See the website for the National Center for Biotechnology Information.

The invention also provides G2BD chimeric or fusion proteins. As used herein, a G2BD "chimeric protein" or "fusion protein" comprises a G2BD polypeptide operatively linked to a non-G2BD polypeptide (e.g., a non-gp78 polypeptide). A "G2BD polypeptide" refers to a polypeptide having an amino acid sequence corresponding to G2BD, for example, whereas a "non-G2BD polypeptide" refers to a polypeptide having an amino acid sequence corresponding to a protein which is not substantially identical to the G2BD protein, e.g., a protein which is different from the G2BD protein and which is derived from the same or a different organism. Within a G2BD fusion protein the G2BD polypeptide can correspond to all or a portion of a G2BD protein. In a preferred embodiment, a G2BD fusion protein comprises at least one biologically active portion of a G2BD protein (e.g., a minimal G2BD). Within the fusion protein, the term "operatively linked" is intended to indicate that the G2BD polypeptide and the non-G2BD polypeptide are fused in-frame to each other. The non-G2BD polypeptide can be fused to the N-terminus or C-terminus of the G2BD polypeptide.

For example, in one embodiment, the fusion protein is a GST-G2BD fusion protein in which the G2BD sequences are fused to the C-terminus of the GST sequences. Such fusion proteins can facilitate the purification of recombinant G2BD. In another embodiment, the fusion protein is a G2BD protein containing a heterologous signal sequence at its N-terminus. In certain host cells (e.g., mammalian host cells), expression and/or secretion of G2BD can be increased through use of a heterologous signal sequence.

In another embodiment, the fusion protein is a G2BD protein fused to a fluorescent protein (e.g., GFP). In a further embodiment, G2BD proteins can be fused to a peptide tag which can facilitate purification of the fusion protein, as well as detection and/or immunoprecipitation using antibodies directed to the peptide tag. Preferred peptide tags include, but are not limited to, myc tags and poly-histidine (e.g., 6 His residues) tags.

The G2BD fusion proteins of the invention can be incorporated into pharmaceutical compositions and administered to a subject in vivo. The G2BD fusion proteins can be used to affect the bioavailability of a G2BD target molecule (e.g., Ube2G2). Use of G2BD fusion proteins may be useful therapeutically for the treatment of disorders caused by or associated with, for example, aberrant ERAD and/or aberrant protein stability (e.g., ERAD associated disorders).

Moreover, the G2BD-fusion proteins of the invention can be used as immunogens to produce anti-G2BD antibodies in a subject, to detect G2BD target molecules (e.g., Ube2G2), and in screening assays to identify molecules which inhibit or enhance the interaction of G2BD with a G2BD target molecule (e.g., Ube2G2).

Preferably, a G2BD chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons:1992). Moreover, many expression vectors are commercially available that already encode a fusion moiety (e.g., a GST polypeptide). A G2BD-encoding nucleic acid can be cloned into such an expression vector such that the fusion moiety is linked in-frame to the G2BD protein.

The present invention also pertains to variants of the G2BD proteins which function as either G2BD agonists (mimetics) or as G2BD antagonists. Variants of the G2BD proteins can be generated by mutagenesis, e.g., discrete point mutation or truncation of a G2BD protein. An agonist of the G2BD proteins can retain substantially the same, or a subset, of the biological activities of the naturally occurring form of a G2BD protein. An antagonist of a G2BD protein can inhibit one or more of the activities of the naturally occurring form of the G2BD protein by, for example, competitively modulating a G2BD-mediated activity of a G2BD protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the G2BD protein.

In one embodiment, variants of a G2BD protein which function as either G2BD agonists (mimetics) or as G2BD antagonists can be identified by screening combinatorial libraries of mutants, e.g., truncation mutants, of a G2BD protein for G2BD protein agonist or antagonist activity. In one embodiment, a variegated library of G2BD variants is generated by combinatorial mutagenesis at the nucleic acid level and is encoded by a variegated gene library. A variegated library of G2BD variants can be produced by, for example, enzymatically ligating a mixture of synthetic oligonucleotides into gene sequences such that a degenerate set of potential G2BD sequences is expressible as individual polypeptides, or alternatively, as a set of larger fusion proteins (e.g., for phage display) containing the set of G2BD sequences therein. There are a variety of methods which can be used to produce libraries of potential G2BD variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential G2BD sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acids Res. 11:477.

In addition, libraries of fragments of a G2BD protein coding sequence can be used to generate a variegated population of G2BD fragments for screening and subsequent selection of variants of a G2BD protein. In one embodiment, a library of coding sequence fragments can be generated by treating a double stranded PCR fragment of a G2BD coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the G2BD protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of G2BD proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify G2BD variants (Arkin and Youvan (1992) Proc. Natl. Acad. Sci. USA 89:7811-7815; Delagrave et al. (1993) Protein Eng. 6(3):327-331).

In one embodiment, cell based assays can be exploited to analyze a variegated G2BD library. For example, a library of expression vectors can be transfected into a cell line which ordinarily responds to G2BD in a particular G2BD target (Ube2G2)-dependent manner. The transfected cells are then contacted with G2BD and the effect of the expression of the mutant on activity of the G2BD target can be detected by measuring e.g., binding of the target (e.g., Ube2G2) to G2BD, and/or the level of expression (i.e., stability) of a particular protein (e.g., CD3-δ, the TCR-α subunit of the T cell receptor, and/or any other protein known to be modulated by ERAD), and the individual clones further characterized.

An isolated G2BD protein, or a portion or fragment thereof, can be used as an immunogen to generate antibodies that bind G2BD using standard techniques for polyclonal and monoclonal antibody preparation. A full-length G2BD protein can be used or, alternatively, the invention provides antigenic peptide fragments of G2BD for use as immunogens. The antigenic peptide of G2BD comprises at least 8 amino acid residues of the amino acid sequence shown in SEQ ID NO:10, 12, 14, 16, 18, 20, 22, 24, 26, 28, 30, 32, 34, 36, 38, 40, 42, 44, 46, 48, or 50 and encompasses an epitope of G2BD such that an antibody raised against the peptide forms a specific immune complex with G2BD. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of G2BD that are located on the surface of the protein, e.g. hydrophilic regions, as well as regions with high antigenicity. More preferably, an antigenic peptide includes a minimal G2BD.

A G2BD immunogen typically is used to prepare antibodies by immunizing a suitable subject (e.g., rabbit, goat, mouse, or other mammal) with the immunogen. An appropriate immunogenic preparation can contain, for example, recombinantly expressed G2BD protein or a chemically-synthesized G2BD polypeptide. The preparation can further include an adjuvant, such as Freund's complete or incomplete adjuvant, or similar immunostimulatory agent. Immunization of a suitable subject with an immunogenic G2BD preparation induces a polyclonal anti-G2BD antibody response.

Accordingly, another aspect of the invention pertains to anti-G2BD antibodies. The term "antibody" as used herein refers to immunoglobulin molecules and immunologically active portions of immunoglobulin molecules, i.e., molecules that contain an antigen binding site which specifically binds (immunoreacts with) an antigen, such as G2BD. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind G2BD. The term "monoclonal antibody" or "monoclonal antibody composition", as used herein, refers to a population of antibody molecules that contain only one species of an antigen binding site capable of immunoreacting with a particular epitope of G2BD. A monoclonal antibody composition thus typically displays a single binding affinity for a particular G2BD protein with which it immunoreacts.

Polyclonal anti-G2BD antibodies can be prepared as described above by immunizing a suitable subject with a G2BD immunogen. The anti-G2BD antibody titer in the immunized subject can be monitored over time by standard techniques, such as with an enzyme linked immunosorbent assay (ELISA) using immobilized G2BD. If desired, the antibody molecules directed against G2BD can be isolated from the mammal (e.g., from the blood) and further purified by well known techniques, such as protein A chromatography to obtain the IgG fraction. At an appropriate time after immunization, e.g., when the anti-G2BD antibody titers are highest, antibody-producing cells can be obtained from the subject and used to prepare monoclonal antibodies by standard techniques, such as the hybridoma technique originally described by Kohler and Milstein (1975) Nature 256:495-497 (see also Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985), Monoclonal Antibodies and Cancer Therapy, Alan R Liss, Inc., pp. 77-96) or trioma techniques. The technology for producing monoclonal antibody hybridomas is well known (see generally Kenneth, R. H., in Monoclonal Antibodies: A New Dimension In Biological Analyses, Plenum Publishing Corp., New York, N.Y. (1980); Lerner, E. A. (1981) Yale J. Biol. Med, 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with a G2BD immunogen as described above, and the culture supernatants of the resulting hybridoma cells are screened to identify a hybridoma producing a monoclonal antibody that binds G2BD.

Any of the many well known protocols used for fusing lymphocytes and immortalized cell lines can be applied for the purpose of generating an anti-G2BD monoclonal antibody (see, e.g., Galfre, G. et al. (1977) Nature 266:55052; Gefter et al. (1977) supra; Lerner (1981) supra; Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind G2BD, e.g., using a standard ELISA assay.

Alternative to preparing monoclonal antibody-secreting hybridomas, a monoclonal anti-G2BD antibody can be identified and isolated by screening a recombinant combinatorial immunoglobulin library (e.g., an antibody phage display library) with G2BD to thereby isolate immunoglobulin library members that bind G2BD. Kits for generating and screening phage display libraries are commercially available (e.g., the Pharmacia Recombinant Phage Antibody System, Catalog No. 27-9400-01; and the Stratagene SurfAP™ Phage Display Kit, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication No. WO 92/20791; Markland et al. PCT International Publication No. WO 92/15679; Breitling et al., PCT International Publication No. WO 93/01288; McCafferty et al., PCT International Publication No. WO 92/01047; Garrard et al., PCT International Publication No. WO 92/09690; Ladner et al., PCT International Publication No. WO 90/02809; Fuchs et al. (1991) Biotechnology (NY) 9:1369-1372; Hay et al. (1992) Hum. Antibodies Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrard et al. (1991) Biotechnology (N.Y.) 9:1373-1377; Hogenboom et al. (1991) Nucleic Acids Res. 19:4133-4137; Barbas et al. (1991) Proc. Natl. Acad. Sci. USA 88:7978-7982; and McCafferty et al. (1990) Nature 348:552-554.

Additionally, recombinant anti-G2BD antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al., International Application No. PCT/US86/02269; Alira et al., European Patent Application No. 184, 187; Taniguchi, M., European Patent Application No. 171, 496; Morrison et al., European Patent Application 173, 494; Neuberger et al., PCT International Publication No. WO 86/01533; Cabilly et al., U.S. Pat. No. 4,816,567; Cabilly et al., European Patent Application 125,023; Better et al. (1988) Science 240:1041-1043; Liu et al. (1987) Proc. Natl. Acad. Sci. USA 84:3439-3443; Liu et al. (1987) J. Immunol. 139: 3521-3526; Sun et al. (1987) Proc. Natl. Acad. Sci. USA 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) Biotechniques 4:214; Winter, U.S. Pat. No. 5,225,539; Jones et al. (1986) Nature 321:552-525; Verhoeyen et al. (1988) Science 239:1534; and Beidler et al. (1988) J. Immunol. 141:4053-4060.

An anti-G2BD antibody (e.g., monoclonal antibody) can be used to isolate G2BD by standard techniques, such as affinity chromatography or immunoprecipitation. An anti-G2BD antibody can facilitate the purification of G2BD from cells and of recombinantly produced G2BD expressed in host cells. Moreover, an anti-G2BD antibody can be used to detect G2BD protein (e.g., in a cellular lysate or cell supernatant) in order to evaluate the abundance and pattern of expression of the G2BD protein. Anti-G2BD antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance or label. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, $^{32}P$, $^{33}P$, and/or $^{3}H$.

In another embodiment, because they bind to the G2BD target molecule Ube2G2 with high affinity, the G2BD proteins of the present invention (e.g., SEQ ID NO:10, 12, 14, 16, 18, 20, 22, 24, 26, 28, 30, 32, 34, 36, 38, 40, 42, 44, 46, 48, or 50) can be coupled to a detectable substance or label, as described above for anti-G2BD antibodies, and can be used to purify and/or detect Ube2G2.

III. Recombinant Expression Vectors and Host Cells

Another aspect of the invention pertains to vectors, for example recombinant expression vectors, containing a G2BD nucleic acid molecule or vectors containing a nucleic acid molecule which encodes a G2BD protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g. polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., G2BD proteins, mutant forms of G2BD proteins, fusion proteins, and the like).

Accordingly, an exemplary embodiment provides a method for producing a protein, preferably a G2BD protein, by culturing in a suitable medium a host cell of the invention (e.g., a mammalian host cell such as a non-human mammalian cell) containing a recombinant expression vector, such that the protein is produced.

The recombinant expression vectors of the invention can be designed for expression of G2BD proteins in prokaryotic or eukaryotic cells. For example, G2BD proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in G2BD activity assays (e.g., direct assays or competitive assays described in detail below), or to generate antibodies specific for G2BD proteins, for example. In a preferred embodiment, a G2BD fusion protein expressed in a viral (e.g., retroviral) retroviral expression vector of the present invention can be utilized to infect cells in vivo or in vitro.

Examples of suitable inducible non-fusion *E. coli* expression vectors include pTrc (Amann et al. (1988) Gene 69:301-315) and pET 11d (Studier et al. (1990) Methods Enzymol. 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS 174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20:2111-2118). Such alteration of nucleic acid sequences of the invention can be carried out by standard DNA synthesis techniques.

In another embodiment, the G2BD expression vector is a yeast expression vector. Examples of vectors for expression in yeast S. cerevisiae include pYepSec1 (Baldari et al. (1987) EMBO J. 6:229-234), pMFa (Kuijan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp., San Diego, Calif.).

Alternatively, G2BD proteins can be expressed in insect cells using baculovirus expression vectors. Baculovirus vectors available for expression of proteins in cultured insect cells (e.g., Sf9 cells) include the pAc series (Smith et al. (1983) Mol. Cell Biol. 3:2156-2165) and the pVL series (Lucklow and Surnmers (1989) Virology 170:31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirns and Simian Virus 40. For other suitable expression systems for both prokaryotic and eukaryotic cells see chapters 16 and 17 of Sambrook, J. et al., Molecular Cloning: A Laboratory Manual. 2.sup.nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Baneiji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the .alpha.-fetoprotein promoter (Campes and Tilghman (1989) Genes Dev. 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to G2BD MRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al. "Antisense RNA as a molecular tool for genetic analysis", Reviews—Trends in Genetics, Vol. 1(1) 1986.

Another aspect of the invention pertains to host cells into which a G2BD nucleic acid molecule of the invention is introduced, e.g., a G2BD nucleic acid molecule within a vector (e.g., a recombinant expression vector) or a G2BD nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a G2BD protein can be expressed in bacterial cells such as E. coli, insect cells, yeast or mammalian cells (such as Chinese hamster ovary cells (CHO), HEK293T, or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2.sup.nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify an d select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a G2BD protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a G2BD protein. Accordingly, the invention further provides methods for producing a G2BD protein using the host cells of the invention. In one embodiment, the method comprises culturing the host cell of the invention (into which a recombinant expression vector encoding a G2BD protein has been introduced) in a suitable medium such that a G2BD protein is produced. In another embodiment, the method further comprises isolating a G2BD protein from the medium or the host cell.

The host cells of the invention can also be used to produce non-human transgenic animals. For example, in one embodiment, a host cell of the invention is a fertilized oocyte or an embryonic stem cell into which G2BD coding sequences have been introduced. Such host cells can then be used to create non-human transgenic animals in which exogenous G2BD sequences have been introduced into their genome or homologous recombinant animals in which endogenous G2BD sequences have been altered. Such animals are useful for studying the function and/or activity of a G2BD protein and for identifying and/or evaluating modulators of G2BD activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, rabbits, fish, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous G2BD gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a G2BD-encoding nucleic acid into the male pronuclei of a fertilized oocyte, e.g., by microinjection or retroviral infection, and allowing the oocyte to develop in a pseudopregnant female foster animal. The G2BD DNA sequence of SEQ ID NO:9, 11, 13, 15, 17, 19, 21, 23, 25, 27, 29, 31, 33, 35, 37, 39, 41, 43, 45, 47, or 49 can be introduced as a transgene into the genome of a non-human animal. Alternatively, a non-human homologue of a human G2BD gene, such as a rat or mouse G2BD gene, can be used as a transgene. Alternatively, a G2BD gene homologue, such as another G2BD family member, can be isolated based on hybridization to the G2BD cDNA sequences of SEQ ID NO:9, 11, 13, 15, 17, 19, 21, 23, 25, 27, 29, 31, 33, 35, 37, 39, 41, 43, 45, 47, or 49 (described further in subsection I above) and used as a transgene. Intronic sequences and polyadenylation signals can also be included in the transgene to increase the efficiency of expression of the transgene. A tissue-specific regulatory sequence(s) can be operably linked to a G2BD transgene to direct expression of a G2BD protein to particular cells. Methods for generating transgenic animals via embryo manipulation and microinjection, particularly animals such as mice, have become conventional in the art and are described, for example, in U.S. Pat. Nos. 4,736,866 and 4,870, 009,both by Leder et al., U.S. Pat. No. 4,873,191 by Wagner et al. and in Hogan, B., Manipulating the Mouse Embryo (Cold Spring Harbor Laboratory Press, Cold Spring Harbor, N.Y., 1986). Similar methods are used for production of other transgenic animals. A transgenic founder animal can be identified based upon the presence of a G2BD transgene in its genome and/or expression of G2BD mRNA in tissues or cells of the animals. A transgenic founder animal can then be used to breed additional animals carrying the transgene. Moreover, transgenic animals carrying a transgene encoding a G2BD protein can further be bred to other transgenic animals carrying other transgenes.

To create a homologous recombinant animal, a vector is prepared which contains at least a portion of a G2BD gene into which a deletion, addition or substitution has been introduced to thereby alter, e.g., functionally disrupt, the G2BD gene. The G2BD gene can be a human gene (e.g., the DNA of SEQ iD NO:9, 11, 13, 15, 17, 19, 21, 23, 25, 27, 29, 31, 33, 35, 37, 39, 41, 43, 45, 47, or 49), but more preferably, is a non-human homologue of a human G2BD gene (e.g., a cDNA isolated by stringent hybridization with the nucleotide sequence of SEQ ID NO:9, 11, 13, 15, 17, 19, 21, 23, 25, 27, 29, 31, 33, 35, 37, 39, 41, 43, 45, 47, or 49), For example, a mouse G2BD gene can be used to construct a homologous recombination nucleic acid molecule, e.g., a vector, suitable for altering an endogenous G2BD gene in the mouse genome. In a preferred embodiment, the homologous recombination nucleic acid molecule is designed such that, upon homologous recombination, the endogenous G2BD gene is functionally disrupted (i.e., no longer encodes a functional protein; also referred to as a "knock out" vector). Alternatively, the homologous recombination nucleic acid molecule can be designed such that, upon homologous recombination, the endogenous G2BD gene is mutated or otherwise altered but still encodes functional protein (e.g., the upstream regulatory region can be altered to thereby alter the expression of the endogenous G2BD protein). In the homologous recombination nucleic acid molecule, the altered portion of the G2BD gene is flanked at its 5' and 3' ends by additional nucleic acid sequence of the G2BD gene to allow for homologous recombination to occur between the exogenous G2BD gene carried by the homologous recombination nucleic acid molecule and an endogenous G2BD gene in a cell, e.g., an embryonic stem cell. The additional flanking G2BD nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) Cell 51:503 for a description of homologous recombination vectors). The homologous recombination nucleic acid molecule is introduced into a cell, e.g., an embryonic stem cell line (e.g., by electroporation) and cells in which the introduced G2BD gene has homologously recombined with the endogenous G2BD gene are selected (see e.g., Li, E. et al. (1992) Cell 69:915). The selected cells can then be injected into a blastocyst of an animal (e.g., a mouse) to form aggregation chimeras (see e.g., Bradley, A., in Teratocarcinomas and Embryonic Stem Cells: A Practical Approach, Robertson, E. J. ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) Curr. Opin. Biotechnol 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of Saccharomyces cerevisiae (O'Gorman et al. (1991) Science 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The G2BD nucleic acid molecules, proteins, fragments thereof, anti-G2BD antibodies, and G2BD modulators (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a G2BD protein or a G2BD modulator) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fluidics acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, peptidomimetic, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of G2BD activity is administered in combination with other agents (e.g., a small molecule), or in conjunction with another, complementary treatment regime. For example, in one embodiment, a modulator of G2BD activity is used to treat an ERAD associated disorder (e.g., cancer). Accordingly, modulation of G2BD activity may be used in conjunction with, for example, another agent used to treat the disorder. For example, non-limiting examples of agents used to treat ERAD associated disorders include, but are not limited to, chemotherapeutic agents and radiation.

Further, a G2BD protein or peptidomimetic (or fragment thereof), or a G2BD specific antibody, may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunirubicin, dihydroxy anthracin dione, mitoxantrone, mithraniycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNUT) and lomustine (CCNU), cyclophosphamide, busulfan, dibromomannitol, streptozotocin, mitomycin C, and cis-dichlorodianiine platinum (ID) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al. "Monoclonal Antibodies For Immunotargeting Of Drugs In Cancer Therapy" in Monoclonal Antibodies And Cancer Therapy, Reisfeld et al. (eds.), pp. 243-56 (Alan R. Liss, Inc. 1985); Hellstrom et al. "Antibodies For Drug Delivery" in Controlled Drug Delivery (2nd Ed.), Robinson et al. (eds.), pp. 623-53 (Marcel Dekker, Inc. 1987); Thorpe "Antibody Carriers Of Cytotoxic Agents In Cancer Therapy: A Review" in Monoclonal Antibodies'84: Biological And Clinical Applications, Pinchera et al. (eds.), pp. 475-506 (1985); "Analysis, Results, And Future Prospective Of The Therapeutic Use Of Radiolabeled Antibody In Cancer Therapy" in Monoclonal Antibodies For Cancer Detection And Therapy, Baldwin et al. (eds.), pp. 303-16 (Academic Press 1985); and Thorpe et al. "The Preparation And Cytotoxic Properties Of Antibody-Toxin Conjugates" Immunol Rev. 62:119-58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, protein fragments, antibodies, peptides, peptidomimetics, and small molecules described herein can be used in one or more of the following methods: a) screening assays; b) predictive medicine (e.g., diagnostic assays, prognostic assays, and monitoring clinical trials); and c) methods of treatment (e.g., therapeutic and prophylactic). As described herein, a G2BD protein of the invention has one or more of the following activities: (i) interaction with a target molecule such as Ube2G2; (ii) modulation of Ube2G2 activity; (iii) modulation of ERAD; (iv) modulation of intra- or inter-cellular signaling and/or gene transcription (e.g.; either directly or indirectly); (v) modulation of protein stability (e.g., CD3-δ and/or TCR stability); and/or (vi) modulating of tumor metastasis and/or invasiveness.

The isolated nucleic acid molecules of the invention can be used, for example, to express G2BD protein (e.g., via a recombinant expression vector in a host cell in gene therapy applications), to detect gp78 mRNA (e.g., in a biological sample) or a genetic alteration in a G2BD, to modulate G2BD activity, and to modulate ERAD, as described further below. The G2BD proteins can be used to treat disorders characterized by insufficient or excessive ERAD or insufficient or excessive stability of a particular protein, for example, ERAD associated disorders.

In addition, the G2BD proteins can be used to screen for naturally occurring G2BD target molecules, to screen for drugs or compounds which modulate G2BD activity, as well as to treat disorders characterized by insufficient or excessive ERAD or insufficient or excessive stability of a particular protein (e.g., an ERAD associated disorder).

Moreover, the G2BD proteins and peptidomimetics of the invention can be used to detect and isolate Ube2G2 proteins, regulate the bioavailability of Ube2G2 proteins, and modulate Ube2G2 activity.

A. Screening Assays

The invention provides a method (also referred to herein as a "screening assay") for identifying modulators, i.e., candidate or test compounds or agents (e.g., peptides, peptidomimetics, small molecules or other drugs) which bind to G2BD proteins, have a stimulatory or inhibitory effect on, for example, gp78 expression or G2BD activity, or have a stimulatory or inhibitory effect on, for example, the expression or activity of a G2BD target molecule (e.g., Ube2G2).

In one embodiment, the invention provides assays for screening candidate or test compounds which bind to a G2BD protein or polypeptide or biologically active portion thereof. In another embodiment, the invention provides assays for screening candidate or test compounds which bind to or modulate the activity of a G2BD protein or polypeptide or biologically active portion thereof, e.g., by interfering with the interaction between G2BD and Ube2G2. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:45).

Examples of methods for the synthesis of molecular libraries can be found in the art, for example, in: DeWitt et al. (1993) Proc. Natl. Acad. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404406); (Cwirla et al. (1990) Proc.

Natl. Acad. Sci. USA 87:6378-6382); (Felici (1991) J. Mol. Biol. 222:301-310); (Ladner supra.).

In one embodiment, an assay is a cell-based assay in which a cell which expresses a G2BD protein or biologically active portion thereof is contacted with a test compound and the ability of the test compound to modulate G2BD activity is determined. Determining the ability of the test compound to modulate G2BD activity can be accomplished by monitoring, for example: (i) interaction with a target molecule such as Ube2G2; (ii) modulation of Ube2G2 activity; (iii) modulation of ERAD; (iv) modulation of intra- or inter-cellular signaling and/or gene transcription (e.g., either directly or indirectly); (v) modulation of protein stability (e.g., CD3-δ and/or TCR stability); and/or (vi) modulating of tumor metastasis and/or invasiveness.

Methods for determining the ability of the test compound to modulate Ube2G2 activity and/or ERAD activity can be found in Fang, S. et al. (2001) Proc. Natl. Acad. Sci. USA 98:14422-14427; and Tiwari, N. and Weissman, A. (2001) J. Biol. Chem. 276:16193-16200, both of which are incorporated herein by reference.

The ability of the test compound to modulate G2BD binding to a target molecule (e.g., Ube2G2) can also be determined. Determining the ability of the test compound to modulate G2BD binding to a target molecule can be accomplished, for example, by coupling the G2BD target molecule with a radioisotope or enzymatic label such that binding of the G2BD target moelecule to G2BD can be determined by detecting the labeled G2BD target molecule in a complex. Alternatively, G2BD can be coupled with a radioisotope or enzymatic label to monitor the ability of a test compound to modulate G2BD binding to a G2BD target molecule in a complex. Determining the ability of the test compound to bind G2BD can be accomplished, for example, by coupling the compound with a radioisotope or enzymatic label such that binding of the compound to G2BD can be determined by detecting the labeled G2BD compound in a complex. For example, compounds (e.g., G2BD target molecules) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g, a G2BD target molecule) to interact with G2BD without the labeling of any of the interactants. For example, a microphysiometer can be used to detect the interaction of a compound with G2BD without the labeling of either the compound or the G2BD. McConnell, H. M. et al. (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and G2BD.

In another embodiment, an assay is a cell-based assay comprising contacting a cell expressing a G2BD target molecule (e.g., Ube2B2) with a test compound and determining the ability of the test compound to modulate (e.g., stimulate or inhibit) the activity of the G2BD target molecule. Determining the ability of the test compound to modulate the activity of a G2BD target molecule can be accomplished, for example, by determining the ability of a G2BD protein to bind to or interact with the G2BD target molecule or by determining the ability to modulate the activity of the G2BD target molecule (e.g., by measuring the stability of a protein such as CD3-δ or TCR-α.

In yet another embodiment, an assay of the present invention is a cell-free assay in which a G2BD protein or biologically active portion thereof is contacted with a test compound and the ability of the test compound to bind to the G2BD protein or biologically active portion thereof is determined. Preferred biologically active portions of the G2BD proteins to be used in assays of the present invention include fragments which participate in interactions with non-G2BD molecules, e.g., a minimal G2BD. Binding of the test compound to the G2BD protein can be determined either directly or indirectly as described above. In a preferred embodiment, the assay includes contacting the G2BD protein or biologically active portion thereof with a known compound which binds G2BD (e.g., a Ube2G2 protein) to form an assay mixture, contacting the assay mixture with a test compound, and determining the ability of the test compound to interact with a G2BD protein, wherein determining the ability of the test compound to interact with a G2BD protein comprises determining the ability of the test compound to preferentially bind to G2BD or biologically active portion thereof as compared to the known compound.

In another embodiment, the assay is a cell-free assay in which a G2BD protein or biologically active portion thereof is contacted with a test compound and the ability of the test compound to modulate (e.g., stimulate or inhibit) the activity of the G2BD protein or biologically active portion thereof is determined. Determining the ability of the test compound to modulate the activity of a G2BD protein can be accomplished, for example, by determining the ability of the G2BD protein to bind to a G2BD target molecule (e.g., Ube2G2) by one of the methods described above for determining direct binding. Determining the ability of the G2BD protein to bind to a G2BD target molecule can also be accomplished using a technology such as real-time Biomolecular Interaction Analysis (BIA). Sjolander, S. and Urbaniczky, C. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a G2BD protein can be accomplished by determining the ability of the G2BD protein to further modulate the activity of a downstream effector of a G2BD target molecule. For example, the activity of the effector molecule on an appropriate target can be determined or the binding of the effector to an appropriate target can be determined as previously described.

In yet another embodiment, the cell-free assay involves contacting a G2BD protein or biologically active portion thereof with a known compound which binds the G2BD protein (e.g., Ube2G2) to form an assay mixture, contacting the assay mixture with a test compound, and determining the ability of the test compound to interact with the G2BD protein, wherein determining the ability of the test compound to interact with the G2BD protein comprises determining the ability of the G2BD protein to preferentially bind to or modulate the activity of a G2BD target molecule.

The cell-free assays of the present invention are amenable to use of both soluble and/or membrane-bound forms of isolated proteins (e.g., G2BD proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether).sub.n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either G2BD or its target molecule to facilitate separation of complexed from uncomplexed forms of one or both of the proteins, as well as to accommodate automation of the assay. Binding of a test compound to a G2BD protein, or interaction of a G2BD protein with a substrate or target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/G2BD fusion proteins or glutathione-S-transfera-se/target fusion proteins can be adsorbed onto glutathione sepharose beads (Sigma Chemical, St. Louis, Mo.) or glutathione derivatized micrometer plates, which are then combined with the test compound or the test compound and either the non-adsorbed target protein or G2BD protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of G2BD binding or activity determined using standard techniques.

Other techniques for immobilizing proteins on matrices can also be used in the screening assays of the invention. For example, either a G2BD protein or a G2BD substrate or target molecule can be immobilized utilizing conjugation of biotin and streptavidin. Biotinylated G2BD protein, substrates, or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with G2BD protein or target molecules but which do not interfere with binding of the G2BD protein to its target molecule can be derivatized to the wells of the plate, and unbound target or G2BD protein trapped in the wells by antibody conjugation. Methods for detecting such complexes, in addition to those described above for the GST-immobilized complexes, include immunodetection of complexes using antibodies reactive with the G2BD protein or target molecule, as well as enzyme-liked assays which rely on detecting an enzymatic activity associated with the G2BD protein or target molecule.

In yet another aspect of the invention, the G2BD proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300) to identify other proteins which bind to or interact with G2BD ("G2BD-binding proteins" or "G2BD-bp") and are involved in G2BD activity. Such G2BD-binding proteins are also likely to be involved in the propagation of signals by the G2BD proteins or G2BD targets as, for example, downstream elements of a G2BD-mediated signaling pathway. Alternatively, such G2BD-binding proteins may be G2BD inhibitors. In another embodiment, such G2BD binding proteins are likely to be ubiquitin conjugating enzymes.

The two-hybrid system is based on the modular nature of most transcription factors, which consist of separable DNA-binding and activation domains. Briefly, the assay utilizes two different DNA constructs. In one construct, the gene that codes for a G2BD protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a G2BD-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the G2BD protein.

In another aspect, the invention pertains to a combination of two or more of the assays described herein. For example, a modulating agent can be identified using a cell-based or a cell-free assay, and the ability of the agent to modulate the activity of a G2BD protein can be confirmed in vivo, e.g., in an animal such as an animal model for tumor metastasis and/or invasivness, as well as animal models for other ERAD associated disorders.

This invention further pertains to novel agents identified by the above-described screening assays. Accordingly, it is within the scope of this invention to further use an agent identified as described herein in an appropriate animal model (e.g., an animal model such as any of those described above). For example, an agent identified as described herein (e.g., a G2BD protein, a G2BD modulating agent or a G2BD peptidomimetic) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the DNA and polypeptide sequences identified herein can be used in numerous ways as polynucleotide and polypeptide reagents. For example, these sequences can be used to detect G2BD DNA or Ube2G2 protein in a biological sample.

An exemplary method for detecting the presence or absence of Ub2G2 protein, in a biological sample involves obtaining a biological sample from a test subject (or cell culture) and contacting the biological sample with a detectably labeled G2BD protein of the invention such that the presence of Ube2G2 protein or nucleic acid is detected in the biological sample. In another aspect, the present invention provides a method for detecting the presence of G2BD activity in a biological sample by contacting the biological sample with an agent capable of detecting an indicator of G2BD activity such that the presence of G2BD activity is detected in the biological sample.

A preferred agent for detecting G2BD protein is an antibody capable of binding to G2BD protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect G2BD mRNA, protein, or genomic DNA in a biological sample in vitro as well as in vivo. For example, in vitro techniques for detection of G2BD mRNA include Northern hybridizations and in situ hybridizations. In vitro techniques for detection of G2BD protein include enzyme linked immunosorbent assays (ELISAs), Western blots, immunoprecipitations and immunofluorescence. In vitro techniques for detection of G2BD genomic DNA include Southern hybridizations. Furthermore, in vivo techniques for detection of a G2BD protein include introducing into a subject a labeled anti-G2BD antibody. For example, the antibody can be labeled with a radioactive marker whose presence and location in a subject can be detected by standard imaging techniques.

The invention also encompasses kits for detecting she presence of G2BD or Ube2G2 in a biological sample. For example, the kit can comprise a labeled compound or agent capable of detecting G2BD protein or mRNA or Ube2G2 protein in a biological sample; means for determining the amount of G2BD protein or mRNA or Ube2G2 protein in the sample; and means for comparing the amount of G2BD protein or MRNA or Ube2G2 protein in the sample with a standard. The compound or agent can be packaged in a suitable container. The kit can further comprise instructions for using the kit to detect G2BD protein or mRNA, or Ube2G2 protein.

As used herein, a "biological sample" is a cell, tissue, and/or biological fluid sample isolated from a subject by conventional means. A biological sample may include cells, tissues, and biological fluid, or any combination thereof. A biological sample also includes a sample of cells or tissue grown in cell culture. Any cell type or tissue in which G2BD is expressed may be utilized in the assays described herein.

C. Methods of Treatment

The present invention provides for both prophylactic and therapeutic methods of treating a subject at risk of (or susceptible to) or having an ERAD associated disorder, e.g., a disorder associated with aberrant or unwanted G2BD expression or activity (e.g., hypertension or atherosclerosis). As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose of curing, healing, alleviating, relieving, altering, remedying, ameliorating, improving, or affecting the disease or disorder, the symptom of the disease or disorder, or the risk of (or susceptibility to) the disease or disorder. As used herein, a "therapeutic agent" includes, but is not limited to, small molecules, peptides, polypeptides, peptidomimetics, antibodies, ribozymes, and antisense oligonucleotides.

In one aspect, the invention provides a method for preventing in a subject, an ERAD associated disorder, by administering to the subject a G2BD protein or an agent which modulates at least one G2BD activity (e.g., interaction with Ube2G2). Subjects at risk for a disease which is caused or contributed to by aberrant or unwanted G2BD expression or activity can be identified by, for example, according to methods known in the art. Administration of a prophylactic agent can occur prior to the manifestation of symptoms characteristic of the ERAD associated disorder, such that the disease or disorder is prevented or, alternatively, delayed in its progression. Depending on the type of G2BD aberrancy, for example, a G2BD molecule, G2BD agonist or G2BD antagonist agent can be used for treating the subject. The appropriate agent can be determined based on screening assays described herein.

Another aspect of the invention pertains to methods of modulating G2BD activity for therapeutic purposes. Accordingly, in an exemplary embodiment, the modulatory method of the invention involves contacting a cell capable of expressing G2BD with an agent that modulates one or more of the activities of G2BD protein activity associated with the cell, such that G2BD activity in the cell is modulated. An agent that modulates G2BD protein activity can be an agent as described herein, such as a G2BD nucleic acid or a protein, a naturally-occurring target molecule of a G2BD protein (e.g., a G2BD target molecule such as Ube2G2), a G2BD antibody, a G2BD agonist or antagonist, a peptidomimetic of a G2BD agonist or antagonist, or other small molecule. In one embodiment, the agent stimulates one or more G2BD activities. Examples of such stimulatory agents include active G2BD protein and a nucleic acid molecule encoding G2BD that has been introduced into the cell. In another embodiment, the agent inhibits one or more G2BD activities. Examples of such inhibitory agents include antisense G2BD nucleic acid molecules, anti-G2BD antibodies, and G2BD inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a G2BD protein or nucleic acid molecule. In one embodiment, the method involves administering an agent (e.g., an agent identified by a screening assay described herein), or combination of agents that modulates (e.g., upregulates or downregulates) G2BD expression or activity. In another embodiment, the method involves administering a G2BD protein or nucleic acid molecule as therapy to compensate for reduced, aberrant, or unwanted G2BD expression or activity.

Stimulation of endogenous G2BD activity is desirable in situations in which increased G2BD activity is likely to have a beneficial effect. For example, stimulation of G2BD activity is desirable in situations in which it is desirable to upregulate ERAD. For example, it is desirable to upregulate ERAD in cells where it would be beneficial to decrease the stability of a protein that is normally degraded by ERAD. Stimulation of the activity of an exogenous G2BD (e.g., a G2BD polypeptide used to treat a subject) results in inhibition of ERAD via binding to cellular Ube2G2.

Inhibition of endogenous G2BD activity is desirable in situations in which decreased G2BD activity is likely to have a beneficial effect. For example inhibition of G2BD activity is desirable in situations in which it is desirable to downregulate ERAD. For example, it is desirable to downregulate ERAD in cells where it would be beneficial to increase the stability of a protein that is normally degraded by ERAD. In another embodiment, it is desirable to downregulate ERAD in cancer cells, because downregulation of ERAD may induce cellular stress, which in turn induces apoptosis of the cancer cells.

This invention is further illustrated by the following examples which should not be construed as limiting. The contents of all references, patents and published patent applications cited throughout this application, as well as the sequence listing and the figures, are incorporated herein by reference.

EXAMPLES

Experimental Procedures

The following experimental procedures were used in the Examples, unless otherwise indicated.

Cells and Antibodies

HT1080 (ATCC Accession No. CCL-121), HEK 293T (ATCC Accession No. CRL-11268) and NIH 3T3 (ATCC Accession No. CRL-1658) were maintained in DMEM with 10% fetal bovine serum, J558 (ATCC Accession No. TIB-6) was maintained in DMEM with 10% horse serum. Anti-Myc (9E10) and Flag (F3165) antibodies were from Sigma (St, Louis, Mo.); anti-CHOP was from Biovision (3421-100); anti-BiP was from BD Pharmingen (610979); and anti-phospho-eIF2α was from Abcam (ab4837). Anti-GFP (sc-9996), actin (sc-1616), His6 (sc-803), eIF2α (sc-11386) and ubiquitin (sc-9133) were from Santa Cruz Biotechnology (Santa Cruz, Calif.). Rabbit antisera against gp78 (Fang et al., 2001), UbcH5B and ubiquitin (Lorick et al., 1999) as well as monoclonal TCR-α antibodies H28-710 (Takata et al., 1990) and A2B4-2 (Samelson et al., 1983) have been described. Polyclonal rabbit antisera for MmUBC7/Ube2G2, Ube2g1 and hHRD1 were raised against peptides corresponding to amino acid residues 148-165, 160-170 and 493-509 respectively. Antibody purification and biotinylation was by standard methods.

Plasmids

Plasmids encoding the following have been described: rat Ubc7 (Ube2g1) (Lin and Wing, 1999); UbcH5B (Jensen et al., 1995); Myc-MmUbc7, C89S Myc-MmUbc7, HA-CD3-δ and 2B4 TCR-α (Tiwari and Weissman, 2001); GST-gp78 309 to 643, 508 or 428 and full length gp78 and the double RING finger mutation gp78Rf-m in pCINeo (Fang et al., 2001); and GST-UBA-Cbl-b (Davies et al., 2004). Plasmids encoding Ubc7p and His6-MmUbc7 were generated by PCR and subcloned into pCDNA-DEST47 or pExp17 respectively using Gateway (Invitrogen, Carlsbad, Calif.). GST-AO7 (92 to 259) was subcloned from full length A07 (Lorick et al., 1999). GST-gp78 beginning at 429, 503, 522, 542, 561, 574, 587, or 596 and ending at 643 GST-gp78 beginning at 435 and ending at 507 and GST-Cue1p 24-203 (Cue1pC) were generated by PCR and cloning into pGEX4T-1 (Amersham Biosciences, Piscataway, N.J.). N-terminal Flag-tagged constructs were created by PCR and cloning into pFlag-CMV6 (Sigma). N-terminal GFP-tagged constructs were generated by subcloning from pFLAG-CMV6 to pEGFP-C1 (BD Biosciences, Palo Alto, Calif.). Introduction of missense or nonsense mutations was by sitespecific mutagenesis. All mutated plasmids were sequenced. Oligonucleotide sequences are available upon request.

Hairpin siRNAs against sequences in human AMFR/gp78 correspond to coding sequence bases 636-656 (gp78-si1) and 318-336 (gp78-si2) and Ube2G2 siRNA corresponds to bases 391-411 (Ube2G2-si1). Oligonucleotides were cloned into pSuper (OligoEngine, Seattle, Wash.). Negative control siRNA provided with pSilencer (Ambion, Austin, Tex.) that corresponds to a sequence not found in the mouse, human or rat genomic database was also subcloned into pSuper.

Binding Assays

GST fusions were purified from *E. Coli*. Binding was carried out using equi-molar amount of fusion proteins measured by Commassie blue staining. Generally, 20 picomoles/sample were used. In vitro translated E2 was generated by coupled transcription and translation using 35S methionine in either wheat germ or rabbit reticulocyte lysate. Binding assays using in vitro translated E2 was carried out by incubating GST protein pre-bound to Glutathione-sepharose 4B with 105 cpm of $^{35}$S-methionine labeled E2 in binding buffer (25 mM Tris-HCl, pH 7.4; 50 mM NaCl, 5 mM DTT; and 0.5% NP-40) overnight at 4° C. Beads were washed with binding buffer and resolved by SDS-PAGE under reducing conditions. Analysis was by Storm PhosphoImager (Applied Biosystems, Foster City, Calif.). Direct binding assays used wild type His6-MmUbc7 (His6-Ube2G2) and Glutathione-sepharose bound GST fusions. Beadbound GST protein was incubated with 100 ng purified His6-MmUbc7 in binding buffer and washed and eluted as above. After transfer to Hybond-P (Amersham Biosciences) binding was assessed with anti-His6 followed by Enhanced Chemiluminescence ECL; Pierce). Ubiquitin binding studies were performed with binding and washing as above using 1 μg K48 tetra-ubiquitin produced as described (Piotrowski et al., 1997). Detection was by anti-ubiquitin immunoblotting.

Transfection Studies

Transfections of HT1080, NIH 3T3 and HEK 293T cells were carried out ~24 hr after plating using Polyfect (Qiagen, Valencia, Calif.) and cells harvested after ~48 hr. J558 cells were transfected by electroporation using Bio-rad GENE pulser II at settings of 250 v, 950uF. Vector without insert was used to equalize total plasmid. In most experiments 0.15 μg of pEGFP-C1 served as an internal control. For experiments not involving immunoprecipitation, 6×105 cells were plated in 6 well plates and cell lysis was with Mammalian Protein Extraction Reagent (Pierce). For immunoprecipitation, 2.4× 106 cells were seeded in 100 mm dishes and cells were lysed in RIPA buffer (1×PBS, 1% Nonidet P40. 0.5% sodium deoxycholate, 0.1% SDS). Lysis buffers were supplemented with Protease Inhibitor Cocktail (Sigma) and 10 mM iodoacetamide. Supernatants were analyzed after a 10,000×g centrifugation using standard techniques for immunoprecipitation, SDS-PAGE, immunoblotting and ECL. Treatment of cells with MG132 (Sigma) was at 50 μM for eight hr. Cycloheximnide was used at 50 μg/ml. All cells were collected at the end of the six hr chase.

Flow Cytometry 24 hr after transfection with constructs encoding GFP or GFP fusion proteins, cells were stained with annexin V-PE (BD Pharmingen) and analyzed on a Beckman coulter XL. Data for J558 was average of three experiments, NIH 3T3 was from 2 experiments. Gates were set to analyze cells expressing GFP using 525 band-pass filter and evaluated for annexin V-PE staining using a 575 band-pass filter. To isolate cells expressing GFP, J558 cells were harvested 24 hr after transfection and sorted on a BD FACS Aria. Transfection efficiencies were 7-10%. 2×104 cells expressing GFP fusions were isolated.

Example 1 gp78 Selectively Binds UBE2G2/MmUbc7 in GST Pull Down Assays

In FIG. 2, equal amounts of GST fusion proteins encoding the cytoplasmic tail of gp78 (gp78C; amino acid residues 309-643 of SEQ ID NO:2), the cytoplasmic tail beginning after the RING finger (gp78CAR; amino acid residues 429-643 of SEQ ID NO:2), the RING finger and surrounding regions of the unrelated E3 enzyme AO7, and the cytoplasmic tail of the yeast protein Cue1p (which has some homology to gp78) were compared to GST for their ability to bind the E2 enzymes indicated on the left side of FIG. 2. Ube2G1 is the closest family member of Ube2G2. Ubc7p is a yeast protein. UbcH5B is a generic E2 enzyme. The E2 enzymes were in vitro translated using wheat germ.

Despite some similarity between Cue1p and gp78C gp78CΔR, only regions containing the gp78 tail bound the mammalian ERAD E2 Ube2G2/MmUbc7. Neither the closest human relative Ube2G1 nor the UbcH5B bound to gp78. Similar results were obtained for E2s translated in reticulocyte lysate.

Example 2

Localization of The G2BD In Vitro

FIGS. 3A-3C depict the binding of MmUbc7/Ube2G2 deletion mutants to gp78 in GST pull-down assays. GST fusion proteins encoding the regions indicated in FIGS. 3A-3C were evaluated for the ability to bind to Ube2G2/MmUbc7 that had been in vitro transcribed and translated in rabbit reticulocyte lysate. gp78C represents the entire C-terminal cytoplasmic domain of gp78 (amino acid residues 309-643 of SEQ ID NO:2). As is evident, the region from amino acid residues 574-608 was sufficient for binding to Ube2G2.

FIG. 4A-4B depict binding of Ube2G2/MmUbc7 mutants to gp78 in GST pull-down assays. Binding studies were carried out as in FIGS. 3A-3C using the fusion proteins indicated. Amino acid ranges are relative to SEQ ID NO:2. Mutations are represented by Δ and are as follows: ΔRK1: mutated residues 585-586 to AA; ΔQQ: mutated residues 591-592 to AA; ΔRK2: mutated residues 594-595 to AA; ΔA: mutated residues 574-578 (SADER; SEQ ID NO:5) to AAAAG (SEQ ID NO:6); and ΔB: mutated residues 579-584 (QRMLVQ; SEQ ID NO:10) to AAAGGG (SEQ ID NO:8). The ΔB mutation results in the loss of binding to Ube2G; however, amino acid residues 574-578 appear to be dispensible.

FIG. 5 depicts the results of immunoprecipitation of Ube2G2 (MmUbc7) from HEK 293T cells co-transfected with a plasmid encoding myc-tagged MmUbc7/Ube2G2 together with s plasmid encoding various forms of gp78. HEK 293T cells were transfected with a plasmid encoding myc-tagged MmUbc7/Ube2G2 together with plasmids encoding various forms of gp78. After 48 hours, cells were harvested and co-immuntoprecipitated with an anti-Myc tage. Anti-gp78 was used for detection. "R2M" indicates a mutation of two crucial residues in the RING finger. "T" indicates C terminal truncations at the indicated amino acids. ΔB is the mutation indicated above in FIG. 4 in the context of the full length gp78 and "Cue12M" indicates mutations in the Cue domain of gp78.

FIG. 6 depicts the specific binding of gp78 residues 574-611 (of SEQ ID NO:2) to endogenous Ube2G2 in HEK 293T cells. Cells were transfected with plasmids encoding GFP fusions of the indicated regions of gp78, and co-immunoprecipitation was evaluated. Input is shown on the right. The region from amino acid residues 574-611 of SEQ ID NO:2 is sufficient to co-immunoprecipitate endogenous Ube2G2 from cells. However, its most closely-related mammalian relative, Ube2G1 (which is not implicated in ERAD) is not co-immunoprecipitated, nor is UbcH5B.

Example 3

The G2BD Stablizes Proteins In Cells

FIG. 7 depicts the stabilization of CD3-δ protein in cells transfected with the G2BD, but not with the G2BD with amino acids 579-584 (of SEQ ID NO:2) mutated. HEK 293T cells were transfected with the ERAD substrate CD3-δ along with the indicated GFP fusions of gp78. The left and right sides are two separate experiments. The region from residues 574-611 (of SEQ ID NO:2) is sufficient to stabilize CD3-δ. However, mutation of amino acid residues 579-584 results in a loss of this effect, correlating with the loss of binding to Ube2G2.

FIG. 8 depicts the reversal CD3-δ stabilization by exogenous Ube2G2 (MmUBC7). Cells were co-transfected with CD3-δ and with Flag-tagged gp78 residues 574-643 of SEQ ID NO:2 where indicated. In lanes 3-4 and 6-7, an increasing amount of plasmid encoding Ube2G2/MnUbc7 was co-transfected into the cells. The fact that this is reversed with co-expression of Ube2G2/MmUbc7 establishes a causal role for this association in its effect on ERAD.

FIG. 9 depicts the stabilization of endogenous TCRα by the G2BD. TCR-α is a subunit of the T cell antigent receptor and an ERAD substrate. TCR-α was stabilized by the region implicated in Ube2G2 binding. The stabilzation was comparable to that seen with the preoteosome inhibitor Mg132.

Example 4

Endogenous gp78 And Ube2G2 Are Important For ERAD Function

To determine the significance of endogenous Ube2G2 and gp78 in ERAD, siRNA constructs specific for human gp78 (gp78-si1 and gp78-si2) or Ube2G2 (Ube2G2-si1) were evaluated. The specificity of these siRNAs was validated by the loss of expression of their targets but not of their closest human relatives, hHrd1 and Ube2g1 respectively (FIGS. 16A and 16B). Each of these siRNAs resulted in a marked increase in CD3-δ (FIG. 16A, top panel) while a control siRNA was without effect (lane 2). Similarly, siRNAs against gp78 and Ube2G2 also resulted in the marked stabilization of a second ERAD substrate, TCR-α (FIG. 16B, top panel). This is the first demonstration that TCR-α can be regulated by gp78. These data establish important roles for both endogenous gp78 and Ube2G2 in ERAD for multiple substrates.

Example 5

The gp78 Cue Domain, But Not Yeast Cue1p, Binds Tetra-Ubiquitin gp78 includes at least five membrane-spanning domains followed by a predicted 341 amino acid cytoplasmic tail that includes a RING finger and a region identified as a Cue domain (FIG. 17A). There is also evidence for RING finger-independent E2 binding within the cytoplasmic tail (Fang et al., 2001). To begin to understand the molecular requirements for gp78's function, the Cue domain was evaluated for ubiquitin binding.

As demonstrated in FIG. 17B, a GST fusion of the entire gp78 cytoplasmic tail (gp78C) binds the proteasome targeting signal lysine 48-linked (K48) tetra-ubiquitin (Thrower et al., 2000) as does an N-terminal truncated version that lacks the RING finger but retains the Cue domain (429-643 of SEQ ID NO:2). In contrast, no binding of tetra-ubiquitin to the cytoplasmic domain of yeast Cue1p (Cue1pC) was observed. As previously reported (Davies et al., 2004) the UBA of the RING finger E3, Cbl-b (UBA-Cbl-b) also binds tetra-ubiquitin.

Based on sequences predicted to be important for ubiquitin binding by Vsp9p and Cue2p (Kang et al., 2003; Prag et al., 2003), two sets of mutations were generated in the gp78 Cue domain. Either of these, Cue-m1 and Cue-m2, resulted in the total loss of ubiquitin binding, as did the combination (Cue-m1, 2). The gp78 Cue domain region (435-507 of SEQ ID NO:2) was also sufficient to bind tetra-ubiquitin (FIG. 17C). Thus, the gp78 Cue domain directly binds ubiquitin chains.

Example 6

Defining The Ube2G2 Binding Region in gp78 in Vitro And in Cells

The molecular requirements for binding of gp78 to Ube2G2 were determined through a series of GST fusions of truncations of the cytoplasmic domain of gp78. A schematic and a summary of results is shown in FIG. 18A. Amino acids 574-608 of gp78 (SEQ ID NO:2) bound in vitro translated Ube2G2 comparably to the complete gp78 C-terminal tail (FIGS. 18B, lanes 3 and 4) and was the only region within the gp78 cytoplasmic domain that bound Ube2G2 (FIG. 18A). Amino acids distal to 600 were dispensable for binding (FIG. 18B lane 6).

The E2 binding site was further assessed by site-directed mutagenesis, which was largely guided by similarities to Cue1p within the E2 binding region of gp78, since Cue1p has been shown to bind Ubc7p (Biederer et al., 1997) (FIG. 18A bottom). Mutations of either of two RK dimers (E2-m3 and E2-m5) within gp78C that are conserved in Cue1p did not disrupt binding. Additionally, mutation of a QQ pair that aligns with a WQ in Cue1p (E2-m4) was without effect as was mutation of a five amino acid region from residues 574 to 578 of SEQ ID NO:2 (E2-m1) where there is similarity with Cue1p. Strikingly, the only mutation that resulted in loss of binding was a six amino acid stretch (residues 579-584 of SEQ ID NO:2) that corresponds to a gap in the alignment between gp78 and Cue1p (E2-m2) (FIGS. 18A and 18B). To establish whether the binding of Ube2G2 to gp78 is direct, His6-tagged Ube2G2 was expressed in bacteria and purified. His6-Ube2G2 bound specifically to the region of gp78 implicated in E2 binding (FIG. 18C lane 4) and the E2-m2 mutation disrupted binding (lane 5).

The requirement for an amino sequence in gp78 not found in Cue1p for binding of Ube2G2 led us to further evaluate the specificity of gp78 for this E2 (FIG. 3D). As is evident, gp78 bound Ube2G2 independent of the presence of the RING finger domain (residues 429-643 of SEQ ID NO:2), but failed to exhibit discernable binding to either yeast Ubc7p or to Ube2g1. In contrast, yeast Cue1p showed less stringency in binding in that it bound both Ubc7p and Ube2G2. Again, no binding to Ube2g1, which has not been implicated as an ERAD, was observed. As an additional control a human E2, UbcH5B, which is unrelated to Ubc7p and its human relatives, bound to neither Cue1p nor to gp78 but did bind to the RING finger E3, AO7, as previously reported (Lorick et al., 1999). Thus, at least in vitro the E2 binding to gp78 is highly specific to Ube2G2.

To confirm the significance of the Ube2G2 binding site in cells, a variety of mutations and truncations of full-length gp78 were tested for binding of co-expressed Myc-Ube2G2 (FIG. 19A). Cells were treated with the proteasome inhibitor MG132 in an attempt to equalize levels of the various forms of gp78. These data establish that neither mutations of critical zinc coordinating residues in the RING finger (gp78Rf-m) nor mutations in the Cue domain (gp78Cue-m1, 2) affect E2 association (FIG. 19A lanes 4 and 9). In contrast, the mutation of gp78 (gp78E2-m2) that disrupts E2 binding in vitro and truncations within the identified E2 binding region after either amino acids 576 of SEQ ID NO:2 (gp78576) or 595 (gp78$_{595}$) resulted in loss of E2 binding (lanes 6, 8 and 10). In contrast, a truncation after residue 611 of SEQ ID NO:2, which leaves this region intact (gp78611), retained E2 binding (lane 7).

Figure 19:
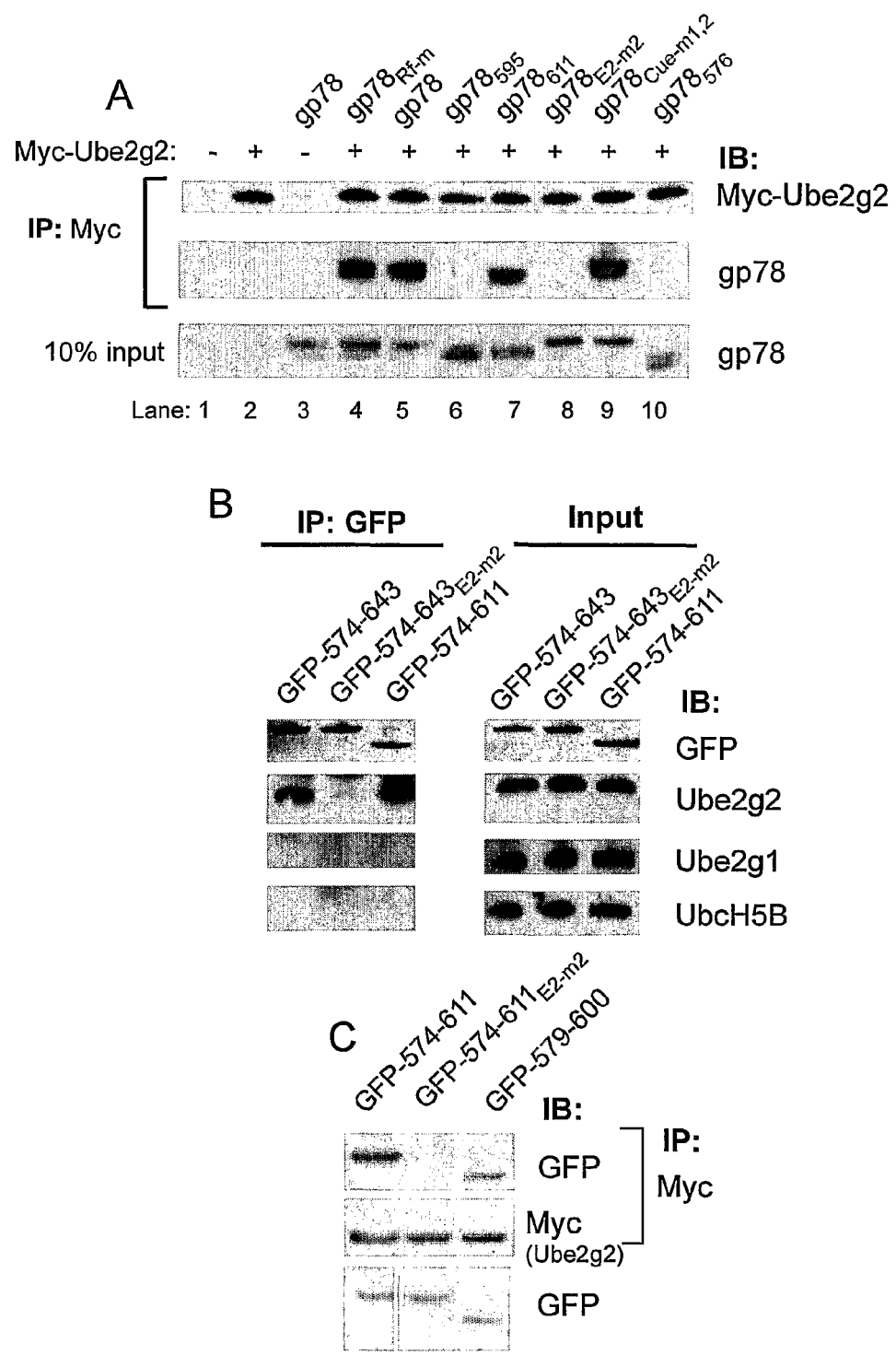
FIGS. 19A-19C depict the requirements for and specificity of gp78 binding to Ube2G2 in cells.

To determine the specificity of E2 binding in cells, GFP fusions encompassing the E2 binding region were expressed in cells, and co-immunoprecipitation of endogenous E2 was tested using antibodies raised specifically against Ube2g1, Ube2G2 and UbcH5B (FIG. 19B). Co-immunoprecipitation of endogenous Ube2G2 was easily detectable (second panel, left). In contrast, and consistent with the in vitro binding data in FIG. 18, no association with endogenous UbcH5B or Ube2g1 was detected (FIG. 19B third and fourth panels, left). The E2-m2 mutation abrogated binding. Additionally, consistent with the in vitro truncations and mutations, amino acids 579-600 of SEQ ID NO:2 (also set forth as SEQ ID NO:34) were found to be sufficient to bind Ube2G2 in cells (FIG. 19C). The results presented in FIGS. 18 and 19 define a unique and specific Ube2G2 binding site of 21 amino acids or less in gp78 that is independent of both the gp78 RING finger and Cue domain.

Example 7

Role Of The Ring Finger, Cue Domain, And Ube2G2 Binding Site In gp78 Function gp78 is degraded in a proteasome-dependent manner, and deletion of the entire cytoplasmic domain results in its stabilization. Similarly, CD3-δ ubiquitylation and proteasomal degradation is increased by co-expression of wild type gp78, and CD3-δ is stabilized by a gp78 RING finger mutant (Fang et al., 2001). To determine the significance of the RING finger, Cue domain and Ube2G2 binding site on gp78 stability, mutations of each were evaluated within full-length gp78. Mutations in the RING finger (gp78Rf-m), Cue domain (gp78Cue-ml, 2) or E2 binding site (gp78E2-m2) (FIG. 20A upper panel, lanes 3-5) each resulted in increased gp78 compared to wild type (lane 2). This implicates each of these as crucial in targeting gp78 for its own degradation. Consistent with gp78 targeting itself for ubiquitin-mediated proteasomal degradation, addition of the proteasome inhibitor MG132 stabilized wild type gp78 but had little effect on the various mutants. Accordingly, ubiquitylation was observed with wild type gp78 (FIG. 20B, upper panel lane 2), and each of the mutations resulted in a dramatic decrease in ubiquitin immunoreactivity. This further establishes the requirement for an intact RING finger, Cue domain and Ube2G2 binding site for gp78 to mediate its own proteasomal degradation.

Analysis of the effect of gp78 on CD3-δ (FIG. 20A, middle panel) demonstrates that, as described (Fang et al., 2001), wild type gp78 decreased CD3-δ levels compared to vector control while the RING finger mutation resulted in an increase in CD3-δ. Mutation of the Cue domain (gp78Cue-m1, 2) also resulted in a marked increase in CD3-δ (lane 4). This provides the first direct evidence for the importance of a ubiquitin binding domain in the activity of an E3. In contrast, expression of gp78 bearing a mutation of the E2 binding domain (gp78E2-m2) neither significantly stabilized CD3-δ nor enhanced its loss compared to vector control (compare lanes 5 and 1).

Figure 20:
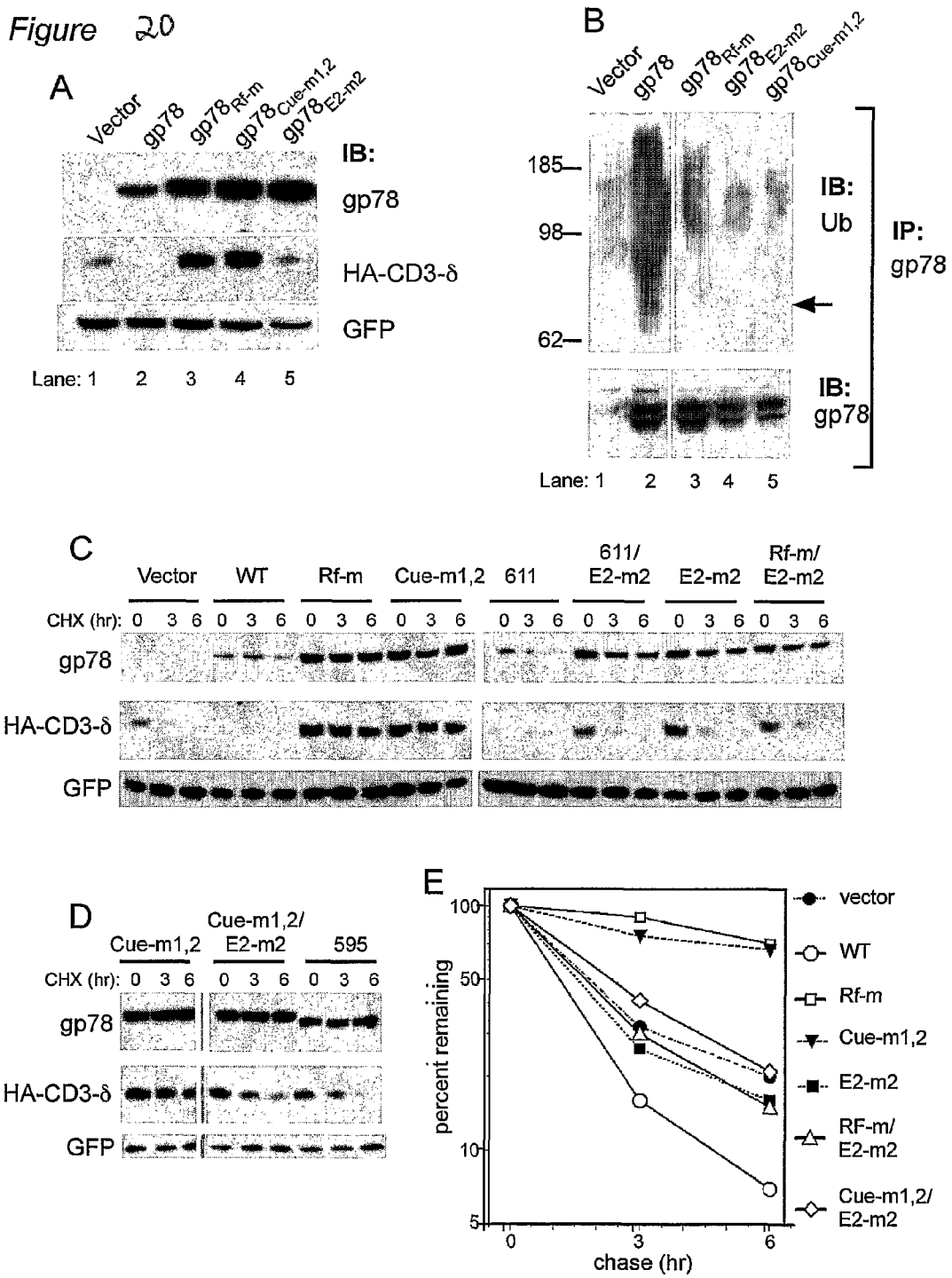
FIGS. 20A-20E depict the requirement of multiple domains of gp78 to target itself and a heterologous ERAD substrate.

To evaluate protein turnover in more detail, cycloheximide chase experiments were performed (FIGS. 20C and 20D). Consistent with FIG. 20A, when compared to wild type gp78 (WT), mutations in the RING finger (Rf-m), Cue domain (Cue-m1, 2) and E2 binding site (E2-m2) each stabilized gp78 (upper panels). Similarly, a truncation in which Ube2G2 binding is lost (595) stabilized gp78, while a truncation that retained E2 binding (611) did not stabilize gp78. A combination of mutations in the E2 binding site and either the RING finger (Rf-m/E2-m2) or Cue domain (Cue-m1, 2/E2-m2) also resulted in a failure of gp78 to effectively target itself for degradation. In agreement with FIG. 20A, CD3-δ degradation was accelerated with wild type gp78 (FIGS. 20C and 20D middle panels; effects of full-length forms of gp78 on CD3-δ from FIGS. 20C and 20D are quantified in FIG. 20E). Similar enhanced loss of CD3-δ was seen with the truncation at 611. In contrast, mutations in either the RING finger (Rf-m) or the Cue domain (Cue-m1, 2) resulted in a marked delay in CD3-δ loss. However, when the E2 binding domain was either truncated (595) or mutated either by itself (E2-m2), together with the RING mutation (Rf-m/E2-m2) or in the context of disruption of the Cue domain (Cue-m1, 2/E2-m2), there was minimal stabilization of CD3-δ.

These findings establish that self-regulation of gp78 requires an intact RING finger, an intact ubiquitin binding Cue domain and the capacity to recruit Ube2G2. Similarly, all three of these regions are required for gp78 to increase CD3-δ degradation. Expression of gp78 mutated in either the RING finger or Cue domain leads to enhanced accumulation of CD3-δ8. On the other hand, there is minimal effect on CD3-δ degradation with expression of gp78 in which the E2 binding site is interrupted, either by itself or together with the RING finger or Cue domain. These findings strongly suggest that the primary means by which RING finger and Cue domain mutants of gp78 inhibit ERAD is by binding Ube2G2 and preventing it from functioning with endogenous gp78 and possibly other ERAD E3s. When the capacity to bind Ube2G2 is disrupted the "dominant negative" effect is largely abrogated.

Example 8

Ube2G2/MmUBC7 Sequestration Effectively Blocks ERAD

Figure 21:
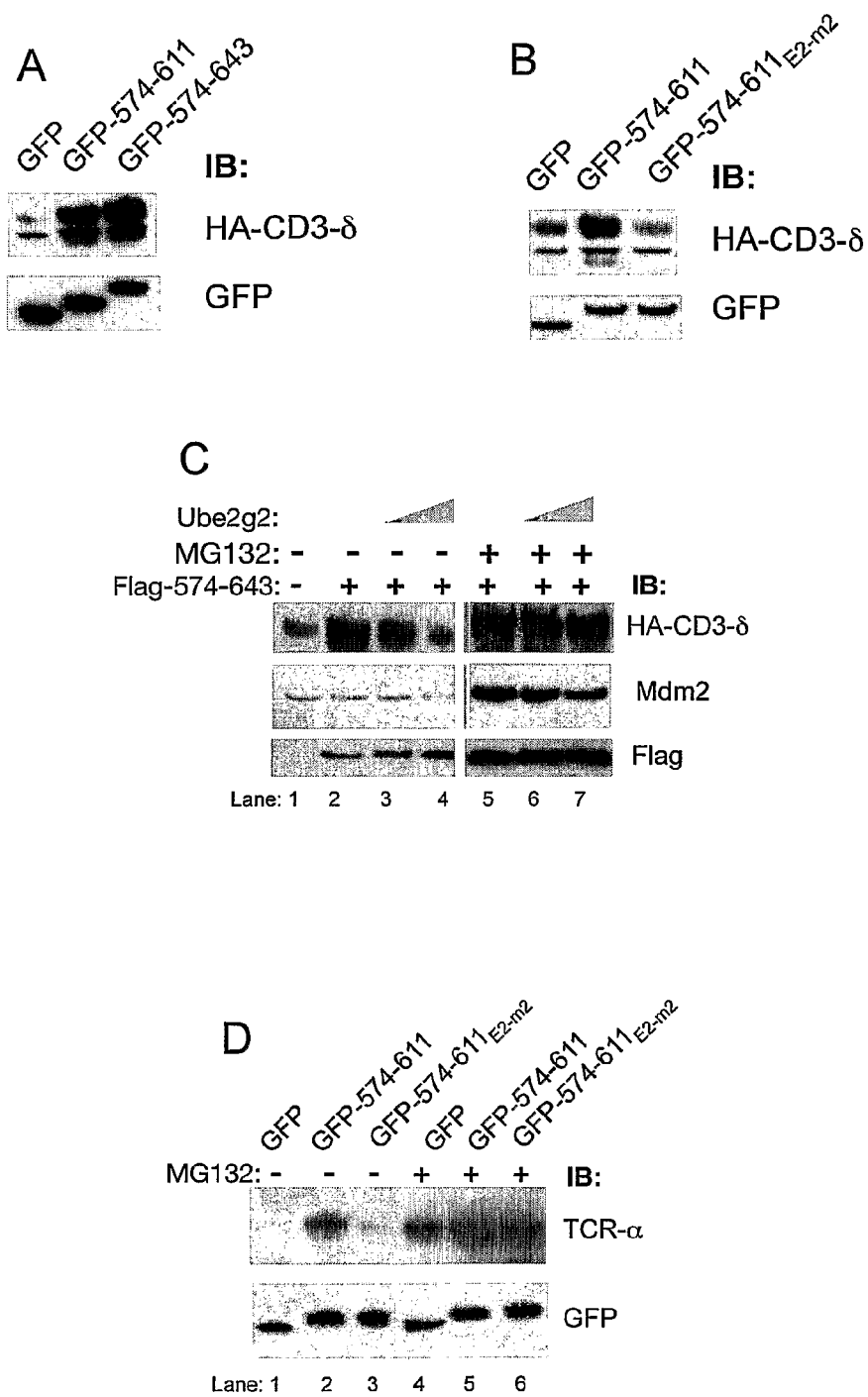
FIGS. 21A-21D depict the sequestration of E2 and blocking of ERAD by an isolated Ube2G2 binding site.

The profound inhibition of ERAD observed with mutation of either the gp78 RING finger or the Cue domain and the dependence of this inhibition on an intact Ube2G2 binding site suggests that the E2 binding region by itself might also inhibit ERAD. To test this, GFP fusions of either a minimal E2 binding domain (GFP-574-611) or a more extended region that includes the C-terminus of gp78 (GFP-574-643) were evaluated (FIG. 21A). Both of these dramatically stabilized CD3-δ, and mutation of the E2 binding site (GFP-574-611E2-m2) totally prevented this stabilization (FIG. 21B). To assess this further, the C-terminal region of gp78 was fused to the eight amino acid Flag tag. This resulted in marked stabilization of CD3-δ (FIG. 21C, upper panel compare lanes 1 and 2) but not of Mdm2 (FIG. 21C, middle panel). Mdm2 is a RING finger E3 for both itself and p53 that is neither an ERAD substrate nor known to utilize Ube2G2 as an E2. These results demonstrate the specificity of the E2 binding domain in stabilizing ERAD substrates. To establish with certainty that the effect observed with expression of the Ube2G2 binding site is a consequence of binding endogenous E2, and not due to other unanticipated effects, cells were co-transfected with increasing amounts of Ube2G2 (FIG. 21C, lanes 3 and 4). Consistent with sequestration of endogenous Ube2G2, a clear dose-dependent reversal of CD3-δ stabilization was observed. As expected, the proteasome inhibitor MG132 blocked the effect of transfected Ube2G2 (FIG. 21C, lanes 6 and 7) and also led to Mdm2 stabilization. These findings clearly establish that the isolated E2 binding site has the potential to markedly alter ERAD of CD3-δ. To ensure the effect observed was not peculiar to one substrate, TCR-α was evaluated (FIG. 21D).

Expression of the Ube2G2 binding site (lane 2) markedly stabilized TCR-α, while a mutant deficient in Ube2G2 binding did not (lane 3). As expected, proteasome inhibitor prevented degradation of TCR-α. Together with the siRNA data, these findings provide strong evidence for the importance of Ube2G2 in ERAD. Additionally, they establish the capacity of the Ube2G2 binding site identified in vitro to potently bind and functionally inactivate Ube2G2 in cells.

Example 9

Expression of the Ube2G2 Binding Site Elicits a UPR

Figure 22:
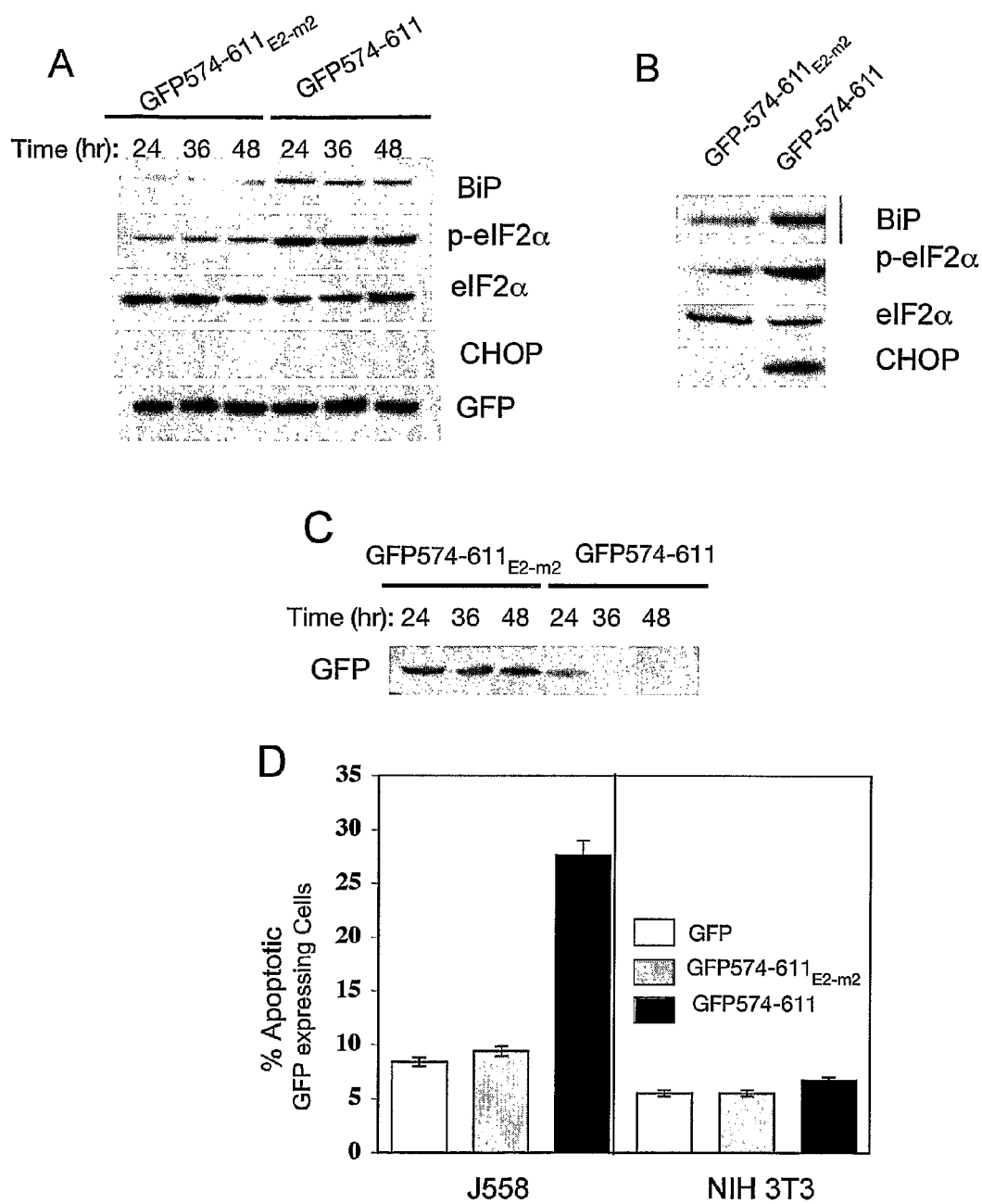
FIGS. 22A-D depict the induction of UPR and apoptosis in myeloma cells by the Ube2g2 binding site.
Figure 23:
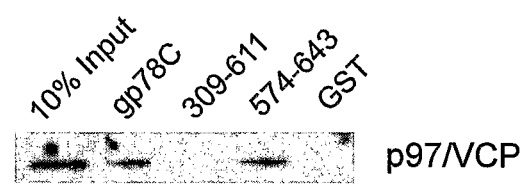
FIG. 23 depicts the requirements for direct binding of p97/VCP to the C-terminus of gp78. Bacterially expressed p97 was incubated with the indicated GST fusion proteins and binding assessed by IB with anti-p97.

The ability to inhibit ERAD suggests that expression of the Ube2G2 binding site might elicit an UPR. This was determined to be the case in HEK 293T cells and confirmed in NIH 3T3 cells where an increase in the ER chaperone BiP was observed with expression of the GFP fusion of the Ube2G2 binding site (GFP574-611) (FIG. 22A). Similarly, an increase in phospho-eIF2α, which attenuates translation and is activated by PERK, was also observed. Importantly, total eIF2α was not significantly altered (FIG. 22A). An effective UPR ultimately requires an increase in ERAD. However, the ectopic expression of the Ube2G2 binding site should create a block specifically at this point. Thus, one might expect to see activation of the pro-apoptotic arm of the UPR However, in NIH 3T3 cells no accumulation of the UPR-activated transcription factor CHOP, which leads to caspase-3 activation and apoptosis, was seen (FIG. 22A). Consistent with this, no microscopic evidence of increased cell death in either HEK 293T cells or NIH 3T3 cells expressing GFP574-611 was observed, nor was there any discernable loss of GFP574-611 relative to the mutant form of the E2 binding site (FIG. 22A, bottom panel). This lack of increased cell death was similarly found for epithelial cancer and sarcoma cell lines including HeLA, U20S and HT1080.

Cells with active secretory pathways, such as myeloma, might be predicted to be particularly susceptible to ER stress. Accordingly, stabilization of the product of the unspliced MRNA for a UPR-regulated transcription factor, XBP-1, has been suggested as an explanation for the efficacy of proteasome inhibitors in multiple myeloma (Lee et al., 2003). As with NIH 3T3 cells, expression of the Ube2G2 binding site in the well characterized myeloma cell line J558 led to increases in BiP and phospho-eIF2α. In contrast to NIH 3T3 cells, a marked increase in CHOP was observed (FIG. 22B).

Consistent with this, a differential loss of J558 cells expressing GFP574-611 relative to those expressing the mutant GFP574-611E2-m2 was seen by microscopy. This was verified by a rapid loss of GFP immunoreactivity from cells expressing GFP574-611 (FIG. 7C). To confirm that this is a consequence of apoptosis, cells were evaluated by flow cytometry 24 hours after transfection. This early point was chosen, as by 48 hours few cells expressing the GFP574-611 could be discerned microscopically. J558 expressing GFP574-611 exhibited a dramatic increase in staining with the apoptosis marker annexin V compared to cells expressing GFP574-611E2-m2 or those expressing GFP alone (FIG. 22D). No significant increase in annexin V staining was seen under similar conditions in NIH 3T3 cells (FIG. 22D). Thus, the isolated Ube2G2 binding site of gp78 initiates an UPR in cells and a program leading to apoptotic cell death preferentially in myeloma cells.

Example 8

Role of the Ube2G2 Binding Site in Human Myeloma

Figure 24:
FIG. 24 depicts the loss of GFP immunoreactivity and CHOP expression in human multiple myeloma cells in the presence of the Ube2G2 binding site.
Figure 25:
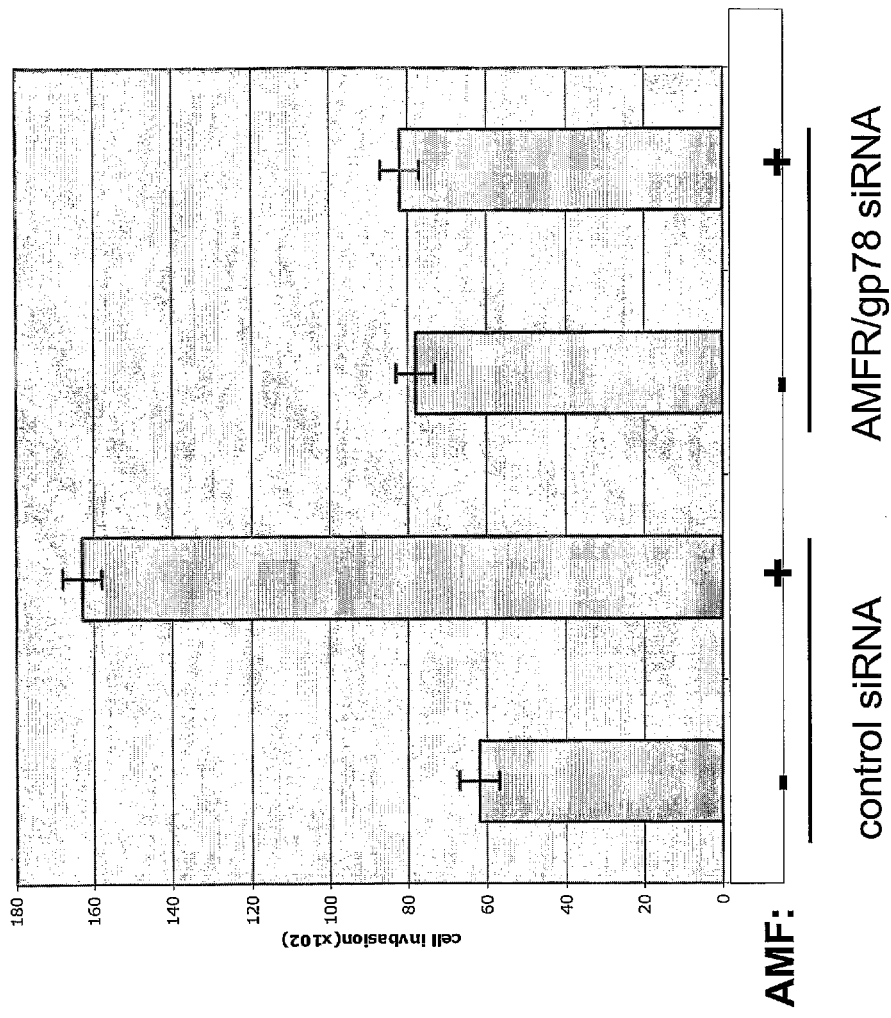
FIG. 25 depicts the decreased invasiveness to AMF HT 1080 cells by AMFR/gp78 knock-down.
Figure 26:
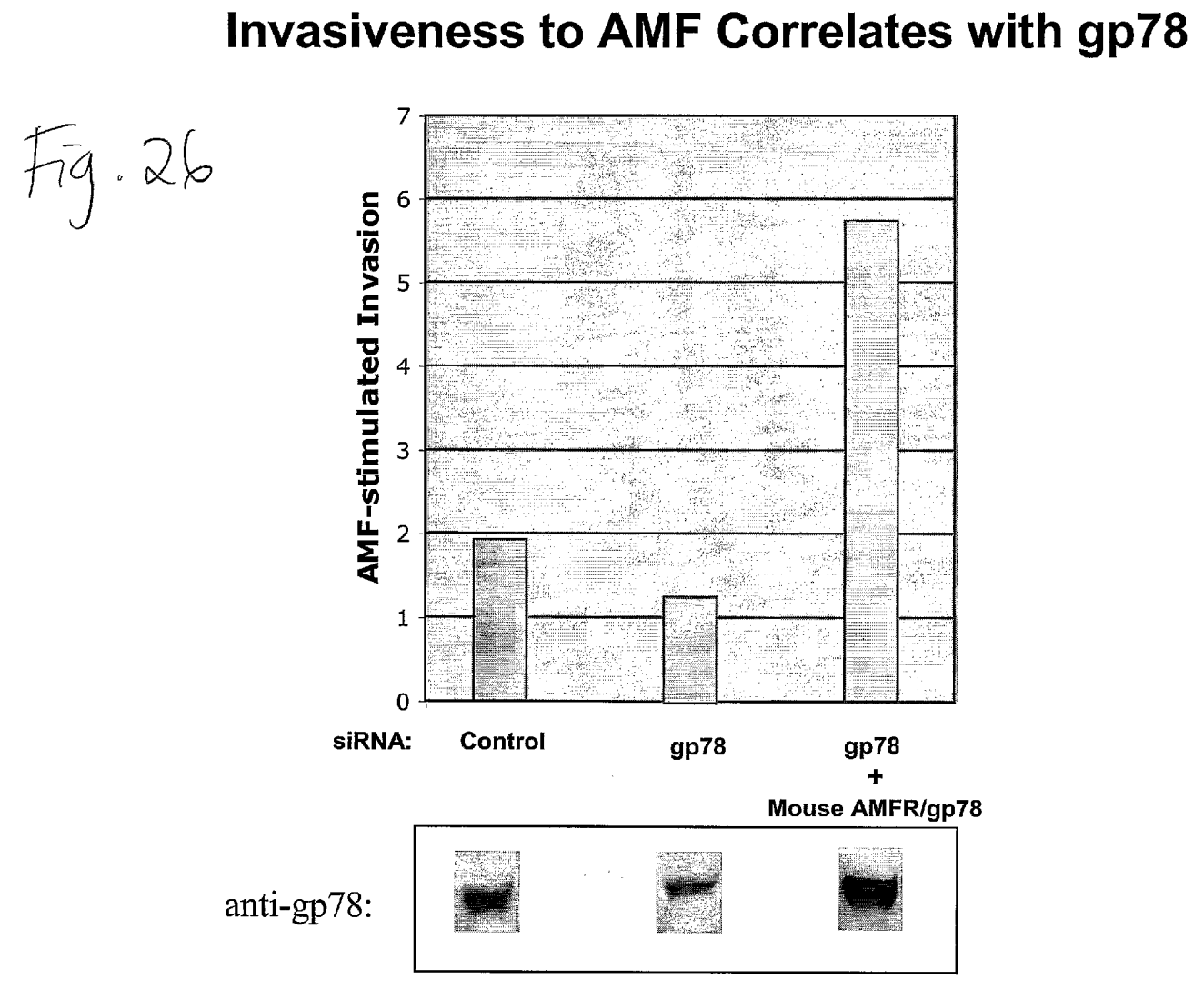
Figure 27:
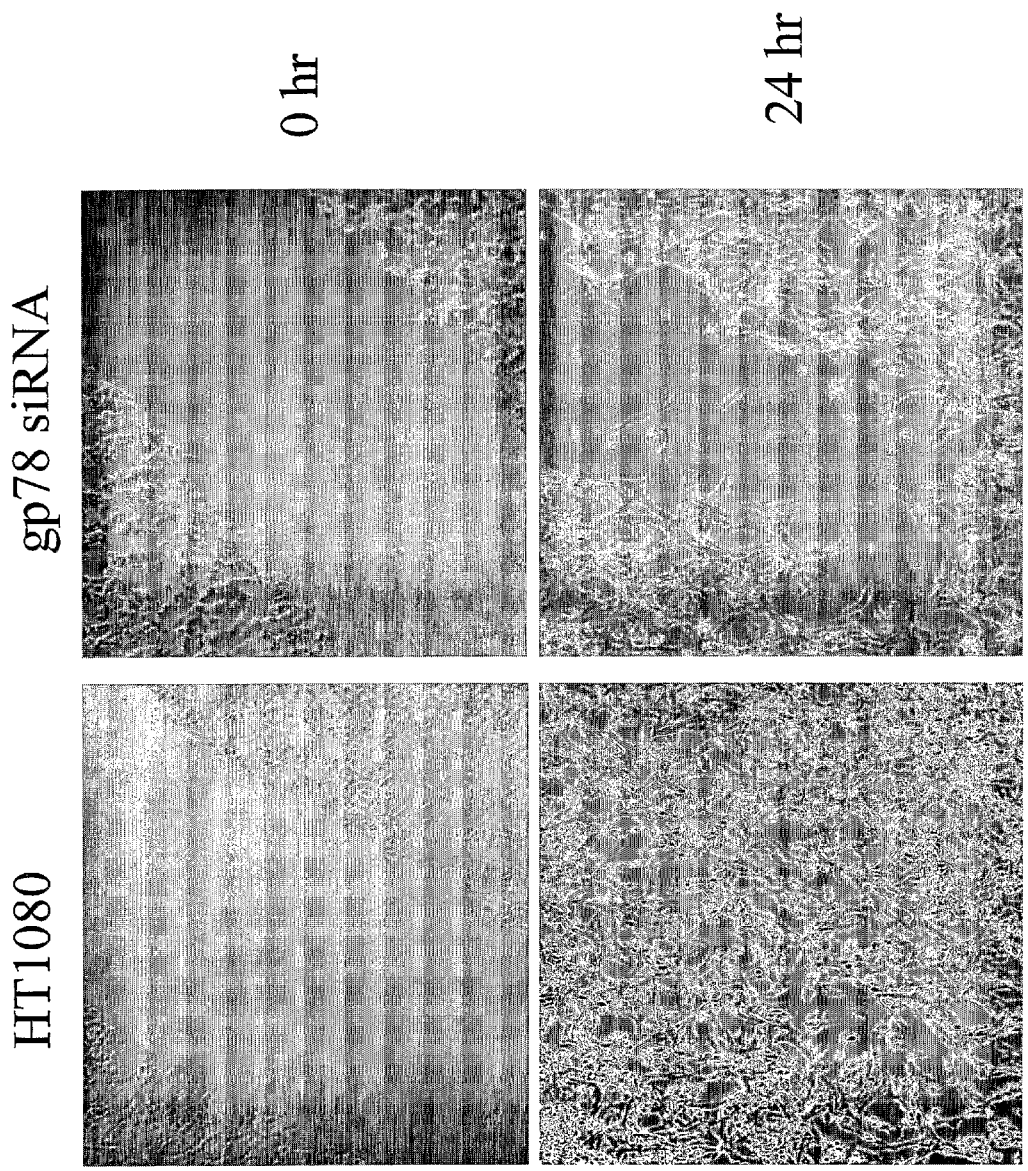
FIG. 27 depicts the reduced migration of HT180 cells in response to siRNA for gp78.

FIG. 24 depicts the loss of GFP immunoreactivity and CHOP expression in human multiple myeloma cells in the presence of the Ube2G2 binding site. Expression of the Ube2G2 binding site also leads to apoptosis in human myelomas. FIG. 25 depicts the decreased invasiveness to AMF HT 1080 cells by AMFR/gp78 knock-down. FIG. 26 depicts the correlation between invasiveness to AMP and gp78. FIG. 27 depicts the reduced migration of HT180 cells in response to siRNA for gp78.

REFERENCES

The following references refer to citations as set forth in the Examples above.

Bartkiewicz, M., Houghton, A., and Baron, R. (1999). Leucine zipper-mediated homodimerization of the adaptor protein c-Cbl. A role in c-Cbl's tyrosine phosphorylation and its association with epidermal growth factor receptor. J Biol Chem 274, 30887-30895.

Bays, N. W., Gardner, R. G., Seelig, L. P., Joazeiro, C. A., and Hampton, R. Y. (2001). Hrd1p/Der3p is a membrane-anchored ubiquitin ligase required for ER-associated degradation. Nat Cell Biol 3, 24-29.

Biederer, T., Volkwein, C., and Sommer, T. (1996). Degradation of subunits of the Sec61p complex, an integral component of the ER membrane, by the ubiquitinproteasome pathway. EMBO J 15, 2069-2076.

Biederer, T., Volkwein, C., and Sommer, T. (1997). Role of Cue1p in ubiquitination and degradation at the ER surface. Science 278, 1806-1809.

Davies, G. C., Ettenberg, S. A., Coats, A. O., Mussante, M., Ravichandran, S., Collins, J., Nau, M. M., and Lipkowitz, S. (2004). Cbl-b interacts with ubiquitinated proteins; differential functions of the UBA domains of c-Cbl and Cbl-b. Oncogene 23, 7104-7115.

Deak, P. M., and Wolf, D. H. (2001). Membrane topology and function of Der3/Hrd1p as a ubiquitin-protein ligase (E3) involved in endoplasmic reticulum degradation. J Biol Chem 276, 10663-1069.

Donaldson, K. M., Yin, H., Gekakis, N., Supek, F., and Joazeiro, C. A. (2003). Ubiquitin signals protein trafficking via interaction with a novel ubiquitin binding domain in the membrane fusion regulator, Vps9p. Curr Biol 13, 258-262.

Fang, S., Ferrone, M., Yang, C., Jensen, J. P., Tiwari, S., and Weissman, A. M. (2001). The tumor autocrine motility factor receptor, gp78, is a ubiquitin protein ligase implicated in degradation from the endoplasmic reticulum. Proc Natl Acad Sci U S A 98, 14422-14427.

Fang, S., and Weissman, A. M. (2004). A field guide to ubiquitylation. Cell Mol Life Sci 61, 1546-1561.

Friedlander, R., Jarosch, E., Urban, J., Volkwein, C., and Sommer, T. (2000). A regulatory link between ER-associated protein degradation and the unfolded-protein response. Nat Cell Biol 2, 379-384.

Hampton, R. Y. (2002). ER-associated degradation in protein quality control and cellular regulation. Curr Opin Cell Biol 14, 476-482.

Hatakeyama, S., Jensen, J. P., and Weissman, A. M. (1997). Subcellular localization and ubiquitin-conjugating enzyme (E2) interactions of mammalian HECT family ubiquitin protein ligases. J Biol Chem 272, 15085-15092.

Hicke, L., and Dunn, R. (2003). Regulation of membrane protein transport by ubiquitin and ubiquitin-binding proteins. Annu Rev Cell Dev Biol 19, 141-172.

Hiller, M. M., Finger, A., Schweiger, M., and Wolf, D. H. (1996). ER degradation of a misfolded luminal protein by the cytosolic ubiquitin-proteasome pathway. Science 273, 1725-1728.

Huyer, G., Piluek, W. F., Fansler, Z., Kreft, S. G., Hochstrasser, M., Brodsky, J. L., and Michaelis, S. (2004). Distinct machinery is required in Saccharomyces cerevisiae for the endoplasmic reticulum-associated degradation of a multispanning membrane protein and a soluble luminal protein. J Biol Chem 279, 38369-38378.

Imai, Y., Soda, M., Inoue, H., Hattori, N., Mizuno, Y., and Takahashi, R. (2001). An unfolded putative transmembrane polypeptide, which can lead to endoplasmic reticulum stress, is a substrate of Parkin. Cell 105, 891-902.

Jarosch, E., Lenk, U., and Sommer, T. (2003). Endoplasmic reticulum-associated protein degradation. Int Rev Cytol 223, 39-81.

Jensen, J. P., Bates, P. W., Yang, M., Vierstra, R. D., and Weissman, A. M. (1995). Identification of a family of closely related human ubiquitin conjugating enzymes. J. Biol. Chem. 270, 30408-30414.

Kang, R. S., Daniels, C. M., Francis, S. A., Shih, S. C., Salerno, W. J., Hicke, L., and Radhakrishnan, I. (2003). Solution structure of a CUE-ubiquitin complex reveals a conserved mode of ubiquitin binding. Cell 113, 621-630.

Kikkert, M., Doolman, R., Dai, M., Avner, R., Hassink, G., van Voorden, S., Thanedar, S., Roitelman, J., Chan, V., and Wiertz, E. (2004). Human HRD1 is an E3 ubiquitin ligase involved in degradation of proteins from the endoplasmic reticulum. J Biol Chem 279, 3525-3534.

Kim, B. W., Zavacki, A. M., Curcio-Morelli, C., Dentice, M., Harney, J. W., Larsen, P. R., and Bianco, A. C. (2003). Endoplasmic reticulum-associated degradation of the human type 2 iodothyronine deiodinase (D2) is mediated via an association between mammalian UBC7 and the carboxyl region of D2. Mol Endocrinol 17, 2603-2612.

Koegl, M., Hoppe, T., Schlenker, S., Ulrich, H. D., Mayer, T. U., and Jentsch, S. (1999). A novel ubiquitination factor, E4, is involved in multiubiquitin chain assembly. Cell 96, 635-644.

Kopito, R. R. (1999). Biosynthesis and degradation of CFTR. Physiol Rev 79, S167-73.

Kostova, Z., and Wolf, D. H. (2003). For whom the bell tolls: protein quality control of the endoplasmic reticulum and the ubiquitin-proteasome connection. EMBO J 22, 2309-2317.

Lee, A. H., Iwakoshi, N. N., Anderson, K. C., and Glimcher, L. H. (2003). Proteasome inhibitors disrupt the unfolded protein response in myeloma cells. Proc Natl Acad Sci U S A 100, 9946-9951.

Liang, J. S., Kim, T., Fang, S., Yamaguchi, J., Weissman, A. M., Fisher, E. A., and Ginsberg, H. N. (2003). Overexpression of the tumor autocrine motility factor receptor Gp78, a ubiquitin protein ligase, results in increased ubiquitinylation and decreased secretion of apolipoprotein B100 in HepG2 cells. J Biol Chem 278, 23984-23988.

Lilley, B. N., and Ploegh, H. L. (2004). A membrane protein required for dislocation of misfolded proteins from the ER. Nature 429, 834-840.

Lin, H., and Wing, S. S. (1999). Identification of rabbit reticulocyte E217K as a UBC7 homologue and functional characterization of its core domain loop. J Biol Chem 274, 14685-14691.

Lorick, K. L., Jensen, J. P., Fang, S., Ong, A. M., Hatakeyama, S., and Weissman, A. M. (1999). RING fingers mediate ubiquitin-conjugating enzyme (E2)-dependent ubiquitination. Proc Natl Acad Sci U S A 96, 11364-11369.

Ma, J., Wollmann, R., and Lindquist, S. (2002). Neurotoxicity and neurodegeneration when PrP accumulates in the cytosol. Science 298, 1781-1785.

Madura, K. (2002). The ubiquitin-associated (UBA) domain: on the path from prudence to prurience. Cell Cycle 1, 235-244.

Madura, K., Dohmen, R. J., and Varshavsky, A. (1993). N-recognin/Ubc2 interactions in the N-end rule pathway. J Biol Chem 268, 12046-12054.

Nabi, I. R., Watanabe, H., Silletti, S., and Raz, A. (1991). Tumor cell autocrine motility factor receptor. EXS 59, 163-177.

Piotrowski, J., Beal, R., Hoffman, L., Wilkinson, K. D., Cohen, R. E., and Pickart, C. M. (1997). Inhibition of the 26 S proteasome by polyubiquitin chains synthesized to have defined lengths. J Biol Chem 272, 23712-23721.

Ponting, C. P. (2000). Proteins of the endoplasmic-reticulum-associated degradation pathway: domain detection and function prediction. Biochem J 351 Pt 2, 527-535.

Prag, G., Misra, S., Jones, E. A., Ghirlando, R., Davies, B. A., Horazdovsky, B. F., and Hurley, J. H. (2003). Mechanism of ubiquitin recognition by the CUE domain of Vps9p. Cell 113, 609-620.

Rutkowski, D. T., and Kaufman, R J. (2004). A trip to the ER: coping with stress. Trends Cell Biol 14, 20-28.

Samelson, L. E., Germain, R. N., and Schwartz, R. H. (1983). Monoclonal antibodies against the antigen receptor on a cloned T-cell hybrid. Proc Natl Acad Sci U S A 80, 6972-6976.

Shih, S. C., Prag, G., Francis, S. A., Sutanto, M. A., Hurley, J. H., and Hicke, L. (2003). A ubiquitin-binding motif required for intramolecular monoubiquitylation, the CUE domain. EMBO J 22, 1273-1281.

Sommer, T., and Jentsch, S. (1993). A protein translocation defect linked to ubiquitin conjugation at the endoplasmic reticulum. Nature 365, 176-179.

Swanson, R., Locher, M., and Hochstrasser, M. (2001). A conserved ubiquitin ligase of the nuclear envelope/endoplasmic reticulum that functions in both ER-associated and Matα2 repressor degradation. Genes Dev 15, 2660-2674.

Takata, M., Maiti, P. K., Kubo, R. T., Chen, Y. H., Holford-Strevens, V., Rector, E. S., and Sehon, A. H. (1990). Cloned suppressor T cells derived from mice tolerized with conjugates of antigen and monomethoxypolyethylene glycol. Relationship between monoclonal T suppressor factor and the T cell receptor. J Immunol 145, 2846-2853.

Thrower, J. S., Hoffman, L., Rechsteiner, M., and Pickart, C. M. (2000). Recognition of the polyubiquitin proteolytic signal. EMBO J 19, 94-102.

Tiwari, S., and Weissman, A. M. (2001). Endoplasmic reticulum (ER)-associated degradation of T cell receptor subunits. Involvement of ER-associated ubiquitinconjugating enzymes (E2s). J Biol Chem 276, 16193-16200.

Webster, J. M., Tiwari, S., Weissman, A. M., and Wojcikiewicz, R. J. (2003). Inositol 1,4,5-trisphosphate receptor ubiquitination is mediated by mammalian Ubc7, a component of the endoplasmic reticulum-associated degradation pathway, and is inhibited by chelation of intracellular Zn2+. J Biol Chem 278, 38238-38246.

Xie, Y., and Varshavsky, A. (1999). The E2-E3 interaction in the N-end rule pathway: the RING-H2 finger of E3 is required for the synthesis of multiubiquitin chain. EMBO J 18, 6832-6844.

Yang, M., Omura, S., Bonifacino, J. S., and Weissman, A. M. (1998). Novel aspects of degradation of T cell receptor subunits from the endoplasmic reticulum (ER) in T cells: importance of oligosaccharide processing, ubiquitination, and proteasome-dependent removal from ER membranes. J Exp Med 187, 835-846.

Ye, Y., Shibata, Y., Yun, C., Ron, D., and Rapoport, T. A. (2004). A membrane protein complex mediates retrotranslocation from the ER lumen into the cytosol. Nature 429, 841-847.

Zhong, X., Shen, Y., Ballar, P., Apostolou, A., Agami, R., and Fang, S. (2004). AAA ATPase p97/valosin-containing protein interacts with gp78, a ubiquitin ligase for endoplasmic reticulum-associated degradation. J Biol Chem 279, 45676-45684.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide, selected from:
   i) a polypeptide consisting of Q-R-M-L-V-Q-R-K-D-E-L-L-Q-Q-A-R-K-R-F-L-N-K (SEQ ID NO:34);
   ii) a polypeptide having at least 80% sequence identity to the amino acid sequence of SEQ ID NO:34;
   iii) a polypeptide having at least 90% sequence identity to the amino acid sequence of SEQ ID NO:34
   iv) a polypeptide consisting of A-A-A-A-G-Q-R-M-L-V-Q-Xn-R-F-L-N-K (SEQ ID NO:59), wherein X is an amino acid residue, and n is any number from 0-50;
   v) a polypeptide consisting of Q-R-M-L-V-Q-Xn-R-F-L-N-K (SEQ ID NO:48), wherein X is an amino acid residue, and n is any number from 0-50;
   vi) a polypeptide consisting of 22-30 amino acids, wherein the 22-30 amino acid polypeptide comprises Q-R-M-L-V-Q-R-K-D-E-L-L-Q-Q-A-R-K-R-F-L-N-K (SEQ ID NO:34);
   vii) a polypeptide consisting of 22-30 amino acids, wherein the 22-30 amino acid polypeptide comprises a polypeptide having at least 80% sequence identity to the amino acid sequence of SEQ ID NO:34; or
   viii) a polypeptide consisting of 22-30 amino acids, wherein the 22-30 amino acid polypeptide comprises a polypeptide having at least 90% sequence identity to the amino acid sequence of SEQ ID NO:34.

2. A method of detecting the ubiquitin conjugating enzyme E2G2 (Ube2G2) in a sample, wherein the method comprises:
   a) contacting the sample with the polypeptide of claim 1; and
   b) determining whether the polypeptide binds to the Ube2G2 in the sample, to thereby detect the presence of Ube2G2 in the sample.

* * * * *